United States Patent [19]
Lin et al.

[11] Patent Number: 6,028,183
[45] Date of Patent: Feb. 22, 2000

[54] PYRIMIDINE DERIVATIVES AND OLIGONUCLEOTIDES CONTAINING SAME

[75] Inventors: Kuei-Ying Lin, Fremont; Mark D. Matteucci, Portola Valley, both of Calif.

[73] Assignee: Gilead Sciences, Inc., Foster City, Calif.

[21] Appl. No.: 08/966,392

[22] Filed: Nov. 7, 1997

[51] Int. Cl.[7] ............................. C07H 19/00; C07H 21/00
[52] U.S. Cl. ................... 536/22.1; 536/23.1; 536/25.3; 536/25.31; 536/25.32; 536/25.34; 536/25.4; 435/6; 435/87; 435/90; 544/249
[58] Field of Search ............................. 536/22.1, 23.1, 536/25.3, 25.31, 25.32, 25.34, 25.4; 435/6, 87, 90; 544/249

[56] References Cited

U.S. PATENT DOCUMENTS

| | | |
|---|---|---|
| 4,233,402 | 11/1980 | Maggio et al. . |
| 5,286,717 | 2/1994 | Cohen et al. . |
| 5,502,177 | 3/1996 | Matteucci et al. . |
| 5,594,121 | 1/1997 | Froehier et al. . |
| 5,614,617 | 3/1997 | Cook et al. . |
| 5,614,622 | 3/1997 | Iyer et al. . |
| 5,623,068 | 4/1997 | Reddy et al. . |
| 5,645,985 | 7/1997 | Froehler et al. . |
| 5,668,272 | 9/1997 | Prasad et al. . |
| 5,728,528 | 3/1998 | Mathies et al. . |

FOREIGN PATENT DOCUMENTS

| | | |
|---|---|---|
| 0 487 289 A2 | 5/1992 | European Pat. Off. . |
| 0 541 153 A1 | 5/1993 | European Pat. Off. . |
| 62-059293 A2 | 3/1987 | Japan . |
| WO 88/10264 | 12/1988 | WIPO . |
| WO 90/15065 | 12/1990 | WIPO . |
| WO 91/06626 | 5/1991 | WIPO . |
| WO 91/06629 | 5/1991 | WIPO . |
| WO 92/02258 | 2/1992 | WIPO . |
| WO 92/20702 | 11/1992 | WIPO . |
| WO 93/10820 | 6/1993 | WIPO . |
| WO 93/13121 | 7/1993 | WIPO . |
| WO 93/24507 | 12/1993 | WIPO . |
| WO 96/05298 | 2/1996 | WIPO . |
| WO 96/37504 | 11/1996 | WIPO . |
| WO 97/14706 | 4/1997 | WIPO . |
| WO 97/28176 | 8/1997 | WIPO . |
| WO 97/31008 | 8/1997 | WIPO . |
| WO 97/32888 | 9/1997 | WIPO . |

OTHER PUBLICATIONS

Bell, et al., "Highly Effective Hydrogen–Bonding Receptors for Guanine Derivatives", 34(19):2163–2165, Angew Chem Int Ed, 1995.

Dande, et al., "Regioselective Effect of Zwitterionic DNA Substitutions on DNA Alkylation: Evidence for a Strong Side Chain Orientational Preference", 36:6024–6032, Biochem, 1997.

Haginoya et al., "Nucleosides and Nucletides. 160, Synthesis of Oligodeoxyribonucleotides Containing 5–(N–Aminoalky)carbamoyl–2'–deoxyuridines by a New Postsynthetic Modification Method and Their Thermal Stability and Nuclease–Resistance Properties", 8:271–280, Bioconj Chem, 1997.

Lin et al., "Tricyclic 2'-Deoxycytidine Analogs: Synthesis and Incoporation into Oligodeoxynucleotides Which Have Enhance Binding to Complementary RNA", 117:3873–3874, J. Am Chem Soc, 1995.

Matteucci et al., "In pursuit of antisence", 384(7):20–22, Nature, 1996.

Prober et al., "A System for Rapid DNA Sequencing with Fluroescent Chain–Terminating Dideoxynucleotides", 238:336–341, Science, 1987.

Ueno et al., "Effects of 5–(N–aminohexyl)carbamoyl–2'–dexyuridine on endonuclease stability and the ability of oligodeoxynucleotide to activate RNase H", 25(19):3777–3782, Nuc Acids Res, 1997.

Ulmann et al, "Antisense Oligonucleotides: A New Therapeutic Principle", 90(4):543–584, Chem Rev, 1990.

Primary Examiner—James O. Wilson
Attorney, Agent, or Firm—Woodcock Washburn Kurtz Mackiewicz & Norris LLP

[57] ABSTRACT

Compounds having structure (1)

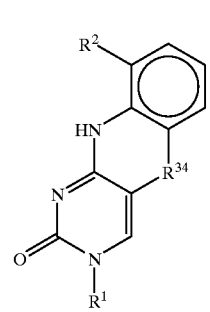

wherein $R^1$ is —H a protecting group, a linker or a binding partner; and $R^2$ and $R^{34}$ are as defined in the specification. The invention also provides intermediates and methods make the structure (1) compounds, as well as methods to use the compounds as labels in diagnostic assays and to enhance binding to complementary bases.

30 Claims, No Drawings

PYRIMIDINE DERIVATIVES AND OLIGONUCLEOTIDES CONTAINING SAME

BACKGROUND OF THE INVENTION

This invention relates to the field of labels, particularly labels for diagnostic or analytical use. In particular, it relates to oligonucleotides that are modified to enhance the binding affinity or the binding specificity of the oligonucleotides for complementary sequences and that in addition optionally bear a readily detectable characteristic.

Sequence specific binding of oligonucleotides both to single stranded RNA and DNA and to duplex DNA is widely known. This phenomenon has been harnessed for a great variety of diagnostic, therapeutic and analytical, e.g., sequence determination or gene mapping, purposes. Previously, one objective of research in this field has been to increase the affinity of such oligonucleotides for their complementary sequences. For example, workers have described oligonucleotides containing 5-substituted pyrimidine bases that substantially increase the Tm for oligonucleotide binding to complementary bases (International Publication No. WO 93/10820).

Publications have described the use of fluorescent cytosine derivatives to prepare labeled DNA probes. See Inoue et al., Jpn. Kokai JP 62059293, (1987). In addition, fluorescent labeled nucleotides have been employed in DNA sequencing. See Prober et al., "Science" 238:336–341 (1987).

1,3-Dihydro-2H-imidazo[4,5-b]-quinolin-2-one derivatives as phosphodiesterase inhibitors are disclosed by Raeymaekers et al. (EP 541,153).

U.S. Pat. No. 5,502,177, discloses phenoxazine polycycle-containing oligonucleotides and monomers for preparing the oligonucleotides.

OBJECTS OF THE INVENTION

The invention compositions or methods accomplish one or more of the following objects.

An object of this invention is to increase the affinity of oligonucleotides for their complementary sequences.

An object of this invention is to increase the specificity of oligonucleotides for their complementary sequences.

Another object of this invention is to provide detectable labels for use in diagnostic assays.

Another object is to enhance diagnostic assays that use oligonucleotides.

Another object is to improve the therapeutic efficacy of oligonucleotides.

Another object is to improve the potency of oligonucleotides as antisense reagents that affect gene expression by altering intracellular metabolism of complementary RNA sequences encoding a target gene(s).

Another object is to provide chemical intermediates and synthesis methods to prepare the invention compositions.

These and other objects of the invention will be apparent when one considers the disclosure as a whole.

SUMMARY OF THE INVENTION

In accordance with the objects, the invention provides compounds having the structure (1)

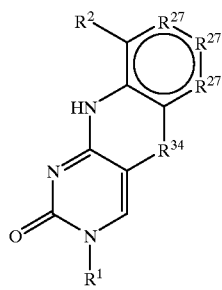

(1)

and tautomers, solvates and salts thereof, wherein $R^1$ is a binding partner, a protecting group, a linker or —H;

$R^2$ is $A(Z)_{X1}$, wherein A is a spacer and Z independently is a label bonding group optionally bonded to a detectable label, but $R^2$ is not amine, protected amine, nitro or cyano;

$R^{27}$ is independently —CH=, —N=, —C($C_{1-8}$ alkyl)= or —C(halogen)=, but no adjacent $R^{27}$ are both —N=, or two adjacent $R^{27}$ are taken together to form a ring having the structure,

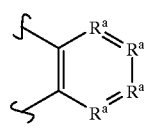

where $R^a$ is independently —CH=, —N=, —C($C_{1-8}$ alkyl)= or —C(halogen)=, but no adjacent $R^a$ are both —N=;

$R^{34}$ is —O—, —S— or —N(CH$_3$)—; and

X1 is 1, 2 or 3.

When the binding partner $R^1$ is an oligonucleotide, embodiments of the compounds of this invention include oligonucleotides of structure (2), (2A), (2B), or (2C)

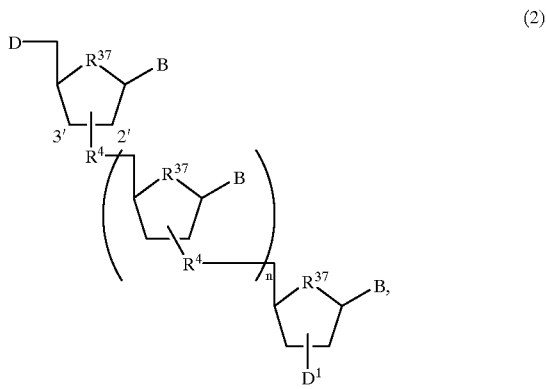

(2)

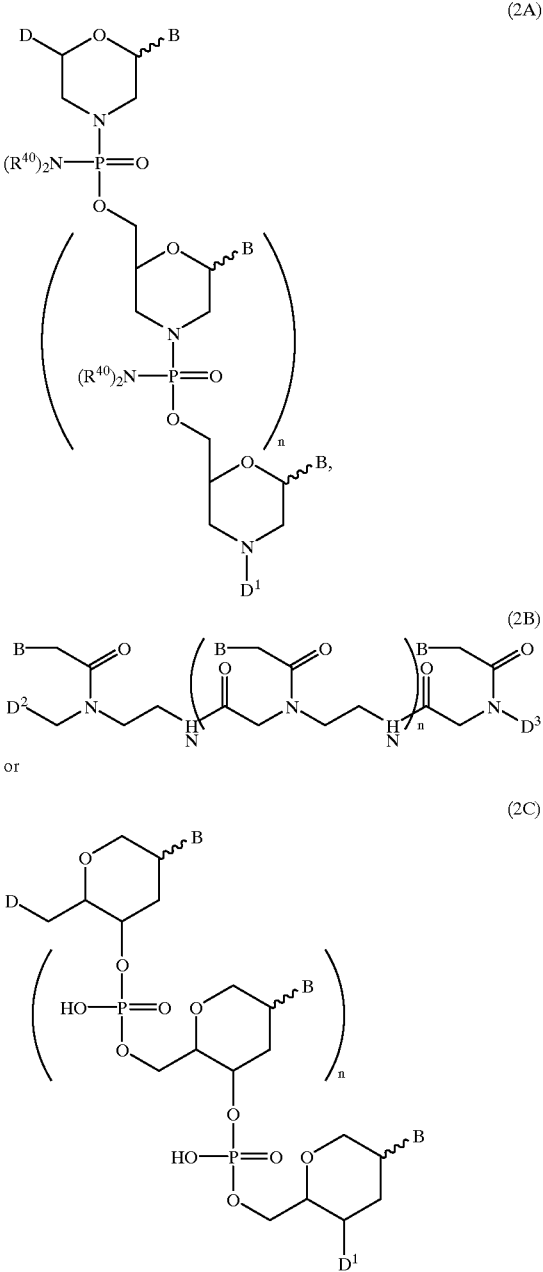

and the adjacent 2' or 3' position in structure (2) is substituted with $R^{21}$;

$R^5$ is independently —H or a protecting group;

$R^{21}$ is independently —H, —OH, halogen or a moiety that enhances the oligonucleotide against nuclease cleavage;

$R^{37}$ is independently —O—, —$CH_2$— or —$CF_2$—;

n is an integer from 0 to 98; and

B independently is a purine or pyrimidine base or a protected derivative thereof, provided that at least one B is a base of structure (3)

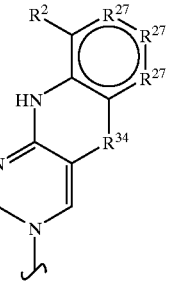

(3)

Embodiments include compositions useful as intermediates in making the structure (1) compounds, including intermediates having structure (4)

(4)

and tautomers, solvates and salts thereof wherein, $R^{24}$ is a halogen; and $R^{25}$ is —SH, —OH, =S or =O.

In a further embodiment, the invention includes contacting a structure (2), (2A), (2B), or (2C) oligonucleotide, wherein n is at least about 7, with a sample suspected to contain a nucleic acid having a base sequence that is at least substantially complementary to the structure (2), (2A), (2B), or (2C) oligonucleotide.

In a further embodiment, the invention includes detecting the presence, absence or amount of a complex comprising a structure (2), (2A), (2B), or (2C) oligonucleotide, wherein n is at least about 7, and a nucleic acid having a base sequence that is at least substantially complementary to the structure (2), (2A), (2B), or (2C) oligonucleotide.

In a further embodiment, the invention includes converting a structure (4) compound to a compound of structure (1) where $R^{34}$ is —O— or —S— and the $R^2$ atom or moiety alpha to the ring containing $R^{27}$ is —O—, —S— or —$CH_2$—, by displacing $R^{24}$.

In a further embodiment, the invention includes converting a structure (4A) compound (a structure (1) compound where $R^2$ is replaced with —$NH_2$); to a compound of wherein D is —OH, protected —OH, an oligonucleotide coupling group or a solid support;

$D^1$ is an oligonucleotide coupling group, —OH, protected —OH or a solid support, wherein $D^1$ is bonded to one 2' or 3' position in the oligonucleotide of structure (2) and the adjacent 2' or 3' position in structure (2) is substituted with $R^{21}$, provided that D and $D^1$ are not both an oligonucleotide coupling group or they are not both a solid support;

$D^2$ is —$CO_2R^5$, —C(O)N($R^5$)$_2$, —$SO_3R^5$, —$SO_2$N($R^5$)$_2$ or an activated derivative of —$CO_2$H or —$SO_3$H;

$D^3$ is a protecting group, —H or —($CH_2$)$_{2-6}$—N($R^5$)$_2$;

$R^4$ is independently a phosphodiester linkage or a phosphodiester substitute linkage, wherein $R^4$ is bonded to one 2' or 3' position in the structure (2) oligonucleotide structure (1), by reductive alkylation of the —NH$_2$ group to yield a structure (1) compound where the R$^2$ moiety alpha to the ring containing R$^{27}$ is —NH—.

DETAILED DESCRIPTION OF THE INVENTION

The invention comprises all combinations formed by independently selecting individual Markush group members and assembling them in accordance with the teachings herein. The invention optionally excludes any feature or substance found in, or obvious over, the prior art.

Structural formulas are designated as parenthetical numerals. We intend that designation of aromaticity with respect to carbocycles and heterocycles herein includes any highly resonant unsaturated ring structure. Alternatively, placement of double bonds, where indicated, represents one potential structure for the depicted compound but we intend this depiction to include other resonant states of the compound as well as protonated and charged species, only one of which a structure may show.

The invention includes invention compounds in unpurified, substantially purified and purified forms. It includes invention compounds that are present with any additional component(s) such as a solvent, reactant or by-product that is present during invention compound synthesis or purification, and any additional component(s) that is present during the use or manufacture of an invention compound.

Halo and halogen mean F, Cl, Br or I.

Alkyl means unbranched, branched or cyclic hydrocarbons that are saturated or unsaturated, or combinations thereof. Alkyl includes all isomers, e.g., stereoisomers, positional isomers, diastereomers and regioisomers. Alkyl moieties that are unsaturated will typically contain 1, 2, 3 or more —CH═CH— or —C≡C— groups, usually one such group.

Substituted alkyl means unbranched, branched or cyclic hydrocarbons that are saturated or unsaturated, or combinations thereof, where the hydrocarbon contains a heteroatom linked to a carbon or a heteroatom that replaces a carbon atom. Substituted alkyl includes all isomers, e.g., stereoisomers, positional isomers, diastereomers and regioisomers. Substituted alkyl moieties that are unsaturated will typically contain 1, 2, 3 or more —CH═CH— or —C≡—C— groups, usually one such group. Substituted alkyl includes alkyl groups having substituents linked to a carbon atom or substituents that interrupt a carbon atom chain, and unless otherwise defined, substituents include ethers (—O—), ketones (—C(O)—), —OR$^5$, —C(O)OR$^5$, —C(O)O—, —OC(O)—, —C(O)H, —OCH$_2$—, —OCH$_2$CH$_2$—, —OCH$_2$O—, —OCH$_2$CH$_2$O—, —NR$^5$—, —NHR$^5$, —NHC(O)—, —C(O)NH—, C(O)NHR$^5$, —OC(O)NR$^5$—, —OC(O)NHR$^5$, —NR$^5$C(O)NR$^5$—, —NR$^5$C(O)NHR$^5$, —NR$^5$CH$_2$—, —NR$^5$CH$_2$CH$_2$—, —S—, —SR$^5$, —S(O)—, —S(O)(O)—, —S(O)OR$^5$, —S(O)H, halogen, CN, NO$_2$, and combinations of these substituents where R$^5$ is hydrogen or a protecting group.

The invention compounds herein do not include obviously unstable structures, e.g., —O—O—, —O—S— or unsaturated cyclopropyl, unless they are useful as transitory intermediates in the preparation of more stable compounds.

As used herein, "monosaccharide" means a polyhydroxy aldehyde or ketone having the empirical formula (CH$_2$O)$_n$ where n is 3, 4, 5, 6 or 7. Monosaccharide includes open-chain and closed-chain forms, but will usually be closed chain forms. Monosaccharide includes hexofuranose and pentofuranose sugars such as 2'-deoxyribose, ribose, arabinose, xylose, their 2'-deoxy and 3'-deoxy derivatives, their 2',3'-dideoxy derivatives, and their derivatives containing R$^{21}$ linked to the 2' or 3' position, usually the 2' position. Monosaccharide also includes the 2',3' dideoxydidehydro derivative of ribose. Monosaccharides include the D- and L-isomers of glucose, fructose, mannose, idose, galactose, allose, gulose, altrose, talose, fucose, erythrose, threose, lyxose, erythrulose, ribulose, xylulose, ribose, arabinose, xylose, psicose, sorbose, tagatose, glyceraldehyde, dihydroxyacetone and their monodeoxy derivatives such as rhamnose. Monosaccharides are optionally protected or partially protected.

As used herein, a "protecting group" means a moiety that prevents the atom to which it is linked from participating in unwanted reactions. For example, for —OR$^5$, R$^5$ is a protecting group for the oxygen atom found in a hydroxyl or carboxyl group, for —SR$^5$, R$^5$ is a protecting group for sulfur in thiols for instance, and for —NHR$^5$ or —N(R$^5$)—, R$^5$ is a nitrogen atom protecting group for primary or secondary amines. Hydroxyl, amine and other reactive groups are found in invention compounds at, e.g., R$^2$, R$^{21}$ or oligonucleotide linkages or oligonucleotide bases. These groups may require protection against reactions taking place elsewhere in the molecule. The protecting groups for oxygen, sulfur or nitrogen atoms are usually used to prevent unwanted reactions with electrophilic compounds, such as acylating or phosphorylating agents used, e.g., in nucleoside, nucleotide or oligonucleotide chemistry.

Protecting groups are intended to be removed by known procedures, although it will be understood that the protected intermediates fall within the scope of this invention. The removal of the protecting group may be arduous or straightforward, depending upon the economics and nature of the conversions involved. In general, one will use a protecting group with exocyclic amines in the B groups of the compounds of this invention. For oligonucleotide containing such B groups to be fully binding competent, exocyclic amines must be deprotected because the amine groups participate in hydrogen bonding with complementary bases. Similarly, one will typically use reversible protecting groups for the 5' and 3' hydroxyl groups of pentofuranose sugars in nucleotides intended for use as monomers in synthesis of oligonucleotides containing 3,5' linkages. Protecting groups commonly are employed to protect against covalent modification of a sensitive group in reactions such as phosphorylation, alkylation or acylation. Ordinarily, protecting groups are removed by, e.g. hydrolysis, elimination or aminolysis. Thus, simple functional considerations will suffice to guide the selection of a reversible or an irreversible protecting group at a given locus on the invention compounds. Suitable protecting groups and criteria for their selection are described in T. W. Greene and P. G. M. Wuts, Eds. "Protective Groups in Organic Synthesis" 2nd edition, Wiley Press, at pps. 10–142, 143–174, 175–223, 224–276, 277–308, 309–405 and 406–454.

Salts

Embodiments include salts and complexes of invention compounds, including pharmaceutically acceptable or salts that are relatively non-toxic. The invention compounds may have one or more moieties that carry at least a partial positive or negative charge in aqueous solutions, typically at a pH of about 4–10, that can participate in forming a salt, a complex, a composition with partial salt and partial complex properties or other noncovalent interactions, all of which we refer to as a "salt(s)". Salts are usually biologically compatible or pharmaceutically acceptable or non-toxic, particularly for mammalian cells. Salts that are biologically toxic are optionally used with synthetic intermediates of invention compounds. When a water soluble composition is desired, monovalent salts are usually preferred.

Metal salts typically are prepared by reacting the metal hydroxide with a compound of this invention. Examples of metal salts which are optionally prepared in this way are salts containing $Li^+$, $Na^+$, and $K^+$. A less soluble metal salt can be precipitated from the solution of a more soluble salt by adding a suitable metal compound. Invention salts may be formed from acid addition of certain organic acids, such as organic carboxylic acids, and inorganic acids, such as alkylsulfonic acids or hydrogen halide acids, to acidic or basic centers on invention compounds, such as basic centers on the invention pyrimidine base analogs. Metal salts include ones containing $Na^+$, $Li^+$, $K^+$, $Ca^{++}$ or $Mg^{++}$. Other metal salts may contain aluminum, barium, strontium, cadmium, bismuth, arsenic or zinc ion.

Salt(s) of invention compounds may comprise a combination of appropriate cations such as alkali and alkaline earth metal ions or ammonium and quaternary ammonium ions with the acid anion moiety of the phosphoric acid or phosphonic acid group, which may be present in invention polymers or monomers.

Salts are produced by standard methods, including dissolving free base in an aqueous, aqueous-alcohol or aqueous-organic solution containing the selected acid, optionally followed by evaporating the solution. The free base is reacted in an organic solution containing the acid, in which case the salt usually separates directly or one can concentrate the solution.

Suitable amine salts include amines having sufficient basicity to form a stable salt, preferably amines of low toxicity including trialkyl amines (tripropylamine, triethylamine, trimethylamine), procaine, dibenzylamine, N-benzyl-betaphenethylamine, ephenamine, N,N'-dibenzylethylenediamine, N-ethylpiperidine, benzylamine and dicyclohexylamine.

Salts include organic sulfonic acid or organic carboxylic acid salts, made for example by addition of the acids to basic centers, typically amines. Exemplary sulfonic acids include $C_{6-16}$ aryl sulfonic acids, $C_{6-16}$ heteroaryl sulfonic acids and $C_{1-16}$ alkyl sulfonic acids such as phenyl sulfonic acid, a-naphthalene sulfonic acid, β-naphthalene sulfonic acid, (S)-camphorsulfonic acid, methyl ($CH_3SO_3H$), ethyl ($C_2H_5SO_3H$), n-propyl, i-propyl, n-butyl, s-butyl, i-butyl, t-butyl, pentyl and hexyl sulfonic acids. Exemplary organic carboxylic acids include $C_{1-16}$ alkyl, $C_{6-16}$ aryl carboxylic acids and $C_{4-16}$ heteroaryl carboxylic acids such as acetic, glycolic, lactic, pyruvic, malonic, glutaric, tartaric, citric, fumaric, succinic, malic, maleic, oxalic, hydroxymaleic, benzoic, hydroxybenzoic, phenylacetic, cinnamic, salicylic, nicotinic and 2-phenoxybenzoic.

Invention salts include those made from inorganic acids, e.g., HF, HCl, HBr, HI, $H_2SO_4$, $H_3PO_4$, $Na_2CO_3$, $K_2CO_3$, $CaCO_3$, $MgCO_3$ and $NaClO_3$. Suitable anions, which are optionally present with a cation such a $Ca^{++}$, $Mg^{++}$, $Li^+$, $Na^+$ or $K^+$, include arsenate, arsenite formate, sorbate, chlorate, perchlorate, periodate, dichromate, glycodeoxycholate, cholate, deoxycholate, desoxycholate, taurocholate, taurodeoxycholate, taurolithocholate, tetraborate, nitrate, nitrite, sulfite, sulfamate, hyposulfite, bisulfite, metabisulfite, thiosulfate, thiocyanate, silicate, metasilicate, $CN^-$, gluconate, gulcuronate, hippurate, picrate, hydrosulfite, hexafluorophosphate, hypochlorite, hypochlorate, borate, metaborate, tungstate and urate.

Salts also include the invention compound salts with one or more amino acids. Many amino acids are suitable, especially the naturally-occurring amino acids found as protein components, although the amino acid typically is one bearing a side chain with a basic or acidic group, e.g., lysine, arginine, histidine or glutamic acid, or a neutral group such as glycine, serine, threonine, alanine, isoleucine, or leucine.

The invention compositions include compounds in their un-ionized, as well as zwitterionic form, and combinations with stoiochimetric amounts of water as in hydrates.

Stereoisomers

The compounds of the invention include enriched or resolved optical isomers at any or all asymmetric atoms as are apparent from the depictions. Both racemic and diasteromeric mixtures, as well as the individual optical isomers isolated or synthesized so as to be substantially free of their enantiomeric or diastereomeric partners, are all within the scope of the invention. Chiral centers may be found in invention compounds at, for example, $R^1$, $R^2$ and $R^{21}$.

One or more of the following enumerated methods are used to prepare the enantiomerically enriched or pure isomers herein. The methods are listed in approximately their order of preference, i.e., one ordinarily should employ stereospecific synthesis from chriral precursors before chromatographic resolution before spontaneous crystallization.

Stereospecific synthesis is described in the examples. Methods of this type conveniently are used when the appropriate chiral starting material is available and reaction steps are chosen do not result in undesired racemization at chiral sites. One advantage of stereospecific synthesis is that it does not produce undesired enantiomers that must be removed from the final product, thereby lowering overall synthetic yield. In general, those skilled in the art would understand what starting materials and reaction conditions should be used to obtain the desired enantiomerically enriched or pure isomers by stereospecific synthesis. If an unexpected racemization occurs in a method thought to be stereospecific then one needs only to use one of the following separation methods to obtain the desired product.

If a suitable stereospecific synthesis cannot be empirically designed or determined with routine experimentation then those skilled in the art would turn to other methods. One method of general utility is chromatographic resolution of enantiomers on chiral chromatography resins. These resins are packed in columns, commonly called Pirkle columns, and are commercially available. The columns contain a chiral stationary phase. The racemate is placed in solution and loaded onto the column, and thereafter separated by HPLC. See for example, Proceedings Chromatographic Society—International Symposium on Chiral Separations, Sep. 3–4, 1987. Examples of chiral columns that could be used to screen for the optimal separation technique would include Diacel Chriacel OD, Regis Pirkle Covalent D-phenylglycine, Regis Pirkle Type 1A, Astec Cyclobond II, Astec Cyclobond III, Serva Chiral D-DL=Daltosil 100, Bakerbond DNBLeu, Sumipax OA-1000, Merck Cellulose Triacetate column, Astec Cyclobond I-Beta, or Regis Pirkle Covalent D-Naphthylalanine. Not all of these columns are likely to be effective with every racemic mixture. However, those skilled in the art understand that a certain amount of routine screening may be required to identify the most effective stationary phase. When using such columns it is desirable to employ embodiments of the compounds of this invention in which the charges are not neutralized, e.g., where acidic functionalities such as carboxyl are not esterified or amidated.

Another method entails converting the enantiomers in the mixture to diasteriomers with chiral auxiliaries and then separating the conjugates by ordinary column chromatography. This is a very suitable method, particularly when the embodiment contains free carboxyl, amino or hydroxyl that will form a salt or covalent bond to a chiral auxiliary. Chirally pure amino acids, organic acids or organosulfonic acids are all worthwhile exploring as chiral auxiliaries, all of which are well known in the art. Salts with such auxiliaries can be formed, or they can be covalently (but reversibly) bonded to the functional group. For example, pure D or L amino acids can be used to amidate the carboxyl group of embodiments of this invention and then separated by chromatography. Enzymatic resolution is another method of potential value. In such methods one prepares covalent derivatives of the enantiomers in the racemic mixture, generally lower alkyl esters (for example of carboxyl), and then exposes the derivative to enzymatic cleavage, generally hydrolysis. For this method to be successful an enzyme must be chosen that is capable of stereospecific cleavage, so it is frequently necessary to routinely screen several enzymes. If esters are to be cleaved, then one selects a group of esterases, phosphatases, and lipases and determines their activity on the derivative. Typical esterases are from liver, pancreas or other animal organs, and include porcine liver esterase.

If the enatiomeric mixture separates from solution or a melt as a conglomerate, i.e., a mixture of enantiomerically-pure crystals, then the crystals can be mechanically separated, thereby producing the enantiomerically enriched preparation. This method, however, is not practical for large scale preparations and is of no value for true racemic compounds.

Asymmetric synthesis is another technique for achieving enantiomeric enrichment. For example, a chiral protecting group is reacted with the group to be protected and the reaction mixture allowed to equilibrate. If the reaction is enantiomerically specific then the product will be enriched in that enantiomer.

Further guidance in the separation of enantiomeric mixtures can be found, by way of example and not limitation, in "Enantiomers, Racemates, and resolutions", Jean Jacques, Andre Collet, and Samuel H. Wilen (Krieger Publishing Company, Malabar, Fla., 1991, ISBN 0-89464-618-4): Part 2, Resolution of Enantiomer Mixture, pages 217–435; more particularly, section 4, Resolution by Direct Crystallization, pages 217–251, section 5, Formation and Separation of Diastereomers, pages 251–369, section 6, Crystallization-Induced Asymmetric Transformations, pages 369–378; and section 7, Experimental Aspects and Art of Resolutions, pages 378–435; still more particularly, section 5.1.4, Resolution of Alcohols, Transformation of Alcohols into Salt-Forming Derivatives, pages 263–266, section 5.2.3, Covalent Derivatives of Alcohols, Thiols, and Phenols, pages 332–335, section 5.1.1, Resolution of Acids, pages 257–259, section 5.1.2, Resolution of Bases, pages 259–260, section 5.1.3, Resolution of Amino Acids, page 261–263, section 5.2.1, Covalent Derivatives of Acids, page 329, section 5.2.2, Covalent derivatives of Amines, pages 330–331, section 5.2.4, Covalent Derivatives of Aldehydes, Ketones, and Sulfoxides, pages 335–339, and section 5.2.7, Chromatographic Behavior of Covalent Diastereomers, pages 348–354.

Compounds of Structure (1)—Polycyclic Substructure $R^2$ is a key functionality. It is substituted on the polycycle depicted in structure (1), less $R^2$. The combination of the polycycle and $R^2$ is termed the polycyclic substructure. $R^2$ consists of two principal structural features denominated —$A(Z)_{X1}$. Group A is a spacer that is used to position the Z group(s) and attach it to the remainder of the polycycle. The Z group(s) serve as a site for attachment of a detectable label or to enhance the hydrogen bonding of the polycycle to the complementary guanine base. In some embodiments, Z is capable of performing both functions. For the most part, Z groups capable of hydrogen bonding are useful as sites for covalent bonding to detectable labels, but not all Z groups that are useful as label-bonding sites are capable of hydrogen bonding to guanine. Z contains at least one atom other than carbon, typically O, N or S. In any case, the $R^2$ groups possess at least one of these practical utilities. It would be routine to make and test them to determine the best use of any one embodiment.

Z groups capable of base-pairing are believed to hydrogen bond with $N^7$ of guanine in a complementary nucleic acid sequence when incorporated into a polycyclic substructure-substituted oligonucleotide. The resulting duplex has greater stability than one containing a native GC pair because the $R^2$ group provides an additional point for hydrogen bonding to the complementary guanine base. Thus, these embodiments serve as cytosine surrogates for supplemented Watson-Crick base-pairing. In general, a base-pairing substituent Z is defined functionally as any group that, when taken together with the remainder of $R^2$, is capable of increasing the temperature of melting of any of the oligonucleotides 3–9 in Table 1 by at least about 2 degrees Centigrade when substituted as shown in Table 1.

If $R^2$ does not contain a substituent that is capable of contributing to base pairing or hydrogen bonding then $R^2$ is useful at least as a point of attachment for a detectable label. Such Z groups need only be reactive with a bifunctional cross-linking agent or with the label directly. In some embodiments, the polycyclic substructure is itself fluorescent, and in these cases it is not necessary to link the Z group to a detectable label. In these embodiments the polycyclic substructure is detectable by fluorescent emissions, or by adsorption and energy transfer to an emitting (second) label present on a binding partner in the same fashion as is used in EMIT technologies well-known in the diagnostics field.

Spacer A is substituted with from 1 to 3 Z groups. When Z is a base-pairing hydrogen bonding group then "X1" is preferably 1 or 2, ordinarily 1. Similarly, for reasons of steric access it is preferred that only 1 or 2 Z groups are present on spacer A when $R^2$ is intended to function as a label bonding site.

In some embodiments the spacer group A and the Z substituent(s) will interact functionally, i.e., changes in group A may have an impact on the physical or chemical properties of Z, and vice-versa. For example, it will be understood by those skilled in the art that changes can be introduced in spacer A that would reduce or increase the ability of Z to hydrogen bond or to react with a label or cross-linking agent. A readily apparent instance of this would be substitution of A with electron donors or acceptors proximal to a Z group, which may affect hydrogen bonding between Z and guanine. However, it is conceptually useful to consider these domains to be functionally and structurally discrete taking into account interdomain interactions that would be apparent to the ordinary artisan.

Spacer A typically contains a backbone chain of 2, 3, 4, 5, 6, 7, 8, 9, 10, 11, 12, 13, 14, 15 or 16 carbon atoms, any 1, 2 or 3 of which are optionally replaced with N, O or S atoms, usually 1 N, O or S atom. The backbone chain refers to the atoms that connect the Z group(s) to the ring carbon atom at the $R^2$ binding site on the polycycle. The number of spacer backbone atoms does not include terminal Z group atoms. $R^2$ does not include protected amine as described in U.S. Pat. No. 5,502,177.

The spacer A backbone is linear or one or more backbone atoms are substituted, which results in branching. Ordinarily, when 1 Z group is present then A will contain a linear backbone of 2 to 8, usually 2 to 4 atoms. The backbone generally is carbon only, bonded by saturated or unsaturated bonds. If unsaturated bonds are present, the backbone generally will contain 1 to 2 double or triple bonds. Preferably, the backbone is saturated. If a heteroatom is present in the backbone it typically will be O or S. Preferably the heteroatom is O, and preferably only 1 O is present in the backbone chain. Heteroatoms are used to replace any of the backbone carbon atoms, but preferably are used to replace the carbon atom alpha (adjacent) to the polycyclic ring. Usually the atom in the spacer chain that is bonded to the polycyclic substructure is unsubstituted, e.g., —O—, —S—, —NH— or —CH$_2$—, and, in general, the next 1, 2 or 3 atoms in the spacer are unsubstituted carbon.

The spacer A backbone is optionally substituted independently with 1, 2 or 3 of the following: $C_1$–$C_8$ alkyl, —OR$^5$, =O, —NO$_2$, —N$_3$, —COOR$^5$, —N(R$^5$)$_2$, or —CN groups, $C_1$–$C_8$ alkyl substituted with —OH, =O, —NO$_2$, —N$_3$, —COOR$^5$, —N(R$^5$)$_2$, or —CN groups, or any of the foregoing in which —CH$_2$— is replaced with —O—, —NH— or —N(C$_1$–C$_8$ alkyl), wherein R$^5$ is H or a protecting group. Certain of these groups may function as Z sites for linking to detectable labels, but need not be used for that purpose unless desired. In some embodiments these substituents are useful in increasing the lipophilicity of the compounds of this invention.

Group Z detectable labels include all of the conventional assayable substances used heretofore in labeling oligonucleotides or proteins. Examples are well known and include fluorescent moieties such as fluorescein, chemiluminescent substances, radioisotopes, chromogens, or enzymes such as horseradish peroxidase. For the purposes herein, the residue of any bifunctional or multifunctional agent used to crosslink the Z group(s) to the A backbone is defined to be part of the Z group, and the residue of the detectable label is considered also to represent part of Z.

Group Z also encompasses substituents that are not detectable by conventional diagnostic means used in clinical chemistry settings (e.g., UV or visible light absorption or emission, scintillation or gamma counting, or the like) but which are nonetheless capable of reacting with a crosslinking agent or a detectable label to form a covalent bond. In this regard, the Z groups function as intermediates in the synthesis of the labelled reagent. Typical Z groups useful for this purpose include —NH$_2$, —CHO, —SH, —CO$_2$Y or OY, where Y is H, 2-hydroxypyridine, N-hydroxysuccinimide, p-nitrophenyl, acylimidazole, maleimide, trifluoroacetate, an imido, a sulfonate, an imine 1,2-cyclohexanedione, glyoxal or an alpha-halo ketone. Suitable spacers, reactive groups and detectable labels have been described, e.g., U.S. Pat. Nos. 5,668,266, 5,659,022, 5,646,261, 5,629,153, 5,525,465 and 5,260,433, WO 88/10264, WO 97/31008, EP 063 879 B1, Urdea "NAR" 16:4937–4956 (1988), Prober "Science" 238:336–341 (1987).

Z also is a hydrogen bond donor moiety or a moiety, when taken together with the influence of spacer A, has a net positive charge of at least about +0.5 at pH 6–8 in aqueous solutions. Such Z groups are designated $R^{2D}$. In these embodiments, $R^{2D}$ is covalently linked to a short spacer A having a backbone (otherwise described above) of 2, 3, 4, 5 or 6 atoms, designated $R^{2C}$.

The $R^{2C}$ short spacer chain backbone atoms are C atoms and optionally one or two atoms independently selected from the group consisting of O, N or S atoms. $R^{2C}$ short spacer chain backbones include unbranched and branched alkyl that optionally contain one or two independently selected O, N or S atoms. Usually $R^{2C}$ is unbranched, i.e. the backbone has no hydrocarbon substituents. Any branching, if present, will usually consist of a $C_1$–$C_3$ alkyl group, usually a methyl or ethyl group, or $C_1$–$C_3$ alkyl substituted with —OH, =O, —O($C_1$–$C_3$ alkyl), —CN, N$_3$ or 1, 2, 3 or 4 halogen atoms.

Exemplary —$R^{2C}$—$R^{2D}$ and related structures are
(a) —R$^6$—(CH$_2$)$_t$—NR$^5$C(NR$^5$)(NR$^3$)$_2$, including —O—(CH$_2$)$_t$—NR$^5$C(NR$^5$)(NR$^3$)$_2$, —NH—(CH$_2$)$_t$—NR$^5$C(NR$^5$)(NR$^3$)$_2$ and —(CH$_2$)$_{2-5}$NR$^5$C(NR$^5$)(NR$^3$)$_2$,
(b) —R$^6$—CH$_2$—CHR$^{31}$—N(R$^3$)$_2$, —R$^6$—(R$^7$)$_y$—N(R$^3$)$_2$, —R$^6$—(CH$_2$)$_t$N(R$^3$)$_2$, —(CH$_2$)$_t$N(R$^3$)$_2$, —CH$_2$—O—(CH$_2$)$_t$—N(R$^3$)$_2$,

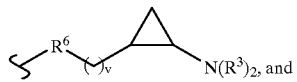

(40)

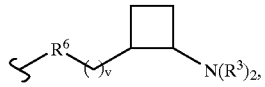

(41)

where R$^6$ is usually —O—,

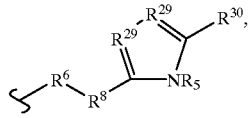

(42)

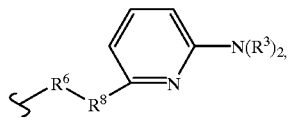

(43)

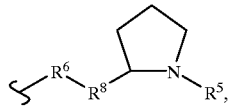

(44)

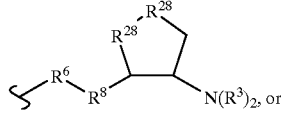

(45)

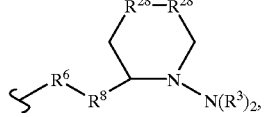

(46)

where R$^6$ is usually —O— and R$^8$ is usually —CH$_2$— or —CH$_2$CH$_2$— in structures (42)–(46) and adjacent R$^6$ and R$^8$ are not —O—O—, —O—S— or —S—S—;

$R^3$ is independently —H, —$CH_3$, —$CH_2CH_3$, —$(CH_2)_w$—$N(R^{33})_2$ or a protecting group, usually —H or —$CH_3$, or, both $R^3$ together are joined to form a protecting group, or, when $R^2$ is —$R^6(CH_2)_tN(R^3)_2$, one $R^3$ is H, $CH_3$, $CH_2CH_3$, a protecting group or —$(CH_2)_w$—$N(R^{33})_2$ and the other $R^3$ is —H, —$CH_3$, —$CH_2CH_3$, —$(CH_2)_w$—$N(R^{33})_2$, —$CH(N[R^{33}]_2)$—$N(R^{33})_2$,

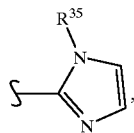  (48)

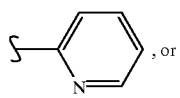, or  (49)

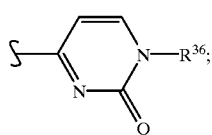;  (50)

usually when one $R^3$ is —H, —$CH_3$, —$CH_2CH_3$, or —$(CH_2)_v$—$N(R^{33})_2$, the other $R^3$ is —H or a protecting group;

$R^5$ is independently —H or a protecting group;

$R^6$ is independently —S—, —$NR^5$—, —O— or —$CH_2$—;

$R^7$ is independently linear alkyl having 1, 2, 3 or 4 carbon atoms, linear alkyl having 2, 3 or 4 carbon atoms and containing one —CH=CH—, —C≡C— or —$CH_2$—O—$CH_2$— moiety, or $R^7$ is cyclic alkyl having 3, 4 or 5 carbon atoms, wherein one of the linear alkyl carbon atoms is optionally substituted with a single —$CH_3$, —CN, =O, —OH or protected hydroxyl, provided that the carbon atoms in any —CH=CH— or —$CH_2$—O—$CH_2$— moiety are not substituted with =O, —OH or protected hydroxyl, and usually $R^7$ is —$CH_2$—, —$CH_2$—$CH_2$—, —$CH_2$—$CH_2$—$CH_2$— or —$CH_2$—$CH_2$—$CH_2$—$CH_2$—;

$R^8$ is linear alkyl having 1 or 2 carbon atoms wherein one of the linear alkylene carbon atoms is optionally substituted with a single —$CH_3$, —CN, =O, —OH or protected hydroxyl, or $R^8$ is absent and $R^6$ is linked directly to the ring in $R^2$ structures (42)–(46), usually $R^8$ is —$CH_2$— or —$CH_2$—$CH_2$—;

$R^{28}$ is independently —$CH_2$—, —$CH(CH_3)$—, —CH($OCH_3$)—, —$CH(OR^5)$— or —O—, but both are not —O—;

$R^{29}$ is independently —N—, —$N(CH_3)$—, —CH—, —$C(CH_3)$—, but both are not —$N(CH_3)$—;

$R^{30}$ is —H or —$N(R^3)_2$, usually —H or —$NH_2$;

$R^{31}$ is the side chain of an amino acid, usually the side chain of a naturally occurring amino acid, e.g. glycine, alanine, valine, isovaline, leucine, threonine, serine, lysine or arginine;

$R^{33}$ is independently —H, —$CH_3$, —$CH_2CH_3$ or a protecting group;

$R^{35}$ is H, $C_1$–$C_4$ alkyl (including —$CH_3$, —$CH_2CH_3$) or a protecting group, usually —H or a protecting group;

$R^{36}$ is —H, —$CH_3$, —$CH_2CH_3$, a protecting group, a monosaccharide, where the monosaccharide is usually linked at the monosaccharide's 1' position and where any monosaccharide hydroxyl groups are optionally protected, typically an $R^{36}$ monosaccharide is 2'-deoxyribose, a 2'-deoxy-2'-$R^{21}$-substituted ribose or arabinose such as 2'-deoxy-2'-fluororibose or 2'-deoxy-2'-fluoroarabinose, or the monosaccharide is ribose or arabinose;

t is 1, 2, 3 or 4, but when $R^6$ is —O—, —S— or —$NR^5$—, t is 2,3 or 4;

v is independently 0, 1 or 2; and w is 1 or 2.

Invention embodiments include $R^2$ moieties having the structure —$R^{59}$—$NH_2$ where $R^{59}$ has the structure —$R^6$—$R^{60}$—, including —$R^6$—$(CH_2)_t$—$N(R_3)_2$, where $R^6$ is usually —O—, —S—, —NH— or —$CH_2$—, $R^{60}$ is —$CHR^{51}$—$(CHR^{51})_{Z3}$—$(R^{61})_{Z1}$—$(CHR^{51})_{Z2}$—$CHR^{51}$— where $R^{61}$ is —O—, —S—, C(O), —$CHR^5$ or —$NR^5$— and usually 0, 1 or 2 $R^{51}$ are methyl or ethyl; $R^{51}$ independently is —H, methyl or ethyl; Z3 is 1, 2 or 3, usually 1; Z1 is 0 or 1, usually 0; and Z2 is 1, 2 or 3, usually 1. In these embodiments, any functional groups, e.g., —OH, —$NH_2$, —COOH, or —SH, that are optionally present at $R^{21}$ are usually protected. These embodiments are useful as intermediates useful to make monomers for oligonucleotide synthesis.

Other invention embodiments include $R^2$ moieties having the structure

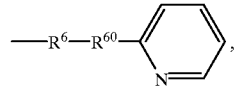, including 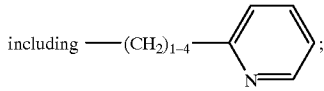;

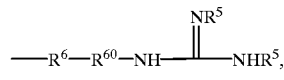, including 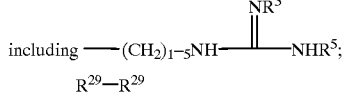;

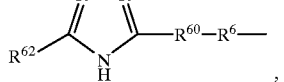, including 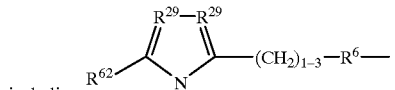;

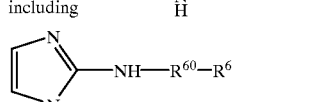, including

; and

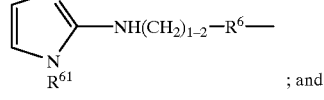, including

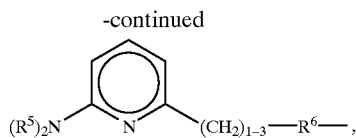

where $R^{61}$ is —H, alkyl having 1, 2, 3 or 4 carbon atoms or optionally protected substituted alkyl having 1, 2, 3, 4, 5 or 6 carbon atoms including —CH$_3$ and —CH$_2$CH$_3$, and $R^{62}$ is —H, —NH$_2$ or —NH(CH$_3$). Other embodiments are —R$^6$—(CH$_2$)$_{2-8}$—NH$_2$, —R$^6$—(CH$_2$)$_{2-8}$—OR$^5$ or —R$^6$—(CH$_2$)$_{2-8}$—CO$_2$R$^{5A}$.

Compounds of Structure (1)—Substituent $R^1$—Linker

One uses $R^1$ linker groups to covalently bond the invention base to the selected binding partner, although it will be understood that this need not be the sole use for the linker functionality. Thus, a group present in $R^1$ linkers principally serves as the site for covalently bonding the invention base to a binding partner, typically by incorporating the invention base via the linker residue into a polymeric binding partner by grafting or copolymerization.

$R^1$ linkers also optionally are substituted with groups that ordinarily will not participate in binding to the binding partner, e.g., halo, azido and protected hydroxyl. Generally, such linker groups will contain from 2 to about 50 atoms. If it contains a cycle the cyclic functionality typically will be an oxygen, sulfur or phosphorus-containing saturated or unsaturated heterocycle having a total of about from 5 to 7 ring atoms and 1 to 3 heteroatoms. For the most part, the cycle will be a monosaccharide, typically (i) a hexose, (ii) a hexose such as glucose substituted with phosphate, protected phosphate, hydrogen phosphonate, a phosphoramidate, hydroxyl or protected hydroxyl, (iii) a furanose or (iv) a furanose substituted with phosphate, protected phosphate, hydrogen phosphonate, a phosphoramidate, hydroxyl or protected hydroxyl. Typical furanose sugars include ribose, 2'-deoxyribose, 2'-deoxy-2'-$R^{21}$-substituted ribose and their 2' ara isomers. Ordinarily, $R^1$ is an abasic nucleotide residue or such a residue derivatized so as to be capable of incorporation into an oligonucleotide.

Thus, the $R_1$ linker frequently comprises an activated group or other group which can react with a polymer or other binding partner to be labeled with the polycyclic substructure. For example, groups described below that are compatible with commonly available oligonucleotide synthetic chemistries are useful. Other examples of reactant groups for covalent labeling are well-known from the diagnostic fields and have heretofore been used commonly to label proteins and oligonucleotide probes, as is more fully discussed below.

In one embodiment, $R^1$ is a bifunctional or multifunctional organic linker group such as alkyl, alkene, alkyne, alkoxyalkyl, alkylthioalkyl, alkoxy, saturated or unsaturated heterocycle that is substituted with at least one group capable of being crosslinked with or incorporated into a polymer, e.g., such groups as hydroxy, amino, carboxyl, vinyl, phosphate or phosphonate. U.S. Pat. No. 5,502,177 describes suitable linker groups. An example of such an $R^1$ linker suitable for oligonucleotide synthesis is protected monosaccharides, such as ribofuranose and deoxyribofuranose sugars of structure (5)

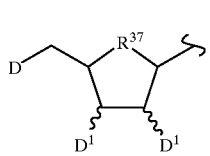

where an invention base is linked to the open valence at the 1' position, D is hydroxyl, protected hydroxyl or is an oligonucleotide coupling group and $D^1$ is independently $R^{21}$ or an oligonucleotide coupling group, but both $D^1$ are not coupling groups.

In embodiments of the invention where the compound of structure (1) is to be used as a monomer in the preparation of oligonucleotides, $R^1$ is typically structure (5) where one $D^1$ is an oligonucleotide coupling group and D is —OH or protected hydroxyl.

"Coupling group" as used herein means any group suitable for generating a phosphodiester linkage or phosphodiester substitute linkage between nucleotide bases or their analogs. These coupling groups are conventional and well-known for the preparation of oligonucleotides, and are prepared and used in the same fashion here. They are usually configured as the b anomers as denoted in structure (5) or optionally as the alpha anomers. In general, each compound comprising structure (5) will contain two coupling groups: D or $D^1$, but with only one $D^1$ being a coupling group. The coupling groups are used as intermediates in the preparation of 3',5' 5',3', 5',2' and 2',5' internucleotide linkages in accord with known methods.

Suitable coupling groups for phosphodiester linkages or phosphodiester substitute linkages containing phosphorus include OH, H-phosphonate; (for amidite chemistries) alkylphosphonamidites or phosphoramidites such as β-cyanoethylphosphoramidite, N,N-diisopropylamino-β-cyanoethoxyphosphine, N,N-diisopropylamino-methoxyphosphine, N,N-diethylamino-methoxyphosphine, N,N-diethylamino-β-cyanoethoxyphosphine, N-morpholino-β-cyanoethoxyphosphine, N-morpholino methoxyphosphine, bismorpholino-phosphine, N,N-dimethylamino-β-cyanoethylmercapto-phosphine, N,N-dimethylamino-2,4-dichlorobenzylmercaptophosphine, and bis(N,N-diisopropylamino)-phosphine; and (for triester chemistries) 2-, or 4-chlorophenyl phosphate, 2,4-dichlorophenyl phosphate, or 2,4-dibromophenyl phosphate. See for example U.S. Pat. Nos. 4,725,677; 4,973,679; 4,997,927; 4,415,732; 4,458,066; 5,047,524; 4,959,463; 5,624,621; and International Publication Nos. WO 97/14706 and WO 92/07864.

For structure (2) embodiments, if $D^1$ is a coupling group then D typically will be hydroxyl protected with a group suitable for ensuring that the monomer is added to the oligonucleotide rather than dimerizing. Such groups are well known and include DMT, MMT, FMOC (9-fluorenylmethoxycarbonyl), PAC (phenoxyacetyl), a trialkyl (C$_1$–C$_6$ alkyl, each alkyl group is independently chosen) silyl ether or an alkyl (C$_1$–C$_6$ alkyl) diaryl (e.g., phenyl) silyl ether such as TBDMS (t-butyldiphenylsilyl) and TMS (trimethylsilyl). The opposite will apply when one desires to synthesize an oligonucleotide in the opposite direction (5'→3'). Ordinarily in structure (5) compounds, D is DMT, $D^1$ is located on the 3' carbon, $R^{21}$ is H and the $D^1$ and $R^{21}$ groups are in the alpha anomer conformation.

As noted above, $R^1$ includes an optionally protected monosaccharides of structure (4) and (4A). Usually the monosaccharides in structure (4) and (4A) compounds are 2'-deoxyribose, 2'-deoxy-2'-$R^{21}$-substituted ribose, 2'-deoxy-2'-$R^{21}$-substituted arabinose, ribose or arabinose, any of which are optionally protected at sugar all or some hydroxyls or at optionally present $R^{21}$ functional groups such as —OH —SH or —NH$_2$ groups.

Invention embodiments include compositions of the formula

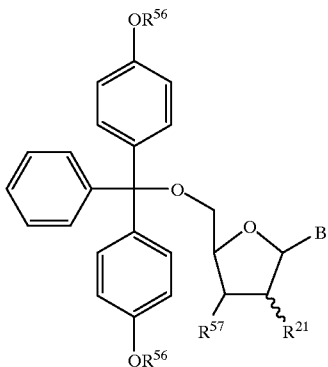

where B is a structure (3), (4) or (4A) base, $R^{56}$ is a diene or a dieneophile, both as defined in WO 97/14706, $R^{57}$ is —$OR^5$, a coupling group including —OH, H-phosphonate, a phosphoramidite or an optionally protected oligonucleotide having a 3'-terminal group selected from a coupling group and —$OR^5$ and any reactive moiety in $R^{21}$ is optionally protected. $R^{56}$ dienes are independently chosen and include 2,4-hexadiene and 3,5-hexadiene. One or both $R^{56}$ are linked to a solid support such as a crosslinked organic polymer, polystyrene, Tentagel™, polyethylene glycol or an inorganic oxide such as silica gel, alumina, controlled pore glass or a zeolite. These compositions are useful for making oligonucleotides containing one or more invention bases.

Invention embodiments include compositions and their isomers of the formula

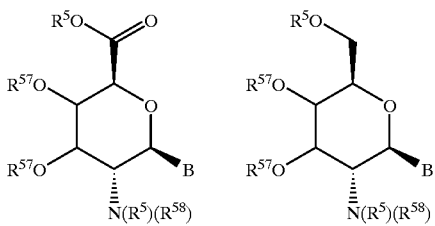

where $R^{57}$ is independently —H, a protecting group or both $R^{57}$ together are a dihydroxy protecting group, $R^{58}$ is —H or alkyl containing 1, 2, 3 or 4 carbon atoms and B is a structure (3), (4) or (4A) base. Suitable $R^5$ at the nitrogen atom include —H, FMOC and tBOC (t-butyloxycarbonyl) and suitable $R^5$ at the carboxyl group include —H, t-butyl and benzyl, see, e.g., WO 97/14709. These compositions are useful for making oligonucleotides containing one or more invention bases.

Protecting groups suitable for use with amine groups that may be present at $R^2$ include FMOC and trichloroacetamide. Monomers and polymers may contain such protecting groups at $R^2$.

Substituent $R^1$—Binding Partner $R^1$, when functioning as a binding partner, is a substance that non-covalently binds to a target compound. Generally, the target compound is an analyte whose presence is desired to be detected. Binding partners are well-known from the immunoassay art and include hapten-antibody pairs such as those used in drug immunoassays using EMIT or ELISA technologies. Binding partners are employed analytically in enzymology, where the substrate or the enzyme is labeled. Binding partners also are known from the oligonucleotide hybridization art, including oligonucleotide-nucleic acid binding partners (as in diagnostic probes or therapeutic antisense oligonucleotides) or oligonucleotide-protein binding partners (aptamers). In accordance with this invention, an invention base is substituted at $R^1$ by any binding partner. While the binding partner may be a small molecule such as a drug, hapten, substrate or the like, ordinarily it is a polymer.

Compounds of structure (1) wherein $R^1$ is a polymer are an important feature of this invention. For the most part, when $R^1$ is a polymer an $R^1$ linker group has been subsumed into the polymer structure, either as a monomer unit or by grafting onto pre-existing polymer. Therefore, when $R^1$ is a polymer, the polymer may comprise the residue of a linking group derived from a monomer or where the linking group differs from the polymer's monomeric subunits. The invention base must be covalently linked to the polymer.

The nature of the polymer is not critical. Typical $R^1$ polymers include a biopolymer such as an oligonucleotide, a protein (including antibodies, enzymes, cell membrane proteins, glycoproteins, glycolipids, lipoproteins and nucleoproteins), a peptide, a nucleic acid, or a glycan or other polysaccharide or carbohydrate. In certain embodiments the polymer is an oligonucleotide in which either or both of the sugar or phosphodiester monomer subunits are substituted by groups that continue to permit base pairing by the invention base analogs but which have other desirable characteristics that are not shared with native substituents, e.g., those which mask the negative charges of the phosphodiester linkages or replace the phosphodiester linkage with another group.

The site at which one links the invention base analogs to a polymer is typically not critical. In general, any reactive group on the polymer is satisfactory when one wants to graft the polycycle-$R^2$ substructure onto a pre-existing polymer. Obviously, the site of the substitution should not be in a location in which the polycycle-$R^2$ substructure will interfere with the intended function for the polymer, e.g. enzyme active site, antibody CDR, and the like as will be understood by the artisan. An amino acid side chain such as that of lysine, glutamic acid, serine, asparagine and the like will be satisfactory for grafting to protein $R^1$, as will alpha amino groups, provided that the amino acids in question do not participate in the binding partner or ligand/substrate interaction involved in the assay in which the labeled protein is to be used. One applies the same reasoning to select a binding site or sites on other analytes such as sugars, glycans, lipids, and the like. For example, the 1' position of ribose or deoxyribose is satisfactory as the site of substitution of an oligonucleotide by the invention base analogs. Suitable sites will be known to the artisan, particularly in those instances where the one intends to substitute an invention base analog for purine or pyrimidine bases, usually for cytosine, or for fluorescent labels.

The degree of polymer substitution by the invention base analogs is not critical. One skilled in the art will choose the reaction conditions such that the resulting labeled polymer will be substituted with sufficient molar proportion of base analog to facilitate its use in the desired analytical, therapeutic or preparative procedure. This is accomplished by preparing the labeled polymers under a variety of conventional conditions, e.g., the time, temperature or duration of the labeling reaction, to yield a matrix of multiply-labeled polymers. These then are screened for suitability in the intended application. Molar ratios of about from 1:1 to 10:1 invention base to polymer generally are suitable. Where the labeled polymer is prepared by monomer incorporation, the resulting polymer may contain about from 1% to 100% invention base analog substitution. In this embodiment each invention base is considered a monomer unit (even though the polymer may have been assembled from intermediate synthons containing 2 or more invention bases per synthon).

Oligonucleotides are polymers containing at least 2 covalently linked nucleotides or nucleotide analogs (collectively monomers), at least one of which comprises an invention base. In oligonucleotide invention embodiments at least one invention base is covalently linked to a nucleotide sugar, and typical invention oligonucleotides will contain about 2–75% of the bases as invention base analogs, usually about 5–25%. Small oligonucleotides, e.g., 2–6-mers, that serve as synthetic intermediates for larger oligonucleofides will optionally contain the higher proportions of invention base analogs, e.g., about 50–75%. Larger oligonucleotides, e.g., about 7–21-mers, will generally contain 1, 2, 3, or 4 invention bases, occasionally 5 and usually not more than about 5 invention bases, unless the oligonucleotide is relatively long, e.g., about 22–50-mer.

Invention embodiments include polymers and oligonucleotides where the invention bases are located on 2, 3 or more adjacent monomers or nucleotide residues, or the invention bases may be located on monomers or nucleotide residues that are separated from each other by about 1, 2, 3, 4, 6, 8, 10, 12, 15, 18 or more monomers or nucleotide residues that do not contain these bases. When a detectable label is linked to an invention base at $R^2$, the oligonucleotide may contain 1, 2 or 3 of these labeled monomers, usually 1 or 2. Such labelled monomers are often located at the 3' or 5' terminus, but they may reside at an internal position such as one, two or more monomer residues from either terminus.

Invention oligonucleotides, which contain 1, 2, 3 or more invention bases, will typically have sufficient binding affinity for complementary nucleic acid sequences to allow facile detection of the duplex or triplex resulting from the base sequence-specific binding interaction. Typically, an invention oligonucleotide will have a Tm of at least about 15° C., usually at least about 20° C., when tested under typical in vitro binding conditions, such as those described herein and elsewhere, (Jones, "J Org Chem" [hereafter "JOC" ] 58:2983–91 1993, Froehler, "Tet. Lett." 34:1003–06 1993). Complementary nucleic acid means a natural or synthetic compound that is capable of forming a hydrogen bonded complex in a sequence-specific manner with an invention oligonucleotide such as a structure (2) oligonucleotide. Complementary nucleic acid base sequences contain no mismatches, while "substantially complementary" base sequences contain only a limited number of mismatches, e.g., at most about 1 mismatch per about 15–20 bases, relative to an invention oligonucleotide.

One optionally measures the binding of an invention oligonucleotide to a complementary nucleic acid by detecting or measuring a Tm, by detecting the presence of a label present on the invention oligonucleotide or on the complementary nucleic acid (after separating bound invention oligonucleotide from unbound invention oligonucleotide), by amplifying nucleic acids containing a region(s) complementary to an invention oligonucleotide and so forth. Because of this, invention oligonucleotides optionally include species containing one or more modifications that decrease binding affinity, while the oligonucleotide still retains sufficient binding affinity for a given application. In addition, embodiments include short oligonucleotides or oligonucleotide domains, e.g., having about 2, 3, 4, 5 or 6 linked monomers, where the domain may have low binding affinity, but even in this case are useful as intermediates to make longer oligonucleotides so as to increase affinity sufficiently to confer a Tm of at least about 15° C. Generally, invention oligonucleotide analogs will contain about 40% or less, usually about 25% or less, of monomers that significantly reduce binding affinity, i.e., monomers that decrease the Tm more than about 2° C. per monomer, compared to a corresponding unmodified oligonucleotide.

Invention embodiments include protected, partially protected and deprotected monomers and polymers including oligonucleotides. Partially protected compounds arise during the course of deprotection and they are thus intermediates in the process of preparing deprotected compounds. Typically, one would not recover partially deprotected compounds. Deprotected compounds have been subject to a treatment that removes the protecting group(s), although the preparation may contain some compounds with unremoved protecting groups. Typically, any remaining protecting groups that remain after deprotection are present in small amounts that may be removed by suitable purification methods if desired.

Invention embodiments include oligonucleotides of structure (2) where $R^{37}$ is oxygen. Invention oligonucleotides, including those where $R^{37}$ is oxygen, typically contain 2, 3, 4, 5, 6, 7, 8, 9, 10, 11, 12, 13, 14, 15, 16, 17, 18, 19, 20, 21, 22, 23 or 24 linked monomers usually about 5–21. Such oligonucleotides optionally contain about 30–100%, typically about 60–100%, of the linkages as phosphodiester or phosphorothioate linkages, or other linkages of similar binding affinity.

Invention oligonucleotides include support-bound oligonucleotides, which are typically used in solid phase synthesis and separation applications. Support-bound oligonucleotides are typically protected during synthesis, e.g., bases, sugar hydroxyls, linkages and functional groups optionally present are protected as needed, e.g., a sugar hydroxyl group present at $R^1$, an amine group at $R^2$ or a hydroxyl or amine group at $R^{21}$. In these embodiments, $R^1$ is covalently linked to a solid support or $R^1$ is an oligonucleotide linked to a solid support. When one removes invention oligonucleotides from a support, the protecting groups are generally removed at the same time or shortly thereafter.

Invention embodiments include highly lipophilic polymers and oligonucleotides that comprise (i) one or more structure (3) bases, usually about 1, 2, 3 or 4, and (ii) lipophilic modifications such that the polymer or oligonucleotide has an octanol:water partition coefficient of about −0.5 to about 2.5, typically about 0.0–2.0, usually about 0.2–1.5, and a solubility in water of at least 0.001 μg/mL, usually at least 0.1 μg/mL.

One can use such highly lipophilic polymers and oligonucleotides as reagents to stain, detect or visualize living cells in vitro or in vivo, as described in U.S. Pat. No. 5,633,360 and in Application No. PCT US 96/12530. These highly lipophilic polymers and oligonucleotides need not be binding competent for cell staining, detecting or visualizing applications and they are optionally labeled using standard labels, e.g., radiolabels ($^{32}$P, $^{35}$S, $^{131}$I, $^{14}$C, $^{3}$H), fluorescent labels such as fluorescein, Texas Red, rhodamine, BODIPY, resorufin or arylsulfonate cyanines and chemiluminescent labels, e.g., acridinium esters.

Embodiments of such optionally labeled highly lipophilic invention oligonucleotides include species where (i) at least about 30%, typically at least about 40%, usually at least about 60% (often at least about 80%), of the internucleotide linkages are non-ionic internucleotide linkages (typically containing a lipophilic moiety at each non-ionic linkage), or (ii) at least about 30%, typically at least about 40% usually at least about 60%, of the bases included in said oligonucleotide contain a lipophilic substitution, (iii) at least about 30%, typically at least about 40% usually at least about 60%, of the sugars, usually at the 2' position, included in said oligonucleotide contain a lipophilic substitution or (iv) the percent non-ionic nucleotide linkage and the percent lipophilic bases and the percent lipophilic sugars sum to at least about 30%, typically at least about 40% usually at least about 60% (or at least about 80%).

Usually, the invention base analogs and other noninvention bases that are present in binding-competent oligonucleotides are linked together by an organic moiety that is sufficiently flexible to permit the invention base analog(s) to hybridize to complementary bases. The linkage may be a conventional phosphodiester linkage in which a nucleotide analog containing a structure (1) compound, where $R^1$ is deoxyribosyl, ribosyl or an analog thereof, which is incorporated into an oligonucleotide by conventional methods. Alternatively, other groups are used to replace the phosphodiester linkage or, in some instances, both of the phosphodiester linkage and the sugar group. These replacement groups are termed "phosphodiester substitute linkages" for the purposes herein.

Phosphodiester substitute linkages are well-known from the prior literature. They include for example phosphorodithioates (Marshal, "Science" 259:1564, 1993), phosphorothioates and alkylphosphonates (U.S. Pat. No. 5,212,295, Kibler-Herzog, "Nucleic Acids Research" [hereafter "NAR"] 19:2979, 1991; PCT 92/01020; EP 288,163; FIG. 12-1), phosphoroamidates (Froehler, "NAR" 16:4831, 1988), 3'-NH phosphoramidates (Schultz, "NAR" 24:2966, 1996; Gryaznov, "J Am Chem Soc" [hereafter "JACS"] 116:3143, 1994; Chen, "NAR" 22:2661, 1995; Gryaznov, "Proc Natl Acad Sci" USA 92:5798, 1995), phosphotriesters (Marcus-Sekura, "NAR" 15:5749, 1987), boranophosphates (Sood, "JACS" 112:9000, 1991), 3'-O-5'-S- phosphorothioates (Mag, "NAR" 19:1437, 1991), 3'-S-5'-O-phosphorothioates (Kyle, Biochemistry 31:3012, 1992), 3'-CH$_2$-5'-O-phosphonates (Heinemann, "NAR" 19:427, 1991), 3'-NH-5'-O-phosphonates (Mag, "Tet. Lett." 33:7323, 1992), sulfonates and sulfonamides (Reynolds, "JOC" 57:2983, 1992), sulfones (Huie, "JOC" 57:4519, 1992), sulfoxides (Huang, "JOC" 56:3869, 1991), sulfides (Schneider, "Tet Lett." 30:335, 1989), sulfamates, ketals and formacetals (Matteucci, "JACS" 113:7767, 1991, PCT 92/03385 and PCT 90/06110), 3'-thioformacetals (Jones, "JOC" 58:2983, 1993), 5'-S-thioethers (Kawai, "Nucleosides Nucleotides" 10:1485, 1991), carbonates (Gait, "J Chem Soc Perkin Trans 1" 1389, 1979), carbamates (Stirchak "JOC" 52:4202, 1987), hydroxylamines (Vasseur, "JACS" 114:4006, 1992), methylamine (methylimines) and methyleneoxy (methylimino) (Debart, "Bioorg Med Chem Lett" 2:1479, 1992) and amino (PCT 91/06855). Also of interest are hydrazino and siloxane (U.S. Pat. No. 5,214,134) linkages, thionotriester linkages (WO 96/29337) and related synthesis methods (WO 97/31009).

Phosphodiester substitute linkages per se also are known for the replacement of the entire phosphoribosyl linkage of conventional oligonucleotides. These include for example morpholino-carbamates (Stirchak, "NAR" 17:6129, 1989), peptides (Nielsen et al., "Science" 254:1497, 1991; U.S. Ser. Nos. 07/892,902 and 07/894, 397), riboacetal linkages (PCT 92/10793) and morpholino-based linkages disclosed in U.S. Pat. Nos. 5,521,063 and 5,185,144.

Additional disclosure of phosphodiester substitute linkages is found in U.S. Pat. No. 5,386,023, U.S. Pat. No. 5,489,677, WO 95/18623, WO 94/00467, WO 93/08296, WO 92/20822, WO 92/20823, PCT 91/08213, 90/15065, 91/15500, 92/20702, 92/20822, 92/20823, 89/12060 and 91/03680; Mertes, "J Med Chem" 12:154, 1969; Mungall, "JOC" 42:703, 1977; Wang, "Tet Lett" 32:7385, 1991; Stirchak, "NAR" 17:6129, 1989; Hewitt, "Nucleosides and Nucleotides" 11:1661, 1992; Van Aerschot, "Agnew Chem Int Ed Engl" 34:1338, 1995; and U.S. Pat. Nos. 5,034,506 and 5,142,047.

Invention embodiments include oligonucleotides having 1, 2, 3 or more optionally protected invention bases, 0 to about 30 other optionally protected bases, usually guanosine, adenine, thymine, cytosine or 5-methylcytosine, and at least one modified linkage, e.g., 3' —N($R^{11}$)—O— 5', where $R^{11}$ is hydrogen, $C_{1-6}$ alkyl, usually —CH$_3$ or —C$_2$H$_5$ and the terminal atoms are linked to the 3' and 5' carbons of adjacent ribose or 2'-deoxy-2'-$R^{21}$ substituted ribose sugars, (51)

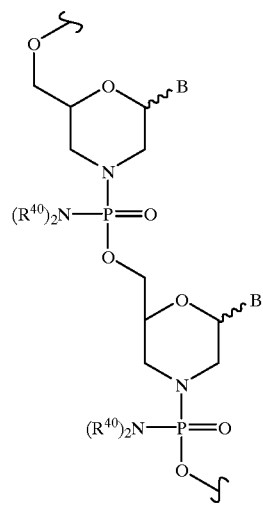

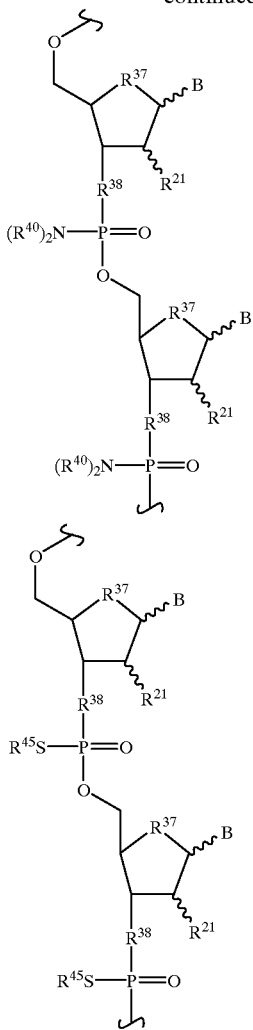

(52)

(53)

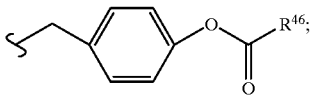

where $R^{38}$ independently is O, $CH_2$ or NH; $R^{40}$ independently is hydrogen, $C_{1-8}$ alkyl (methyl, ethyl, n-propyl, i-propyl, n-butyl, i-butyl, t-butyl, etc.), a protecting group or both $R^{40}$ together with the nitrogen atom to which they are attached form

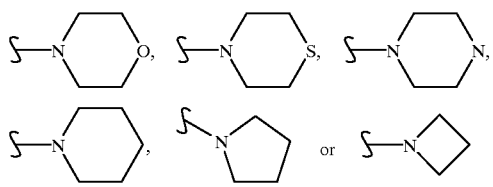

or both $R^{40}$ together are a protecting group, or $R^{40}$ is alkyl ($C_1$–$C_{12}$), usually unbranched or branched once containing 1, 2, 3, 4, 5, 6, 7 or 8 carbon atoms, including methyl, ethyl, n-propyl and isopropyl) or $R^{40}$ is substituted alkyl ($C_1$–$C_{12}$, usually unbranched or branched once containing 1, 2, 3, 4, 5, 6, 7 or 8 carbon atoms, with substituents including one, two or more —O—, —C(O)—, —OC(O)—, —C(O)O—, —$OR^{42}$, —$SR^{43}$, —C(O)$NR^{39}$—, —C(O)N($R^{41}$)$_2$, —$NR^{41}$—, —N($R^{41}$)$_2$, halo (e.g., —F, —Cl), —CN, —$NO_2$ moieties); $R^{41}$ independently is hydrogen, a protecting group (or both $R^{41}$ together are a protecting group), alkyl ($C_1$–$C_4$ including methyl, ethyl and n-propyl); $R^{42}$ is hydrogen or a protecting group; $R^{43}$ is $C_{1-6}$ alkyl or a protecting group; and $R^{45}$ is —H, a counter ion or a hydrolyzable moiety such as $R^{46}$ is alkyl containing 1, 2, 3, 4, 5, 6, 7 or 8 carbon atoms. $R^{40}$ pairs include ones where one $R^{40}$ is hydrogen and the other $R^{40}$ is alkyl containing 1, 2, 3, 4, 5 or 6 carbon atoms or substituted alkyl containing 1, 2, 3, 4, 5, 6, 7 or 8 carbon atoms, including methyl, ethyl, methoxyethyl and ethoxyethyl. When $R^{40}$ is substituted alkyl, it will usually contain 1, 2, 3 or 4 non-carbon atoms, but may contain additional non-carbon atoms, particularly when the non-carbon atoms are halogens or when a group is present as a protecting group, e.g., $R^{39}$, $R^{40}$, $R^{41}$ or $R^{42}$.

Structure (2) and (52) oligonucleotides include species where one or more $R^{21}$ is —F, —O($CH_2$)$_2$$NHR^5$, —O($CH_2$)$_3$$NHR^5$, —O($CH_2$)$_4$$NHR^5$, —O($CH_2$)$_2$$OCH_3$, —O($CH_2$)$_3$$OCH_3$, —O($CH_2$)$_2$$OR^5$, —O($CH_2$)$_2$F, —O($CH_2$)$_3$$OR^5$, or —O($CH_2$)$_3$F (see, e.g., Griffey "J Med Chem" 39:5100–5109 1996, Schultze "Cell" 24:2966–2973 1996). Such oligonucleotides include oligonucleotides where 1, 2, 3, 4, 5, 6, 7, 8 or more monomers are substituted with $R^{21}$, which will optionally comprise one of these substituents and the remaining $R^{21}$ are all hydrogen. Embodiments also include optionally protected monomers containing an optionally protected invention base for synthesis of phosphoramidate-linked oligonucleotides. Oligonucleotides containing one or more of these linkages are optionally prepared as highly lipophilic oligonucleotides and they are suitable for cell staining uses, diagnostic uses and for antisense applications that optionally rely at least in part on an RNase H mechanism.

Invention embodiments include oligonucleotides or monomers described in U.S. Pat. Nos. 5,670,489, 5,667,976, 5,652,355, 5,652,356 and 5,212,295 where one or more optionally protected invention bases is present, usually 1, 2, 3 or 4.

Invention embodiments include oligonucleotides having 1, 2, 3 or more optionally protected invention bases, 0 to about 30 other bases (optionally protected) and at least one amide linkage, e.g., a compound of structure (2B) where n is 0 to about 50, usually about 5–21. Such amide linkages have been described, e.g., (Haaima "Agnew Chem Int Ed Engl" 35:1939–1942 1996; Nielsen "Bioconjugate Chem" 5:3–7 1994). Other amide linkages that are suitable have been described, e.g., WO 92/20702 and WO 93/24507. Embodiments also include optionally protected monomers containing an optionally protected invention base for synthesis of amide-linked oligonucleotides. In general, structure (2B) oligonucleotides will contain only amide linkages, but they may also comprise a domain of monomers linked by non-amide linkages. Suitable $D^2$ and $D^3$ have been described, e.g., WO 86/05518, WO 92/20702, WO 93/24507. $D^2$ optionally comprises a peptide coupling group, a protecting group, or a solid support. $D^3$ optionally comprises —H, a peptide coupling group, a protecting group, or a solid support, but $D^2$ and $D^3$ are not both a peptide coupling group or a solid support. WO 92/20702 described activated derivatives of —$CO_2$H and —$SO_3$H.

The phosphodiester or phosphodiester substitute linkages herein are used to bond the 2' or 3' carbon atoms of ribose or ribose analogs to the 5' carbon atoms of the adjacent ribose or ribose analog. Ordinarily, the linkages in oligonucleotides are used to bond the 3' atom of the 5' terminal oligonucleotide to the 5' carbon atom of the next 3'-adjacent nucleotide or its analog. In general, linkages that contain a phosphorus atom will be 3',5' linkages and not 2',5' linkages because such linkages usually confer reduced binding affinity on the oligonucleotide in which they are present.

Table 1 of U.S. Pat. No. 5,502,177 describes examples of suitable phosphodiester substitute linkages for use with the invention base analogs. The starting materials in Table 1, or those used to prepare the starting materials of Table 1, generally possess structure (1) in which $R^1$ is ribose, 2'-deoxyribose, a ribose analog or a 2'-deoxyribose analog comprising a 5' hydroxyl group and a 3' or 2' hydroxyl group, prepared as described herein or in the citations, with an invention base analog(s) being substituted for the bases used in the citations. The reactions are repeated or ganged with phosphodiester or other linkages in order to produce trimers, tetramers, pentamers or larger oligonucleotides, including ones up to about 100 bases.

The oligonucleotides of this invention contain naturally occurring nucleotides or derivatives thereof. In some oligonucleotide embodiments the companion nucleotide residues contain pyrimidine nucleotides substituted at the 5 position with a carbon atom which is distally Pi bonded to another atom as for instance 1-alkenyl, 1-alkynyl, heteroaromatic and 1-alkynyl-heteroaromatic groups such as 5-(1-propynyl)-cytosine and -uridine nucleotides (see PCT Publication No. WO 93/10820 and U.S. Pat. No. 5,594,121). Other analogs of native bases for use herein include alkylated purines or pyrimidines, acylated purines or pyrimidines, or other analogs of purine or pyrimidine bases and their aza and deaza analogs. These include, for example $N^4,N^4$-ethanocytosine, 7-deazaxanthosine, 7-deazaguanosine, 8-oxo-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, inosine, $N^6$-isopentenyl-adenine, 1-methyladenine, 2-methylguanine, 5-methylcytosine, $N^6$-methyladenine, 7-methylguanine, 5-methylaminomethyl uracil, 5-methoxy aminomethyl-2-thiouracil, 5-methoxyuracil, pseudouracil, 5-methyl-2-thiouracil, 2-thiouracil, 4-thiouracil, 5-(1-propynyl)-4-thiouracil, 5-(1-propynyl)-2-thiouracil, 5-(1-propynyl)-2-thiocytosine, 2-thiothymidine, and 2,6-diaminopurine. In addition to these base analogs, one can conveniently incorporate into the invention oligonucleotides other base analogs, including pyrimidine analogs including 6-azacytosine, 6-azathymidine, 5-trifluoromethyluracil or other bases previously described, see, e.g., bases, monomers or oligonucleotides described in WO 92/02258, WO 97/32888 and U.S. Pat. No. 5,614,617.

Preferred bases include adenine, guanine, thymine, uracil, cytosine, 5-methylcytosine, 5-(1-propynyl)uracil, 5-(1-propynyl)cytosine and 5-(1-butynyl)uracil, 5-(1-butynyl) cytosine.

Invention embodiments include the protected derivatives of native bases, their analogs and optionally protected monomer synthons containing such bases, which one would typically use as intermediates to prepare invention oligonucleotides (see, e.g., International Publication No. WO 96/37504, U.S. Pat. No. 5,614,622 Iyer et al., "Nucleosides & Nucleotides", 14:1349–57, 1995, Uhlmann et al., "Chem Revs", 90:543–587, 1990, S. Agrawal, Ed. *Methods in Molecular Biology*, Vol. 20, Protocols for Oligonucleotides and Analogs, pp. 165–189, Humana Press, 1993)

Embodiments of the oligonucleotides of the invention comprise a moiety which is capable of effecting at least one covalent bond between the oligonucleotide and a nucleic acid duplex or strand. Multiple covalent bonds can also be formed by providing a multiplicity of such crosslinking moieties. The covalent bond is preferably to a base residue in the target strand, but can also be made with other portions of the target, including the saccharide or phosphodiester. Preferred crosslinking moieties include acylating and alkylating agents, and, in particular, those positioned relative to the sequence specificity-conferring portion so as to permit reaction with the target location in the strand. Exemplary crosslinking moieties are disclosed and claimed in PCT 91/03680. See also Praseuth ("Proc Natl Acad Sci" 8:1349, 1988), Fedorova ("FEBS" 228:273, 1988), Meyer ("JACS" 111:8517, 1989), Lee ("Biochemistry" 27:3197, 1988), Horne ("JACS" 112:2435, 1990), Shaw ("JACS" 113:7765, 1991).

Invention embodiments include monomers and oligonucleotides containing 1, 2, 3 or more invention bases and a 5' hydroxyl group protected with a base labile protecting group, including a dansylethoxycarbonyl group, which has been described, e.g., U.S. Pat. No. 5,631,362. Such embodiments optionally include additional protecting groups.

Invention embodiments include monomers and oligonucleotides containing 1, 2, 3 or more invention bases and an invention base or a non-invention base having an exocyclic nitrogen atom, where the nitrogen atom is protected with a protecting group as previously described, e.g., specification and claims 1, 2, 3, 4, 5, 6, 7 and 8 of U.S. Pat. No. 5,623,068. Such embodiments optionally include additional protecting groups.

Invention embodiments include optionally protected monomers and optionally protected oligonucleotides containing 1, 2, 3 or more invention bases wherein the compositions possess N-branching, which has been described, e.g., U.S. Pat. No. 5,623,049.

Invention embodiments include "hybrid" oligonucleotides, which contain 1, 2, 3 or more invention bases and 2' modifications in one or two regions or domains that comprise adjacent linked monomers, typically about 2–8 linked monomers, usually about 2–3. One domain contains 2' modifications, while hydrogen is linked to the remaining monomers, typically about 4–10 adjacent linked monomers, usually about 6–8. Such oligonucleotides contain at least one domain that is competent to serve as a RNase H substrate and comprises hydrogen at each 2' position and phosphodiester, phosphorothioate or phosphorodithioate 3',5' linkages. The other domain(s) contain a 2' modification(s), such as —O—$(CH_2)_2$F or —O—$(CH_2)_2$—O—$CH_3$, that enhances binding affinity or nuclease stability. The 2'-modified domain(s) is usually not an efficient RNase H substrate. The bases in hybrid oligonucleotides are the typical purines and pyrimidines found in nucleic acids (G, A, T, C or U) or their analogs, which one finds in some oligonucleotide analogs (e.g., U.S. Pat. Nos. 5,484,908, 5,594,121 and 5,502,177, International Publication No. WO 93/10820). Intermediates used to prepare hybrid oligonucleotides will typically contain appropriately protected derivatives of any bases.

Oligonucleotides of inverted polarity also fall within the scope of this invention. "Inverted polarity" means that the oligonucleotide contains tandem sequences which have opposite polarity, i.e., one having polarity 5'→3' followed by another with polarity 3'→5', or vice versa. These sequences thus are joined by linkages which can be thought of as effectively a 3'—3' internucleoside junction (however the linkage is accomplished), or effectively a 5'—5' internucleoside junction. For a further description of suitable methods for making such oligonucleotides see, e.g., WO 93/10820. Compositions of "parallel-stranded DNA" designed to form hairpins secured with AT linkages using either a 3'-3' inversion or a 5'-5' inversion have been synthesized by Van de Sande, "Science" 241:551, 1988. In addition, oligonucleotides which contain 3'-3' linkages have been described (Horne, op cit; and Froehler, "Biochemistry" 31:1603, 1992). These oligonucleotides are useful as binding partners for double stranded nucleic acids to form triple helix (or triplex) complexes as a means for detecting complementary sequences and inhibiting of target gene expression (PCT 89/05769 and 91/09321).

Invention embodiments include polymers such as oligonucleotides containing 1, 2, 3 or more invention bases, where the polymer is a component of a complex or composition useful for transfecting the polymer into a cell in vitro or in vivo. These complexes or compositions are referred to herein as "transfection complexes". Such transfection complexes optionally comprise one or more lipids, e.g., cationic or anionic lipids, as well as other lipophilic compounds such as cholesterol or colipids such as DOPE. The complexes optionally comprise an uncharged or a charged polymer such as polyethylene glycol, polybrene or a peptide, e.g., polylysine. The complexes optionally comprise unilamellar or multilamellar liposomes or vesicles.

As used herein, any compound(s), reagent(s) or treatment that enhances delivery of an invention oligonucleotide into a cell or tissue is a "permeation enhancing agent." Permeation enhancing agents are well known and are usually present as transfection complexes containing oligonucleotides, e.g., unilamellar or multilamellar liposomes or vesicles. One uses permeation enhancing agents to prepare transfection complexes containing invention oligonucleotides. The permeation enhancing agent are used in essentially the same manner as is used to prepared transfection complexes containing nucleic acids, non-invention oligonucleotides or polymers into cells or tissues.

Invention transfection complexes optionally comprise an additional non-invention polymer(s), e.g., a nucleic acid expression vector(s), a therapeutic agent(s) (e.g., amphotericin B) or a peptide(s).

Invention transfection complexes comprising a lipid may be, as defined herein, "large", i.e., complexes having a maximum average dimension of at least about 200 nm in length or diameter, typically having an average length or diameter of about 200–400 nm, occasionally having an average length or diameter of about 400–800 nm. Transfection complexes comprising a lipid may be "small", i.e., complexes having a maximum average dimension of about 15–200 nm in length or diameter, e.g., an average dimension of about 60–120 nm. Transfection complexes may comprise a mixture of large and small complexes in about equal proportions or they may comprise a preponderance of small or large transfection complexes, e.g., at least about 55%, or at least about 60–80% of the complexes in a given preparation are large or small.

Transfection complexes comprising a lipid optionally include a stabilizing compound(s), e.g., a monosaccharide or a disaccharide such as glucose, trehalose, maltose or sucrose, that is present at the outer surface or at the inner surface or at both surfaces of transfection complexes. Workers have described suitable compounds such as lipids, colipids and stabilizing compounds for making transfection complexes, methods to size the complexes and methods to use the complexes to deliver a polymer or monomer into the cytoplasm of a cell in vitro or in vivo, e.g., U.S. Pat. Nos. 5,635,491, 5,633,156, 5,631,018, 5,629,184, 5,627,159, 5,626,867, 5,620,689, 5,595,756, 5,543,152, 5,478,860, 5,459,127, 5,264,618, 5,223,263, 5,194,654, 4,981,692, 5,077,056, 4,522,803, 4,588,578, 4,885,172, 4,975,282, 5,059,421, 5,000,958, 5,030,453 and 5,047,245, WO 96/01840, WO 96/01841, WO 97/30969, WO 97/30732, Lewis, "Proc Natl Acad Sci" 93:3176–3181, 1996, U.S. patent application Ser. No. 08/672,206.

Invention transfection complexes useful for delivering the invention oligonucleotides into cell cytoplasm also include complexes comprising inorganic compounds, e.g., calcium phosphate.

$R^{21}$

The $R^{21}$ moiety is linked to invention oligonucleotides or monomers useful for oligonucleotide synthesis. $R^{21}$ is usually linked to the 2' or the 3' position of furanose sugars. When $R^{21}$ is a nuclease stability enhancing moiety, a broad range of structures may be used to increase stability of oligodeoxynucleotides or oligoribonucleotides containing phosphodiester linkages. Oligonucleotides having moieties other than hydrogen or hydroxyl at the 2' position usually confer increased nuclease stability or increased binding affinity on the oligonucleotide relative to hydrogen or hydroxyl. Enhanced nuclease stability is conveniently measured using dimers or short oligonucleotides as essentially described, e.g., WO 92/05186. One or two $R^{21}$ moieties at the 3' and 5' terminal monomers in an oligonucleotide will increase stability of the oligonucleotide to 3'- and 5'-exonucleases. One may increase an oligonucleotide's stability to endonucleases by incorporating $R^{21}$ moieties that increase nuclease stability at internal monomer positions.

In addition to increasing nuclease stability, some $R^{21}$ moieties enhance binding affinity of the oligonucleotide to which they are linked. These moieties include fluorine and short unbranched optionally substituted O-alkyl groups containing about 2–8 carbon atoms, where the alkyl group is optionally substituted at the distal carbon atom with, e.g. —F, —OH or —NH$_2$, and optionally substituted with an ether at an internal carbon, e.g., —O—(CH$_2$)$_2$—O—(CH$_2$)$_2$F, —O—(CH$_2$)$_2$OCH$_3$ or —O—(CH$_2$)$_2$—O—(CH$_2$)$_2$CH$_3$.

When $R^{21}$ is a nuclease stability enhancing moiety, it will typically comprise —CH$_3$, =O —NHR$^5$ or a chain having a backbone containing 2, 3, 4, 5, 6, 7, 8, 9, 10, 11 or 12 linked atoms, wherein the chain usually comprises carbon (C) atoms and optionally 1, 2, 3 or 4 atoms independently selected from the group consisting of oxygen (O), nitrogen (N) and sulfur (S) atoms. The chain is usually linked to the sugar carbon atom through —O—, —S—, —S(O)—, S(O)(O)—, —CH$_2$—, =CH— or —NH—. The chain is branched or unbranched, often it is unbranched or has only limited branching, e.g., —CH$_3$, —CH$_2$OH, —C$_2$H$_5$ or —C$_2$H$_4$OH. The $R^{21}$ chain may comprise a C$_{2-12}$ alkyl group or a C$_{2-20}$ substituted alkyl group. If $R^{21}$ is a substituted alkyl group, usually only 1, 2 or 3 carbon atoms are substituted. Suitable substituents include those described above for substituted alkyl groups, e.g., halogen (usually fluorine), —O— or —OR$^5$.

Invention embodiments include oligonucleotides and monomers where one or more monomers comprise 2'-deoxyribose, ribose or arabinose sugars, or their carbocyclic analogs, having one or more 2' $R^{21}$ modification such as, —O— alkyl, —NH—alkyl, —S—alkyl, —OR$^5$, —NHR$^5$, —SR$^5$, -halo (usually —F), —R$^{44}$-alkyl or —R44- substituted alkyl wherein the alkyl or substituted alkyl group usually comprises 1, 2, 3, 4, 5, 6, 7, 8, 9, 10, 11 or 12 carbon atoms, usually about 2–6 carbon atoms, where $R^{44}$ is independently —O—, —S—, —NH— or —CH$_2$—, usually —O—. The oligonucleotide linkages connecting such monomers are 3',5' linkages. The alkyl groups at the 2' position typically have 1, 2, 3, 4, 5, 6, 7, 8, 9, 10, 11 or 12 carbon atoms which are optionally present as methylene groups (—CH$_2$—) and optionally have 1, 2, 3 or 4 ether (—O—) or other substitutions, e.g., O-alkoxyalkyl (C$_2$-C$_{12}$ alkyl), —O—(CH$_2$)$_{2-8}$—CH$_2$CO$_2$H, —O—(CH$_2$)$_{2-8}$—CH$_2$N(R$^5$)$_2$, —(—O—(CH$_2$)$_{2-4}$—O—(CH$_2$)$_{2-4}$—O—(CH$_2$)$_{2-4}$—R$^{65}$), —O(CH$_2$CH$_2$O)$_r$CH$_2$—R$^{65}$, —O—CH$_2$CH$_2$—R$^{65}$, —O(CH$_2$CH$_2$)O(CH$_2$CH$_2$)R$^{65}$, —OCH$_2$CF$_2$CF$_3$, where $R^{65}$ is —H, halo (usually fluorine), —OR$^5$, —OCH$_3$, —NHR$^5$, —SR$^5$, and r is 1, 2, 3 or 4, usually 1 or 2.

The alkyl groups at the 2' position also include substituted alkyl, e.g., —O— alkylamino, —S-alkylamino, —NH-alkylamino, or their protected derivatives, wherein the alkyl group contains 2, 3, 4, 5, 6, 7, 8, 9, 10, 11, or 12 carbon atoms, which are all optionally present as methylene carbons (—CH$_2$—). Usually the alkyl group or substituted alkyl group at $R^{21}$ will contain 1, 2, 3, 4, 5, 6, 7 or 8 carbon atoms. Such groups include —O-methyl, —O-ethyl, —O-n-propyl, —O-allyl, —O—(CH$_2$)$_{2-6}$OH, including —O—(CH$_2$)$_2$OH, —O—(CH$_2$)$_2$F, —O—CH$_2$CHF$_2$, —O—CH$_2$CF$_3$, —O—(CH$_2$)$_{2-6}$OCH$_3$, including —O—(CH$_2$)$_2$OCH$_3$, —O—(CH$_2$)$_2$OCH$_2$CH$_3$, —O—(CH$_2$)$_2$OCH$_2$CH$_2$OH, —O—(CH$_2$)$_2$OCH$_2$CH$_2$F, —O—(CH$_2$)$_2$NHR$^5$, —O—(CH$_2$)$_3$NHR$^5$, —O—(CH$_2$)$_4$NHR$^5$, —O—(CH$_2$)$_2$F, —O—(CH$_2$)$_3$F, —O—(CH$_2$)$_4$F, —O—CH$_2$—CF$_2$CF$_3$, —O—(CH$_2$)$_s$R$^{65}$, —O—(CH$_2$)$_2$—[O—(CH$_2$)$_2$]$_r$R$^{65}$, —NH-methyl, —NH-ethyl, —NH-n-propyl, —NH—(CH$_2$)$_2$OH, —NH—(CH$_2$)$_3$OH, —NH—(CH$_2$)$_2$F, —NH—CH$_2$—CF$_2$CF$_3$, —NH—(CH$_2$)$_s$R$^{65}$, —S-methyl, —S-ethyl, —S-n-propyl, —S-allyl, —S—(CH$_2$)$_s$OH, —S—(CH$_2$)$_3$OH, —S—(CH$_2$)$_2$F and —S—(CH$_2$)$_s$—[O—(CH$_2$)$_2$]$_r$R$^{65}$, where s is 2, 3, 4, 5, 6, 7 or 8. $R^{21}$ moieties do not include unstable species at the 2' position, e.g., —O—O— or —S—O—.

Other suitable $R^{21}$ at the 2' or 3' position of optionally protected invention monomers or optionally protected invention oligonucleotides include —$^2$H, —$^3$H, —NHOR$^{55}$, =NH, —N$_3$, —CN, —CH$_2$CN, —CHCl$_2$, —CFH$_2$, —CF$_2$H, =CH$_2$, =CF$_2$, —CH$_2$CH=CH$_2$, =O, =CHC(O)OR$^{55}$ (including =CHC(O)OCH$_3$ and =CHC(O)OCH$_2$CH$_3$), —OC(S)OC$_6$H$_5$, t-butyldimethylsilyl ether, triisopropylsilyl ether, a 2' amino group protected by an N-phthaloyl protecting group or a fluorescent label, $R^{55}$ is independently $R^5$, alkyl having 1, 2, 3, 4, 5, 6, 7, 8, 9 or 10 carbon atoms or substituted alkyl having 1, 2, 3, 4, 5, 6, 7, 8, 9 or 10 carbon atoms where the carbon atoms in $R^{55}$ are optionally all present as methylene (—CH$_2$—) or substituted methylene (—CH(substitution)-) moieties. Workers have described suitable 2' modified monomers and oligonucleotides, e.g., WO 97/14706, WO 96/05298, WO 93/13121, and WO 91/06556 and U. S. Pat. Nos. 5,631,360, 5,627,053, 5,623,065, 5,576,302 and 5,578,718.

Methods for Synthesis

The compounds of structure (1) where $R^1$ is a linker or H are prepared by methods known in the art per se and as more fully described below. Typically, such compounds are prepared from a 5-bromouracil, 5-bromouridin-1-yl, 5-iodouracil, 5-iodouridin-1-yl substituted derivative as shown in the synthetic schemes below and subsequent reactions close the polycyclic ring. In these embodiments the hydroxyl, amino and any other labile groups of $R^1$ are protected as required. In another approach, $R^1$ of the starting material is H or a protecting group and one adds the linker after the ring closure steps set forth in the schemes, in the same fashion as has heretofore been employed in the alkylation of pyrimidine bases intended for use as antiviral compounds.

In those embodiments in which $R^1$ is a binding partner such as a polymer the compounds of this invention are synthesized by covalently crosslinking the linker modified polycyclic base of this invention to the binding partner, or (where the binding partner is a polymer) by incorporating into the polymer a monomer unit which is substituted by an invention polycyclic base.

In the first embodiment (polymer grafting) a $R^1$-substituted polycyclic substructure is covalently bonded via any conventional cross-linking agent to the polymer. Most conveniently, structure (1) compounds in which $R^1$ is hydroxyl- or amino-substituted alkyl are readily cross-linked to reactive groups present in the molecule to be labeled as noted above. Exemplary cross-linking agents include succinic anhydride, N-hydroxysuccinimide esters (biotin NHS ester), epoxides, isothiocyanates, imidates, DCC (dicclohexylcarbodiimide), EDC (1-ethyl-3-[3-(dimethylamino)propyl] carbodiimide), BOP, and glutaraldehyde, see, e.g., EP 0 063 879, Ruth "J Org Chem" 43:2870, 1978, Bergstrom, JACS 100:8106, 1978, Bigge, JACS 102:2033, 1980. Cyanogen bromide activated carbohydrates also are used. The cross-linking agents are used to bond the $R^1$-substituted polycycle to the polymer in the same fashion as polymers heretofore have been cross-linked to ligands, e.g., to hydroxyl or amino-bearing moieties. An example of a suitable method is described per se in Cook et al., U.S. Pat. No. 5,218,105. This method is readily applied to covalently bond an amino-substituted $R^1$ linker to the 5' terminus of an oligonucleotide.

When $R^1$ or $R^2$ are amino substituted, the following exemplary synthetic approaches are suitable for crosslinking amines with other moieties:

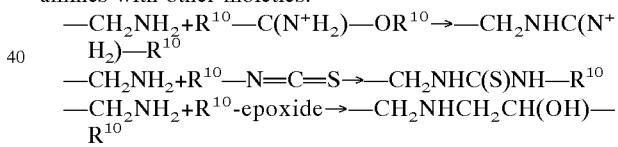

where $R^{10}$ is an organic moiety optionally containing a hapten or other detectable moiety such as biotin or avadin.

In the second embodiment (copolymerization) the $R^1$ linker is capable of functioning as a monomer for copolymerization with other monomer units that may or may not be substituted with the polycyclic substructure of structure (1). In some embodiments, the $R^1$ linker is an alkyl carboxylate, an alkyl amine or an amino acid for incorporation into peptides by in vitro methods. However, in the typical embodiment the $R^1$ polymeric binding partner is an oligonucleotide as depicted in structure (2), and these conveniently are made by copolymerization with a nucleotide analog substituted with the polycyclic substructure. The starting materials for the synthesis of structure (2) generally are compounds of structure (1) in which $R^1$ is ribose or deoxyribose substituted with appropriate protecting and coupling groups further described above. Suitable starting monomers for oligonucleotides having phosphodiester substitute linkages are set forth in Table 1, and they are prepared in the same fashion as other nucleotide analog bases described in the literature. Similarly, conventional phosphodiester or phosphorothioate linkages are prepared from nucleotide analogs containing coupling groups D and $D^1$ described above. The compounds of this invention then are incorporated into the desired oligonucleotide by known methods of in vitro synthesis described in the referenced methods. Alternatively, polycylic substructure-substituted nucleotide triphosphates may be incorporated into oligonucleotides as cytosine analogs by DNA polymerase or reverse transcriptase in vivo or in vitro (see Ward, U.S. Pat. No. 4,711,955). In this case, $R^1$ is ribosyl or deoxribosyl triphosphate, or a triphosphorylated analog thereof recognized by DNA polymerase or reverse transcriptase which is then incorporated into an oligonucleotide by template-directed transcription.

Synthesis of oligonucleotides containing 3 or more nucleotide residues is optionally accomplished using synthons such as dimers (which contain substitute or diester linkages) or trimers, each carrying a terminal coupling group suitable for use with amidite, H-phosphonate or triester chemistries. The synthon is then linked to the oligonucleotide or another synthon via a phosphodiester or phosphorous-containing phosphodiester substitute linkage.

Oligonucleotides containing phosphorothioate, methylphosphonate and phosphodiester linkages are readily prepared by solid-phase oligonucleotide synthesis techniques. A description of modifications useful in the synthesis of phosphorothioate linked oligonucleotides are found, for example, in EP 288,163, wherein the oxidation step in solid phase automated synthesis using amidite chemistry can be independently adjusted at any step to obtain the phosphorothioate. An alternate method for synthesis of oligonucleotides with phosphorothioate linkages, via hydrogen phosphonate chemistry, has also been described (Froehler "NAR" 14:5399, 1986). Sulfurization is accomplished using reagents such as tetraethylthiuram disulfide, dibenzoyl tetrasulfide, thiophosphoric acid disulfide, 3H-1,2-benzodithiol-3-one 1,1-dioxide and the like as described (Vu, "Tet Lett" 26:3005, 1991; Rao, "Tet Lett" 33:4839, 1992; U.S. Pat. No. 5,151,510; Iyer, "JOC" 55:4693, 1990; Dahl, "Sulfur Reports" 11:167, 1991). These sulfurization reagents are used with either phosphoramidite or hydrogen-phosphonate chemistries. Synthesis of phosphorothioate oligonucleotides having controlled stereochemistry is used to generate stereoregular invention oligonucleotides as described (EP 506,242). Thionomethyl phosphonate is prepared with methylphosphonamidite followed by sulfurization as described (Roelen, "Tet Lett" 33:2357, 1992) or with the sulfurization reagents described above.

One prepares various structure (1) compounds as described below and in the examples.

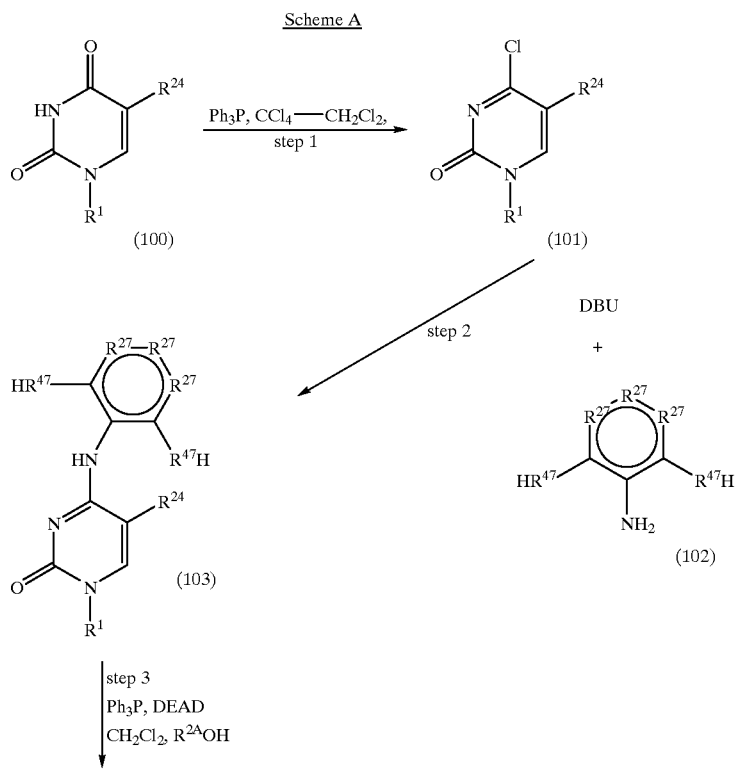

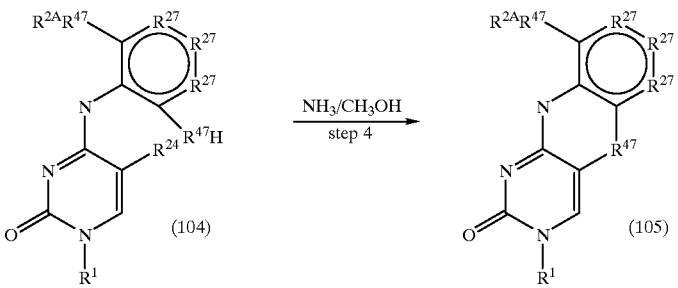

Scheme A depicts preparation of structure (1) compounds where $R^{47}$ is —O— or —S—; and $R^{2A}$—OH is $R^2$ which has a free hydroxyl.

Step one is conducted by heating the reaction mixture containing (100) in an organic solvent to at least about 50° C., generally for about 3–4 hours. Step two is performed by reacting (102) in an organic solvent for about 6–48 hours, generally for about 10–20 hours at about 15° C. to reflux temperature, generally at about 18–25° C. The $R^2$ moiety is linked under Mitsunobu conditions to (103) in step 3 by reacting about 1–1.5 equivalents of the alcohol, i.e., $R^{2A}$—OH, using an activating agent as a leaving group, such as triphenylphosphine ($Ph_3P$) and diethyl diazocarboxylate (DEAD) to obtain (104). In step 4, (105) is prepared by forming the ring containing $R^{47}$ by (1) incubating (104) in a polar organic solvent, typically an alkanol containing 1, 2, 3, 4, 5 or 6 carbon atoms, such as methanol or ethanol, containing a mild base such as $NH_3$, TEA (triethylamine), DBU (1,8-diazabicyclo[5.4.0]undec-7-ene) or (2) refluxing in ethanol in the presence of potassium fluoride. Generally (104) is incubated in saturated $NH_3$ in methanol for about 2–3 days to afford (105).

The use of (102) in which one $R^{47}$ is —O— and the other is —S— will produce a mixture. One optionally isolates each (104) component or one optionally converts the (104) mixture to a (105) mixture. One optionally separates the mixtures at any convenient point by standard methods, e.g., silica gel chromatography, or HPLC.

When one prepares compounds according to scheme A and $R^1$ is a monosaccharide, e.g., 2'-deoxyribose, 2'-deoxy-2'-$R^{21}$-substituted ribose or arabinose, the sugar hydroxyls in (100) are usually protected, generally using base-labile protecting groups, e.g., acetate, proprionate, butyrate, phenoxyacetyl. The step 4 reaction under basic conditions removes the protecting groups, which facilitates the ring formation reaction resulting in (105). When $R^1$ is not a monosaccharide, it is generally a protecting group or an optionally protected linker, e.g., —$(R^{48})_X$—$R^{49}$, where $R^{48}$ is independently —$CH_2$—, —O—, —S—, —NH— or —C(O)—, X is 1, 2, 3, 4, 5, 6, 7, 8, 9 or 10 and $R^{49}$ usually is a functional group suitable for linking to a solid support, monomer or polymer, including —$OR^5$, —$SR^5$, —$N(R^5)_2$, —$C(O)N(R^5)_2$, —$NR^5C(O)H$, —C(O)H and —$C(O)OR^5$, $R^5$ is independently —H, a protecting group, or both $R^5$ together are a protecting group. Generally the $R^{48}$ group that is adjacent to $R^{49}$ is ethylene (—$CH_2$—$CH_2$—) and generally only 0, 1 or 2 $R^{48}$ are moieties other than —$CH_2$—, e.g., one $R^{48}$ is —O— or —C(O)— and the remaining $R^{47}$ are all —$CH_2$—. Exemplary compounds where $R^1$ is a monosaccharide have the structures (130)–(134), which correspond to compounds (100)–(101) and (103)–(105) respectively. For compounds (130)–(132), $R^5$ at sugar hydroxyls is typically a base labile protecting group such as acetyl and $R^{37}$ is typically —O—. During conversion of (133) to (134), the $R^5$ protecting group is removed from the sugar under ring closure reaction conditions, which facilitates ring closure.

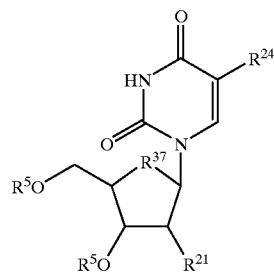

(130)

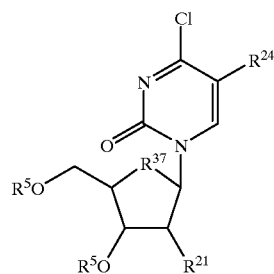

(131)

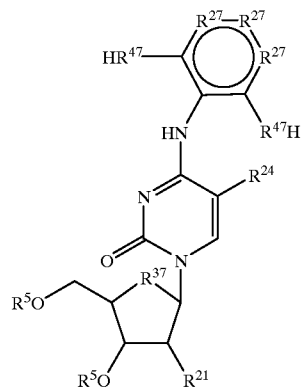

(132)

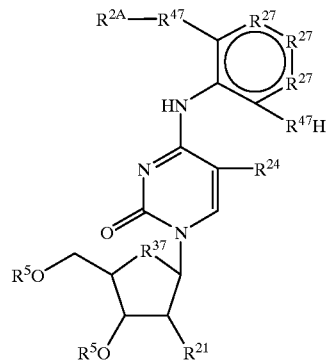

(133)

-continued

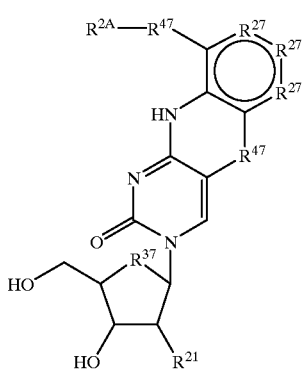

(134)

Structure (134) compounds may be converted to monomers suitable for oligonucleotide synthesis. Such monomers typically have a coupling group at the 3' position, e.g., H-phosphonate, or a phosphoramidite such as a β-cyanoethylphosphoramidite, N,N-diisopropylamino-β-cyanoethoxyphosphine or N,N-diisopropylaminomethoxyphosphine. The 5' position will contain a DMT-O— or other protecting group suitable for oligonucleotide synthesis. The monomers may alternatively have a coupling group at the 5' position and a protecting group at the 3' position. The protecting and coupling groups are added sequentially. Scheme B shows synthesis of structure (1) compounds where $R^6$ in $R^2$ is —CH$_2$—. In scheme B, Y is 1, 2, 3 or 4; $R^{50}$ is independently —CH$_2$—, —C(O)—, —(CH$_2$)$_2$—O—(CH$_2$)$_2$—, —(CH$_2$)$_2$—NR$^5$—(CH$_2$)$_2$—, —(CH$_2$)$_2$—S—(CH$_2$)$_2$—, —CH(N(R$^5$)$_2$)—, —CH(COOR$^5$)— or —C(CH$_3$)—, —C(C$_2$H$_5$)— but adjacent moieties are not C(O), usually $R^{50}$ is —CH$_2$—; TFA is trifluoroacetate; and CBZ is carboxybenzoyl; and (96) is HC≡C(R$^{50}$)$_y$—NH-TFA. Protecting groups present in $R^{50}$ are stable to the reaction conditions shown.

Scheme B

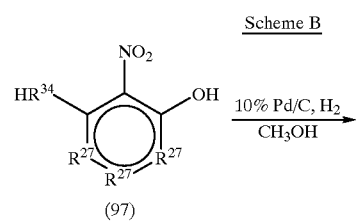

(97)

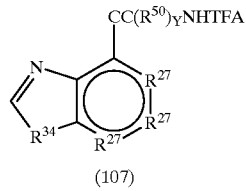

(107)

(107) 1. H$_2$, 10% Pd/C
2. NH$_4$OH (conc.)
dioxane (1:1) → (108)

pyridine
C$_6$H$_5$CH$_2$OC(O)Cl

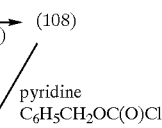

(109)

HCl/
EtOH (1:1)

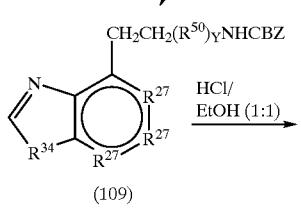

(110)

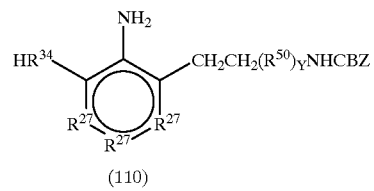

(111)

DBU, CH$_2$Cl$_2$
(110)

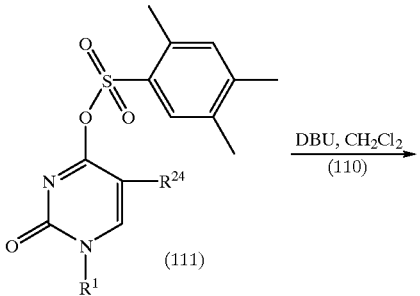

(112)

(112) NH$_3$/CH$_3$OH

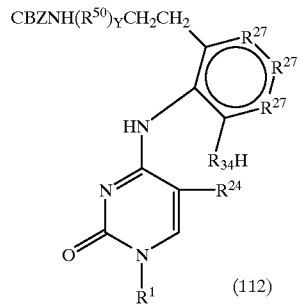

(99) Tf$_2$NPh, K$_2$CO$_3$
CH$_2$Cl$_2$/DMF
→
(106)

(96)
Pd(PPh$_3$)$_4$,
TEA

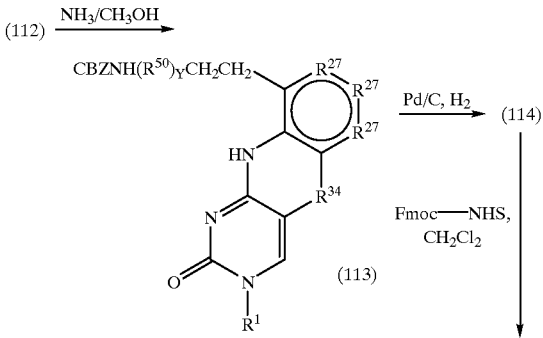

(113)

Pd/C, H$_2$ → (114)

Fmoc—NHS,
CH$_2$Cl$_2$

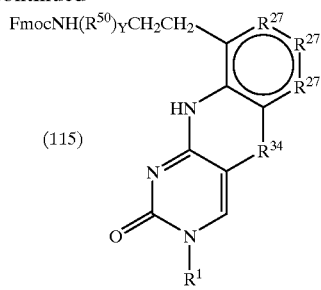

(115)

Compound (97) is converted to (98) by hydrogenation reaction in alcohol, usually methanol or ethanol, at about 15–25° C. for about 10–24 hours, usually about 12–18 hours. The catalyst is removed and the filtrate is concentrated.

Compound (98) in trimethyl orthoformate is converted to (99) in the presence of acid, e.g., methanesulfonic acid at about 15–25° C., usually about 18–22° C. for about 20–120 minutes. The reaction is cooled and quenched with a base, e.g., an organic base such as TEA. The reaction mixture is concentrated and purified, e.g., by flash column chromatography on silica gel.

Compound (106) is prepared by reacting (99) in organic solution such as DMF, $CH_2Cl_2$ or $CH_2Cl_2$/DMF (about 2:1 v/v) with $K_2CO_3$ at about 15–25° C. for about 30 minutes, followed by adding phenyltrifluoromethanesulfonimide and stirring the mixture for about 10–24 hours, usually about 12–16 hours. The reaction mixture is then diluted with $CH_2Cl_2$, washed with water once or twice and concentrated and purified.

Compound (96) is prepared by reacting $HC\equiv-C(R^{50})_YNH_2$ with ethyl trifluoroacetate at about 15–25° C. for about 10–24 hours, washing with saturated aqueous $NaHCO_3$ and concentrated. Compound (96) is purified by distillation.

Compound (107) is prepared by stirring an organic solvent such as DMF containing about 2 equivalents of (96), about 2 equivalents of an organic base such as TEA, and $Pd((PPh)_3)_4$, CuI and about 1 equivalent of (106) at about 15–25° C. for about 18–36 hours. The organic phase is washed with water, dried and purified by silica gel chromatography, to obtain (107).

Compound (107) is hydrogenated in ethanol in the presence of 10% Pd/C at room temperature. The catalyst is filtered off, the filtrate is concentrated and then treated with conc. $NH_4OH$:dioxane (1:1) to afford (108). The amino group in (108) was protected with CBZ to afford (109).

Compound (110) is prepared by treating (109) in ethanol with aqueous HCl (about 3 N) at about 15–45° C., usually about 40° C., for about 30–120 minutes, usually about 60 minutes. The product is dried and optionally azeotroped using e.g., $CH_3CN$, several times.

Compound (111) is prepared by reaction of (100) with mesitylenesulfonyl chloride in the presence of a tertiary amine such as TEA.

Compound (112) is prepared by stirring a mixture of (110) and (111) in organic solution containing about 2 equivalents of an organic base such as DBU or TEA at about 15–25° C. for about 10–24 hours. The reaction mixture is washed with an aqueous 10% citric acid solution, dried and purified by silica gel chromatography.

Compound (113) is prepared by treating (112) with saturated $NH_3$ in methanol at about 15–25° C. for about 3–4 days. The reaction mixture is dried, concentrated and purified by silica gel chromatography.

Compound (114) is prepared by hydrogenation of (113) in the presence of 10% Pd/C at about 15–25° C. for about 3–6 hours. Catalyst is removed, washed, and the filtrate is concentrated to dryness. The amino group in (114) is protected with FMOC to afford (115).

Where $R^1$ in scheme B is an optionally protected monosaccharide such as 2'-deoxyribose, 2'-deoxy-2'-$R^{21}$-substituted ribose, 2'-deoxy-2'-$R^{21}$-substituted arabinose, ribose or arabinose, the sugar's hydroxyl groups in compounds (111) and (112) are usually protected with a base-labile protecting group such as acetyl, propionyl and phenoxyacetyl. These protecting groups are removed by treatment with base during synthesis of (113).

Exemplary compounds where $R^1$ is a monosaccharide have the structures (135)–(139), which correspond to compounds (111)–(115) respectively. For compounds (135)–(136), $R^5$ at sugar hydroxyls is typically a base labile protecting group such as acetyl. $R^{37}$ is typically —O—. During conversion of (136) to (137), the $R^5$ protecting group is removed from the sugar under ring closure reaction conditions, which facilitates ring closure.

Structure (139) compounds may be converted to monomers suitable for oligonucleotide synthesis. Such monomers typically have a coupling group at the 3' position, e.g., H-phosphonate, or a phosphoramidite such as a β-cyanoethylphosphoramidite, N,N-diisopropyl-amino-β-cyanoethoxyphosphine or N,N-diisopropylaminomethoxyphosphine. The 5' position will contain a DMT-O- or other protecting group suitable for oligonucleotide synthesis. The monomers may alternatively have a coupling group at the 5' position and a protecting group at the 3' position. The protecting and coupling groups are added sequentially.

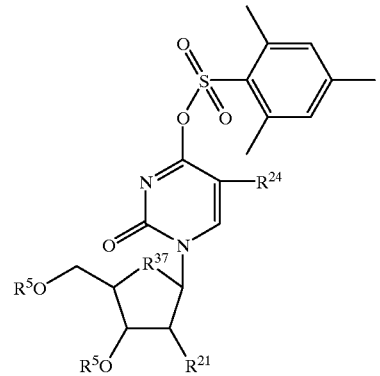

(135)

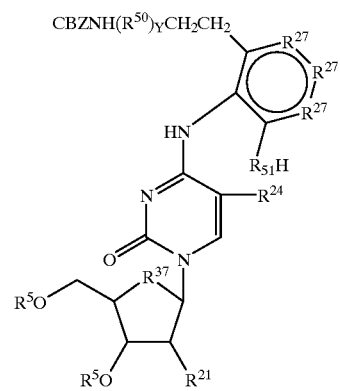

(136)

-continued

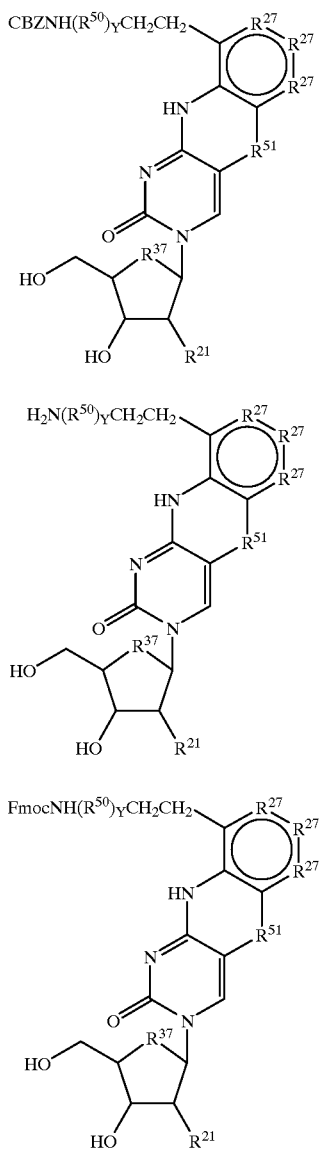

Scheme C shows synthesis of structure (1) compounds where $R^6$ in $R^2$ is —NH—.

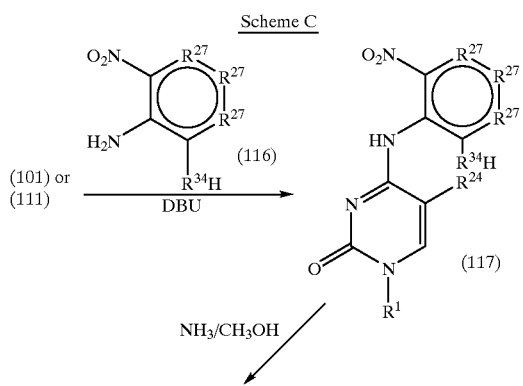

-continued

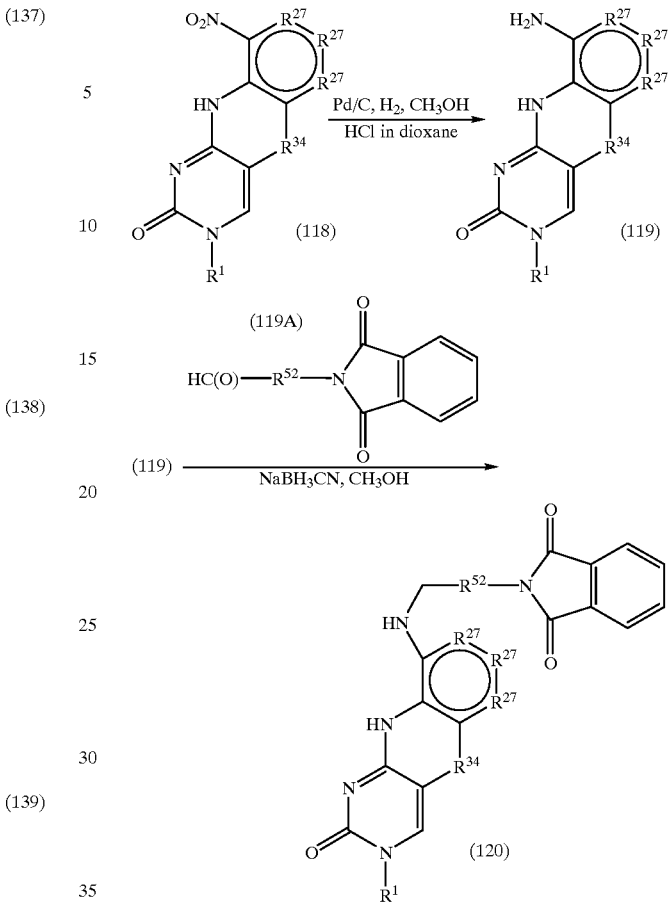

In scheme C, $R^{52}$ is —(CHR$^{52A}$)—(R$^{52B}$)—CHR$^{52A}$—, where $R^{52A}$ is —H or $C_1$-$C_6$ alkyl (typically $C_1$-$C_3$), usually —H, and $R^{52B}$ is a bond, —CHR$^{52A}$—O—CHR$^{52A}$—, —CHR$^{52A}$—S—CHR$^{52A}$—, —CHR$^{52A}$—NR$^5$—CHR$^{52A}$—, $C_1$-$C_{10}$ alkylene (typically $C_3$-$C_6$) optionally substituted with 1 or 2 moieties selected from the group consisting of $C_1$-$C_6$ alkyl (typically $C_1$-$C_3$ alkyl), —OR$^5$, =O, —NO$_2$, —N$_3$, —CN, —COOR$^5$, or —N(R$^5$)$_2$. In R$^{52}$, any heteroatom in the spacer chain will be separated from the nitrogen atoms that $R^{52}$ is linked to by one methylene and one or more —CHR$^{52A}$— moieties. Typically, adjacent carbon atoms in $R^{52B}$ are not substituted with —OR$^5$, =O, —NO$_2$, —N$_3$, —CN, —COOR$^5$, or —N(R$^5$)$_2$. Protecting groups present on (119A) are usually stable to oxidizing conditions and labile to basic conditions. The protected intermediate (119A) is prepared by reacting phthalic anhydride with the appropriate HOCH—R$^{52}$—NH$_2$ moiety to yield a phthalimide compound or by reacting a phthalimide compound with HOCH—R$^{52}$—Br.

Compound (117) is prepared by reacting (101) or (111) with about 1.0–1.5 equivalents, usually about 1.1 equivalents of (116) and about 1–2 equivalents, usually about 2 equivalents of organic base such as DBU or TEA in an organic solvent such as CH$_2$Cl$_2$/CCl$_4$ (about 1:1) or CH$_2$Cl$_2$ by reaction at about 10–30° C., usually at about 18–25° C. for about 16–48 hours, usually about 20–28 hours.

Where $R^1$ in scheme C is an optionally protected monosaccharide such as 2'-deoxyribose, 2'-deoxy-2'-R$^{21}$-substituted ribose, 2'-deoxy-2'-R$^{21}$-substituted arabinose, ribose or arabinose, the sugar's hydroxyl groups in compounds (101), (111) and (117) are usually protected with a base-labile protecting group such as acetyl, propionyl and phenoxyacetyl. These protecting groups are removed by treatment with base during synthesis of (118). Compound (118) was hydrogenated in ethanol and acid to obtain (119). Compound (120) was obtained by reductive alkylation of (119) with aldehydes.

Compound (120) is optionally converted, without removing the nitrogen protecting group linked to the exocyclic amine, to a monomer suitable for use in oligonucleotide synthesis, e.g., (121) (not shown), by protecting the 5' hydroxyl group by reaction with a protecting group reagent such as DMT-Cl (4,4'-dimethoxytrityl chloride) to obtain the 5'-protected derivative (not shown). Compound (121) is then converted to a derivative (121A) (not shown) suitable for coupling the 3' hydroxyl group with another 5' hydroxyl group, i.e., a coupling group such as H-phosphonate or a phosphoramidite, e.g., N,N-diisopropylamino-β-cyanoethoxyphosphine or N,N-diisopropylaminomethoxyphosphine, is linked to the 3' position. Exemplary compounds where $R^1$ is a monosaccharide have the structures (140)–(143), which correspond to compounds (117)–(120) respectively. For compounds (140)–(141), $R^5$ at sugar hydroxyls is typically a base labile protecting group such as acetyl and $R^{37}$ is typically —O—. In structure (143) compounds, the 5' or 3' oxygen, usually the 3' oxygen, is linked to —H or a coupling group such as H-phosphonate, or a phosphoramidite such as β-cyanoethylphosphoramidite, N,N-diisopropylamino-β-cyanoethoxyphosphine or N,N-diisopropylaminomethoxyphosphine. During conversion of compound (140) to (141), the $R^5$ protecting group is removed from the sugar under ring closure reaction conditions, which facilitates ring closure.

(140)

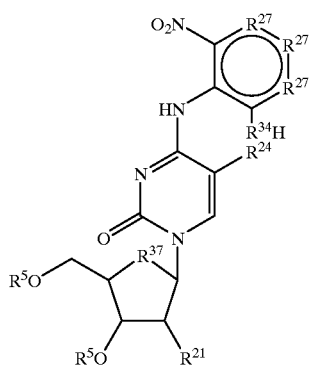

(141)

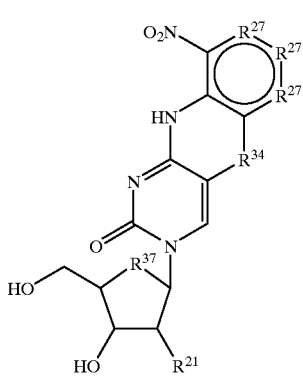

(142)

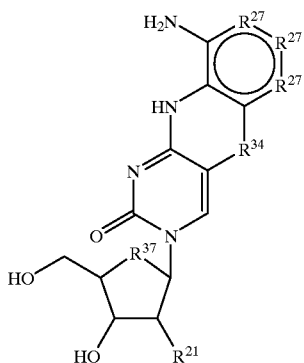

(143)

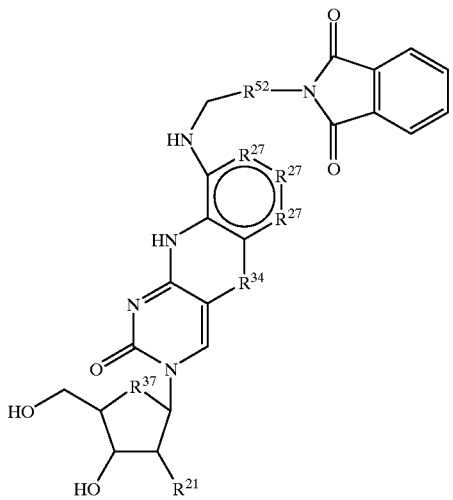

Structure (143) compounds may be converted to monomers suitable for oligonucleotide synthesis. Such monomers typically have a coupling group at the 3' position, e.g., H-phosphonate, or a phosphoramidite such as a β-cyanoethylphosphoramidite, N,N-diisopropylamino-β-cyanoethoxyphosphine or N,N-diisopropylaminomethoxyphosphine. The 5' position will contain a DMT, MMT or other protecting group suitable for oligonucleotide synthesis. The monomers may alternatively have a coupling group at the 5' position and a protecting group at the 3' position. The protecting and coupling groups are added sequentially. During oligonucleotide synthesis, (143) is incorporated into an oligonucleotide such, as one of structure (2), by standard methods and the phthalamide protecting group, along with other base labile protecting groups at $R^{52}$ are removed using basic conditions, e.g., $NH_4OH$ or $NH_2CH_3$, to yield deprotected or partially deprotected —NH—$R^{52}$—$NH_2$ as $R^2$.

Straightforward variations of schemes A–C can be used to prepare other structure (1) compounds. For example, scheme D depicts a method to prepare structure (1) compounds where $R^2$ comprises a cytosine derivative. In scheme D, iPr is isopropyl; $R^{59}$ is a portion of an $R^2$ moiety having the structure —$R^6$—$R^{60}$—, where $R^6$ is usually —O—, —S—, —NH— or —$CH_2$—; $R^{60}$ is —$(CH_2)_{Z3}$—$(R^{61})_{Z1}$—$(CH_2)_{Z2}$—; $R^{61}$ is —O—, —S—, —$NR^5$—, —C(O)—, —$CH_2$—O—$CH_2$—, —$CH_2$—$NR^5$—$CH_2$— or —$CH_2$—S—$CH_2$—; Z3 is 1, 2 or 3, usually 1; Z1 is 0 or 1, usually 0; and Z2 is 1, 2 or 3, usually 1; any functional groups, e.g., —OH, —$NH_2$, —COOH, —SH, that are optionally present at $R^{21}$ are protected. Compound (124) is 3',5'-diacetyl-$O^4$-sulfonyl-2'-deoxyuridine, the synthesis of which is described in the examples.

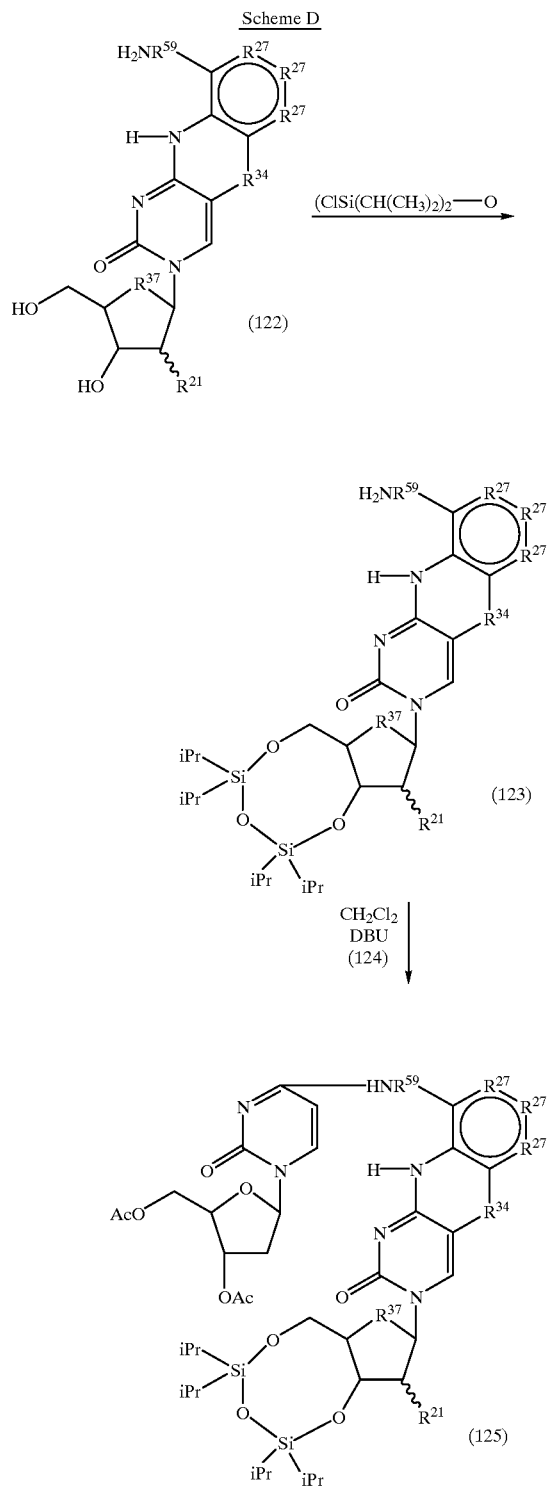

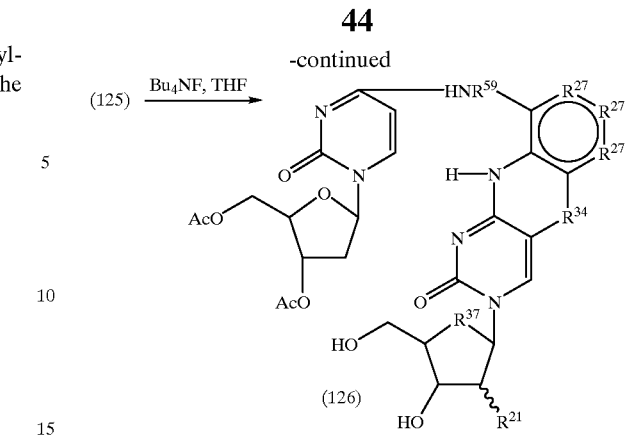

Compound (126) of scheme D is converted to a monomer suitable for oligonucleotide synthesis using standard methods, e.g., treatment of (126) with a protecting group such as DMT-Cl protects the 5' oxygen atom and yields compound (127) (not shown). One then links a coupling group such as H-phosphonate or a phosphoramidite group such as N,N-diisopropylamino-β-cyanoethoxyphosphine or N,N-diisopropylaminomethoxyphosphine to the 3' hydroxyl group, of (127) to obtain (128) (not shown), which is suitable for oligonucleotide synthesis. Variation of the synthesis shown in scheme D is used to prepare compounds of structure (129) or (129A).

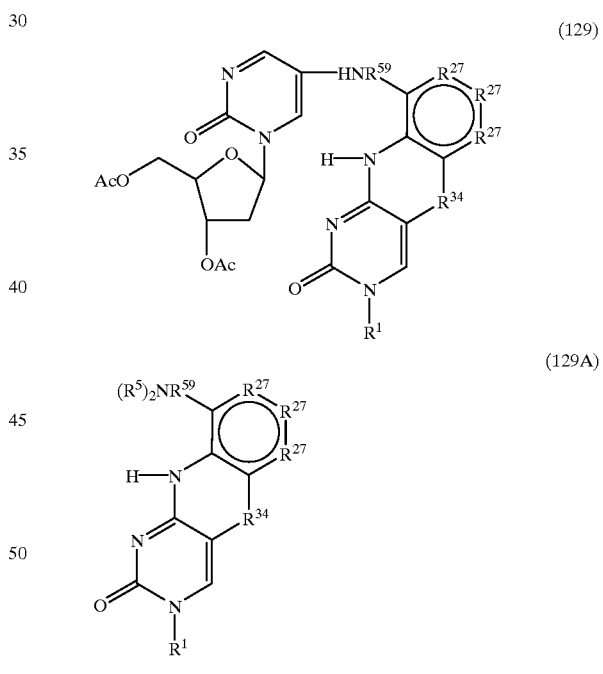

Similarly, structure (1) compounds where $R^2$ is

-continued

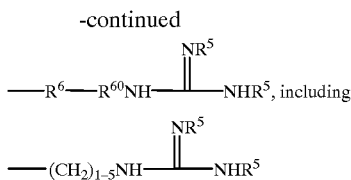

are synthesized using variations of scheme D and the corresponding intermediates, e.g., reaction of (123) with 2-halopyridine (Bernatowicz "JOC" 57:2497 1992).

Compounds of structure (1) where $R^2$ is

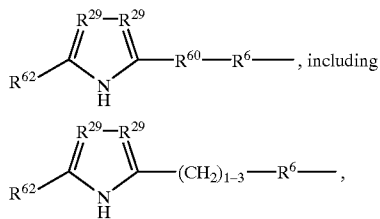

where $R^{29}$ is —N—, —CH— or —C(CH$_3$)—, $R^{62}$ is —H, —NH$_2$ or —NH(CH$_3$) and $R^6$ is —O— or —S— are synthesized using scheme A, while scheme B is used when $R^6$ is —CH$_2$— and scheme C is used when $R^6$ is —NH—.

Compounds of structure (1) where $R^2$ is

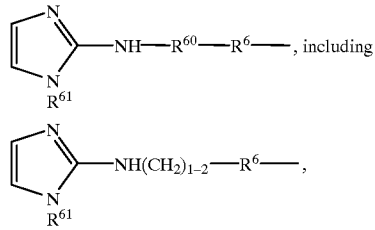

where $R^{61}$ is —H, alkyl having 1, 2, 3 or 4 carbon atoms or optionally protected substituted alkyl having 1, 2, 3, 4, 5 or 6 carbon atoms including —CH$_3$ and —CH$_2$CH$_3$, and $R^6$ is —O— or —S— are synthesized using scheme A, while scheme B is used when $R^6$ is —CH$_2$— and scheme C is used when $R^6$ is —NH—.

Compounds of structure (1) where $R^2$ is —$R^6$—$R^{60}$—N(R$_3$)$_2$, including —$R^6$—(CH$_2$)$_t$—N(R$_3$)$_2$, and $R^6$ is —O— or —S— are synthesized using scheme A, while scheme B is used when $R^6$ is —CH$_2$— and scheme C is used when $R^6$ is —NH—.

Compounds of structure (1) where $R^2$ is

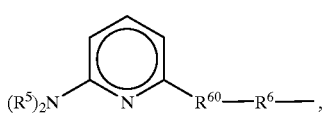

including

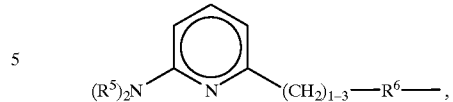

and $R^6$ is —O— or —S— are synthesized using scheme A, while scheme B is used when $R^6$ is —CH$_2$— and scheme C is used when $R^6$ is —NH—. Compounds containing these structures where $R^6$ is —S— or —O—, in general are synthesized using Scheme A and compound (103), e.g., using #1154-093 described in the examples below, and the corresponding protected alcohols. Compounds where $R^6$ is —CH$_2$— are obtained by following Scheme B. Compounds where $R^6$ is —NH— can be obtained using compound (119), e.g., using #1090-68 and protected aldehydes described in the examples below, by following Scheme C.

Schemes E and F illustrate the synthesis of alcohols containing an imidazole moiety (see, e.g., Munk "J. Med. Chem." 40:18 1997). In scheme E, $R^{62}$ is $R^5$ or alkyl having 1, 2, 3, or 4 carbon atoms and $R^{63}$ is —OR$^5$, —(CH$_2$)$_{Z3}$OR$^5$ or —(CH$_2$)$_{1-2}$—R$^{47}$—(CH$_2$)$_{1-2}$—OR$^5$ and Z4 is 0, 1, 2, 3, 4 or 5. In scheme F, Z5 is 1, 2, 3, 4 or 5.

Scheme E

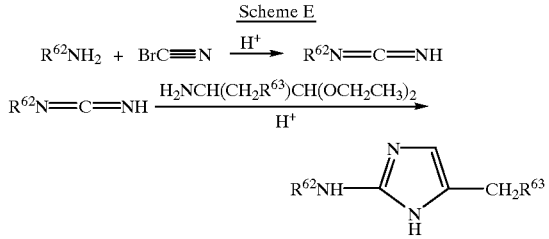

Scheme F

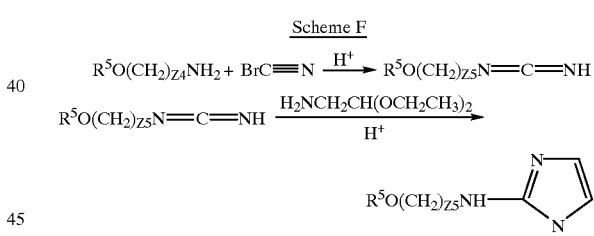

Scheme D is also used to obtain compounds of structure (1) where $R^2$ comprises, for example, a moiety such as —(CH$_2$)$_{2-4}$—NH((CH$_2$)$_{2-4}$NH)$_{0-4}$—(CH$_2$)$_{2-4}$NH$_2$, —(CH$_2$)$_{2-4}$NH(CH$_2$)$_{2-4}$N((CH$_2$)$_{0-4}$—NH$_2$)$_2$, or when $R^2$ is —R$^6$(CH$_2$)$_t$N(R$^3$)$_2$ and one $R^3$ is H, CH$_3$, CH$_2$CH$_3$, a protecting group or —(CH$_2$)$_v$—N(R$^{33}$)$_2$ and the other $R^3$ is —(CH$_2$)$_v$—N(R$^{33}$)$_2$, —CH(N[R$^{33}$]$_2$)—N(R$^{33}$)$_2$, (48), (49) or (50).

Converting a compound of structure (4) to a compound of structure (1) is accomplished by a method comprising displacing $R^{24}$. In this method, $R^{24}$ usually is —Br and $R^{27}$ is usually —CH—.

$R^2$ groups containing a diol, e.g. (CH$_2$OH)$_2$—CH—(CH$_2$)$_n$—O— where n is 1–8, are converted by cleavage to the aldehyde CHO—CH$_2$—(CH$_2$)$_n$—O— using sodium periodate. Reductive alkylation of the aldehyde to a primary or secondary amine is accomplished using N(R$^{34}$)$_2$ where R$^{34}$ independently is —H, C$_{1-6}$ alkyl, including —CH$_3$, —CH$_2$CH$_3$ or a protecting group, usually —H or —CH$_3$.

To the extent that a compound within the claims' scope can not be directly synthesized using the schemes above or the examples below, the artisan will employ straightforward methods known for preparing such compounds, see e.g., B. M. Trost & I. Fleming, eds. "Comprehensive Organic Synthesis", volumes 1–8, Pergamon Press; M. Fieser, ed. "Fieser and Fieser's Reagents for Organic Synthesis", volumes 1–17, John Wiley & Sons; and A. F. Finch Ed. "Theilheimer's Synthetic Methods of Organic Chemistry", volumes 1–49, latest editions, S. Karger AG.

Uses for the Compounds of this Invention

The compounds of this invention find uses in the diagnostic, analytic and therapeutic fields, or as intermediates in the preparation of compounds useful in such fields.

The $R^2$-substituted compounds of structure (1) are useful as intermediates in the preparation of the labeled biopolymers of structure (1), wherein a biopolymer is rendered fluorescent or otherwise detectably labeled by linkage to the polycyclic substructure. It is most convenient, however, to use the appropriate structure (1) compounds as monomers in the preparation of nucleic acids or oligonucleotides. The labeled biopolymers are employed in diagnostic assays or preparative procedures in the same fashion as other fluorophor-labeled biopolymers, e.g. in fluorescence polarization methods, fluorescence activated cell sorting, competitive-type EMIT immunoassays and the like.

The linker- and hydrogen-substituted compounds of structure (1) are useful as intermediates to prepare materials suitable for use in affinity purification of guanine or guanine-containing compounds, e.g., nucleosides. The structure (1) compounds form hydrogen bonds with guanine and one can thus link the structure (1) base structure to an appropriate support material or polymer to prepare an affinity resin suitable for binding to guanine-containing compounds, e.g., nucleosides, nucleotides and oligonucleotides or similar compounds containing guanine analogs, e.g., 7-deazaguanine. Typical linker-derivatized structure (1) compounds optionally contain a linker of structure —$(R^{48})_X$—$R^{49}$, defined above in the discussion under Scheme A.

The monomers are of particular use in preparing oligonucleotides for diagnostic or therapeutic use. Since oligonucleotides having 2 or more nucleotides or nucleotide analogs bearing the polycyclic substructure will usually exhibit greatly increased Tm, such oligonucleotides are particularly useful in therapeutic or diagnostic utilities where highly stable duplex hybridization structures are desired. Since these oligonucleotides frequently are fluorescent, changes in the oligonucleotide fluorescence can be followed as the oligonucleotide binds to complementary nucleic acid or oligonucleotide sequences. These changes are detectable as modifications in energy transfer, e.g., fluorescence quenching or shifts in activation or emission wavelength(s).

The polycyclic substructure labeled oligonucleotides are employed in diagnostic or analytic methods in the same fashion as other labeled oligonucleotides. For example, the oligonucleotides are used in hybridization methods in which an antibody capable of binding base-paired structure (1) is used to detect binding of the oligonucleotide to a target nucleic acid sequence. In addition, changes in fluorescent character can be assayed as described above. Typically, 2, 3 or more polycyclic substructure labeled oligonucleotides are used in a hybridization assay. One oligonucleotide is labeled at its 3' end with a polycyclic substructure containing nucleotide while the other nucleotide is labeled at its 5' end with the same or another polycyclic substructure or with a different fluorophor such as fluorescein or rhodamine capable of energy transfer. The two oligonucleotides recognize a complementary sequence in which the 3' end of the target sequence binds the oligonucleotide bearing the 3'-terminal fluorophor and the adjacent 5' sequence of the target binds to the oligonucleotide bearing the 5' terminal fluorophor. Binding is assayed by measuring a change in fluorescence of either or both of the oligonucleotides when they bind in tandem according to the illustrated model. In other embodiments only a single labeled oligonucleotide is employed in the hybridization method. The oligonucleotides of this invention thus are useful in solution phase hybridization diagnostics, i.e., it is not necessary to perform a phase separation in order to detect labeled oligonucleotide binding.

Detecting a target base sequence in a nucleic acid or an oligonucleotide using an invention oligonucleotide is accomplished by a method comprising (i) mixing or contacting a sample suspected of containing a nucleic acid with an optionally labeled invention oligonucleotide comprising at least about 7 bases, usually about 12–30 bases, where the protecting groups have been removed, (ii) allowing time sufficient for the invention oligonucleotide to bind to the target base sequence, (iii) separating unbound invention oligonucleotides from bound invention oligonucleotides and (iii) detecting the presence, absence or amount of bound invention oligonucleotide. Aspects of the invention include conducting any one of these steps individually, which are each part of the complete method. The use of known hybridization methods and conditions are applied to accomplish the method.

In this method to detect target base sequences, one may optionally use invention oligonucleotide and target base sequences that are substantially complementary to each other, i.e., sequences having 1 or no mismatches per about every 15–30 bases. The target base sequences to be detected are generally present in a cell, in a cell or tissue extract or, usually, in a purified nucleic acid or oligonucleotide preparation, e.g., a sequence encoding a portion of a cytokine, cell surface molecule, an enzyme such as farnesyl protein transferase or an oncogene such as neu, myc, raf, ras or c-ras. The target base sequences to be detected are generally present in RNA or single stranded DNA, although the invention oligonucleotides are also useful to detect base sequences in duplex nucleic acids.

Another invention embodiment is a method comprising incubating a cell with a deprotected invention oligonucleotide containing at least about 7 bases, usually about 12–30 bases, wherein the invention oligonucleotide is optionally present in a transfection complex comprising the invention oligonucleotide and a permeation enhancing agent. This method is used to introduce optionally labeled invention oligonucleotides into cell cytoplasm or vacuoles.

One optionally conducts this method using invention oligonucleotides having a octanol:water partition coefficient of about –0.5 to about 2.5, typically about 0.0 to about 2.0, usually about 0.5–1.5, and a solubility in water of at least 0.001 µg/mL. However, in these embodiments, no permeation enhancing agent is usually needed to introduce the compound into the cells.

One can use oligonucleotides containing 1, 2, 3 or more invention base(s) to detect a base pair mismatch in a nucleic acid sample using ribonuclease protection assay methods described in U.S. Pat. No. 5,589,329. Thus, one can use the invention compounds as described in step (a) or step (b) or step (c) (or, in sequence, steps a, b, or steps b, c or steps a, b, c) of claim 1 of U.S. Pat. No. 5,589,329 to practice that claimed method (or to practice necessary steps in the claim 1 method, e.g., contacting an RNA probe containing an invention base with a single stranded nucleic acid to form a duplex). One can similarly use oligonucleotides containing an invention base(s) to screen mammalian genomic DNA samples for insertions, deletions or substitutions using screening assay methods described in U.S. Pat. No. 5,589, 330. Thus, one can use the invention compounds as described in step (ii) or step (iii) or step (iv) or step (v) (or, in sequence, steps i, ii, or steps i, ii, iii or steps iii, iv, or steps i, ii, iii, iv, etc.) of claim 1 of 5,589,330 to practice that claimed method (or to practice necessary steps in the claim 1 method, e.g., contacting an oligonucleotide containing an invention base with an immobilized genomic DNA sample to form a triplex or duplex). One can similarly use oligonucleotides containing an invention base(s) to design a synthesis method for an array of materials to be synthesized on a substrate using methods described in U.S. Pat. No. 5,593,839. Thus, one can use the invention compounds as described in the first part of the second step or the second part of the second step or the third part of the second step or the fourth part of the second step or (or, in sequence, in the first step and in the first part of the second step, etc.) of claim 1 of 5,593,839 to practice that claimed method (or to practice necessary steps in the claim 1 method).

One can also use the invention monomer compositions containing a 5'a-$^{35}$S-thiotriphosphate group or a 5' triphosphate group linked to 2',3'-dideoxyribose to perform dideoxy DNA sequencing methods. One may use invention monomers in kits that optionally contain buffers or enzymes suitable for DNA sequencing. The invention monomers may be advantageously used in enzymatic DNA sequencing protocols because the invention monomers, which act as cytosine surrogates, have a high affinity for guanosine and may perform better than cytidine 5' triphosphate in sequencing reactions, particularly where the DNA to be sequenced contains a high proportion of guanosine residues, which can cause sequencing problems.

Oligonucleotide analogs containing 1, 2, 3 or more invention bases are also suitable for binding to open complexes in cells or cell lysates of eukaryotic or prokaryotic cells. Open complexes may also arise in systems comprising at least partially purified cell components, e.g., RNA polymerase, nucleotide triphosphates, suitable transcription cofactors, DNA binding proteins and duplex DNA capable of transcription. Open complexes are regions of single stranded DNA or RNA that occur at least transiently during duplex nucleic acid metabolism, e.g., during DNA replication or RNA transcription in the nucleus, cytoplasm, plastids or mitochondria. Such DNA replication or RNA transcription may involve metabolism of cellular, viral or other nucleic acids. One can use binding of invention oligonucleotides to single stranded open complex sequences to affect nucleic acid metabolism, e.g., one may inhibit RNA transcription or one may use the oligonucleotides, which are optionally labeled, to detect the presence of open complexes. Such oligonucleotides will typically comprise about 8 to 30 monomers, usually about 12–21 monomers, having a sequence complementary to a single stranded open complex region(s) involved in the initiation of a nucleic acid metabolic event, e.g., initiation of RNA transcription in a promoter or transcription initiation region. Workers have described open complexes and their formation in vitro and in cells, e.g., Burns, "Biochem. J." 317:305–11 1996, Smith, "Proc. Natl. Acad. Sci. USA" 93:8868–72 1996, Jiang, "J Biol Chem" 268:6535–40 1993.

Workers have described other applications that one can practice in a similar straightforward manner using optionally labeled oligonucleotides containing 1, 2, 3 or more invention bases, see e.g., U.S. Pat. Nos. 4,910,300, 5,093,232, 5,124, 246, 5,202,231, 5,258,506, 5,202,231, 5,525,464, 5,578,717, 5,578,715, 5,578,467, 5,591,584, 5,599,932, 5,599,668, 5,593,841, 5,578,458, 5,589,332, 5,589,333, 5,589,339, 5,589,342, 5,593,830, 5,593,831, 5,593,832, 5,593,836, 5,593,840, 5,593,841, 5,593,863, 5,604,097, 5,604,099, 5,605,793, 5,605,794, 5,605,796, 5,605,798, 5,605,824, 5,606,047, 5,608,063, 5,614,617, 5,594,117, 5,633,364, 5,639,612, 5,639,611, 5,639,608, 5,639,647, 5,639,736, 5,639,626, 5,641,631, International Publication Nos. WO 97/07246, WO 97/06252, WO 97/06183, WO 97/04787, WO 97/05280, WO 96/41017, WO 96/41012, WO 96/40994, WO 96/40996, WO 96/40991, WO 96/40992, WO 96/41016, WO 97/04126, WO 97/04129, WO 96/06950 and European Publication No. 761 822. For each of these applications, one would use an invention oligonucleotide in place of one or more of the described oligonucleotides. To practice these and other typical applications, one will typically use an invention oligonucleotide in one or more of the steps needed to practice the methods described in these publications. In many of these applications, one will use an invention oligonucleotide containing (i) about 7–50, usually about 8–30 linked monomers, usually where the oligonucleotide has a uniform polarity, (ii) 1, 2 or 3 invention bases, (iii) purine and pyrimidine bases having a base sequence complementary or substantially complementary to a target sequence, i.e., a defined base sequence having no more than about 1, 2, 3 or, for relatively long oligonucleotides (about 35–50-mers), 4 base mismatches, and, optionally, (iv) other moieties or features, which are readily apparent to the skilled artisan who has read this disclosure, that facilitate using the oligonucleotide in the intended application, e.g., (i) a free hydroxyl group at the 3' terminus for applications where the one wishes to use the invention oligonucleotide as a primer in enzyme-mediated chain elongation applications, (ii) a fluorescent label, enzyme label or radiolabel to facilitate oligonucleotide detection in a particular assay, (iii) biotin linked to a convenient location such as the 5' or 3' terminus, or (iv) a free 5' hydroxyl group for enzymatic phosphorylation.

When one adapts the presently claimed compounds to uses known in the art, one will use known hybridization conditions, enzyme (such as polymerase, RNase or DNase) reaction conditions or detection technologies to design the invention oligonucleotide in a way that does not interfere with the intended use, or in a way that improves the intended use. For example, when a previously described assay or diagnostic method calls for conducting an oligonucleotide hybridization or enzyme amplification protocol at a specified temperature, one will have the option of increasing the hybridization or enzyme amplification temperature due to the presence of an invention base(s) in the oligonucleotide. Thus, one can use the enhanced binding affinity or enhanced binding specificity property of the invention oligonucleotides to increase hybridization stringency. Similarly, when one intends to use an invention oligonucleotide in a polymerase chain reaction (PCR) amplification method, one would initially test to see if the presence of an invention base at the 3' terminus improves the oligonucleotide's primer function and then adjust the reaction conditions accordingly, e.g., by altering the primer to target sequence ratio, primer concentration or by altering the temperature at which one denatures and amplifies the PCR reaction. If the presence of an invention base significantly affects polymerase-mediated primer elongation, then one could choose to design invention oligonucleotides for this use without an invention base(s) at the 3' terminal 1, 2 or 3 monomer positions. Skilled artisans routinely design diagnostic or assay protocols by testing varying temperature, salt composition and concentration, pH, oligonucleotide concentration, enzyme concentration, enzyme reaction buffer, net oligonucleotide charge, or oligonucleotide base, sugar or linkage structure during assay development.

Embodiments include a method comprising preparing a series of oligonucleotides, each having the same base sequence, which sequence contains 2 or more cytosine bases, where each member of the series contains an invention base of structure (3) in place of one or more of the cytosine residues. Such oligonucleotides typically comprise 2 to about 6 cytosine residues. One prepares oligonucleotides containing an invention base at each cytosine position and optionally one prepares oligonucleotides containing an invention base at each of two cytosine positions, at each of three cytosine positions and so forth. One uses this method to determine which oligonucleotide(s), compared to a control containing no invention base(s), has optimal properties for a desired application, e.g., hybridization affinity for use as a probe or optimal antisense activity for inhibiting target gene expression in a cell.

Structure (5) monomers, when triphosphorylated and containing $R^1$ ribose or deoxyribose derivatives that are chain terminating (e.g. where the 3' position is not hydroxyl), are useful in methods for fluorescent chain-terminating dideoxynucleotide sequencing in the same general fashion as ddNTPs having other linker-attached fluorophores.

Since oligonucleotide compounds such as those of structure (2) are capable of participating in Watson-Crick base pairing they will bind to nucleic acids and therefore are useful in detecting the presence of nucleic acids. Bases of structure (1) in such oligonucleotides will recognize guanosine as its complementary base in natural nucleic acids.

Invention oligonucleotides, including many structure (2), (2A), (2B) and (2C) oligonucleotides capable of forming high melting duplexes with complementary sequences, are useful in numerous applications, including antisense or codeblocking utilities in vivo or in vitro as well as diagnostics and probe uses. High melting duplexes are those having melting temperatures substantially above the melting temperatures of oligonucleotide or nucleic acid duplexes of the same sequence that contain the ordinary, naturally occurring bases, e.g., adenosine, cytidine, uridine, guanosine, thymidine and the like. "Substantially above" means that the derivative oligonucleotide, when hybridized with its complementary sequence, will not dissociate from the duplex until the temperature is raised from about 2 to 40° C., ordinarily about 8 to 40° C., above the dissociation temperature of the same oligonucleotide having the analogous normal A, C, U, G or T bases, but to no greater temperature than about 95° C. This is known as the D Tm. Ordinarily, D Tm is measured by comparing control oligonucleotide binding to complementary RNA or DNA with the binding of test oligonucleotide to the same RNA or DNA, following, e.g., the method described in Jones et al., "JOC" 58:2983 (1993).

Some of the invention riboside and deoxyriboside compounds are fluorescent. The compounds remain fluorescent upon incorporation into oligonucleotides and are visible intracellularly, including when bound to target sequences after direct injection or after transfection into cells in accord with known methods.

One can optionally prepare oligonucleotides having tandem arrangements of the novel bases. In general, such tandem arrangements will contain from 2 to about 10 invention polycyclic bases, usually 2, 3 or 4, which can be the same or different polycycles but generally are the same invention polycycle. They also optionally are copolymerized with purine or pyrimidine bases containing known alkynyl substitutions (e.g., U.S. Pat. Nos. 5,645,985 and 5,594,121), in particular pyrimidine bases substituted at the 5 position with a carbon atom which is bonded to another atom by a Pi bond, or the fluorescent cytosine derivatives of Inoue et al. (op cit).

The compounds of this invention, or other oligonucleotides capable of forming high melting duplexes (e.g. the Pi bonded bases discussed above), are useful in improved methods for polymerase chain reaction ("PCR") or ligase chain reaction ("LCR") amplification and detection of nucleic acids. In one embodiment, the high melting oligonucleotides are used as one or both primers in classical PCR or as probes in LCR. Particularly in PCR processes, the elevated melting temperature of duplexes with high melting primers avoids the need to thermally cycle the reaction because at these elevated temperatures (about 68 to 95° C., preferably greater than about 75° C.; the derivative primer will continue in at least some proportion to anneal to the target but extension product will not. Ordinary primers will not hybridize and the polymerase will not initiate transcription until the reaction mixture is cooled to a level at which the primer will anneal to the target sequence (usually, about 55° C.). The elevated temperature that is chosen for use with the high-melting derivative oligonucleotides (a temperature suitable for all of annealing, extension and melting) is one at which a substantial proportion of the extended primer population (about 10 to 90 mole %) is found dissociated from the target, but sufficient unextended primer is bound to permit extension. Optimally, this is about from 85 to 95° C., ordinarily 92 to 95° C. Alternatively, the optimal temperature is determined empirically by simply selecting a range of temperatures within the melting range of the extended sequence, but within the annealing range of the derivative primers, and measuring the amount of amplification product to achieve satisfactory levels for the diagnostic or preparative processes at hand. Amplification methods have been described, e.g., U.S. Pat. No. 5,667,974.

An exemplary method to use an invention oligonucleotide to amplify a nucleic acid base sequence comprises, providing an invention oligonucleotide and target nucleic acid sequence that forms a complex having a Tm of about 85 to 95° C., optionally heating the complex to about 85 to 95° C. (e.g., to a temperature within about 5° C. of the Tm) to provide a heated complex, and optionally mixing the heated complex with a DNA polymerase such as Taq polymerase or other suitable heat stable enzyme. In this method, the complex and the heated complex is typically a duplex. The polymerase reaction will contain cofactors and buffer conditions suitable for amplification purposes.

It will be understood that the optimal temperature will vary considerably depending upon the derivative bases chosen, whether they are adjacent or separated by other bases, the number of bases in the primers (the highest annealing temperatures are found with primers having greater than about 18 bases or base analogs), the proportions of pyrimidines and purines and the like. The heat stable polymerase useful in this system is for example Taq polymerase or other suitable heat stable enzyme. Thus, whatever the optimum temperature chosen, the amplification and priming reactions are conducted conventionally but at a substantially constant temperature.

Not only do the oligonucleotides of this invention facilitate PCR or LCR processes, the fluorescent properties of the primers also facilitate detection of the extension products. The extension products are readily separated from the unextended primers, e.g. on the basis of molecular weight, and detected by their fluorescence, thereby avoiding staining with agents such as ethidium bromide. In some embodiments, the fluorescence is enhanced by using NTP's comprising the fluorescent substructures of this invention in primer extension so that the fluorescent NTPs are incorporated into the extension products as well. The polycyclic substructure used in the NTP's may be the same or different than the one incorporated into the primers.

We incorporate herein all citations by reference with specificity.

The following examples further illustrate and do not limit the invention.

EXAMPLE 1

The following example shows synthesis of representative starting materials and intermediates for making invention compounds.

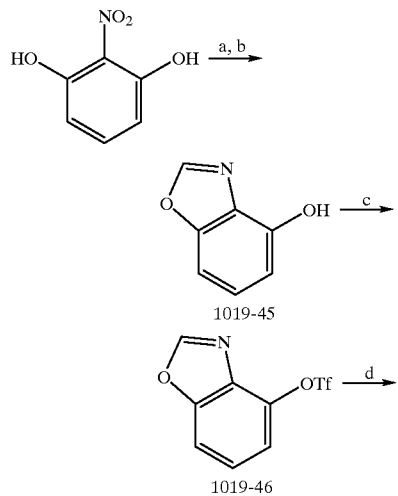

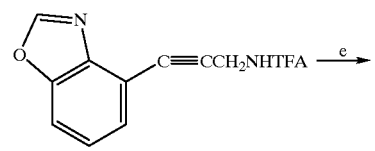

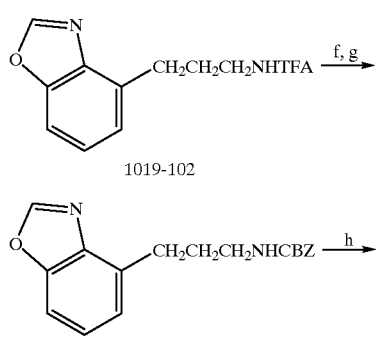

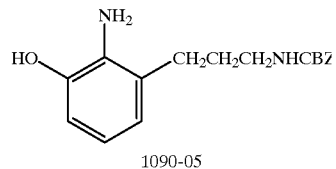

Conditions: a: $H_2$, 10% Pd/C, $CH_3OH$, RT; b: $HC(OCH_3)_3$, methanesulfonic acid, 47.8%; c: $Tf_2NPh$, $CH_2Cl_2/DMF$, $K_2CO_3$, RT, quantitative; d: $HC\equiv CCH_2NHTFA$, $Pd(Ph_3P)_4$, CuI, TEA, DMF, 60%; e: $H_2$, 10% Pd/C, $CH_3COOEt$; f: con. $NH_4OH$/Dioxane (1/1), RT; g: $PhCH_2OC(O)Cl$, pyridine; h: 3N HCl/EtOH (1/1), RT, 1 hr or 40° C., 30 min.

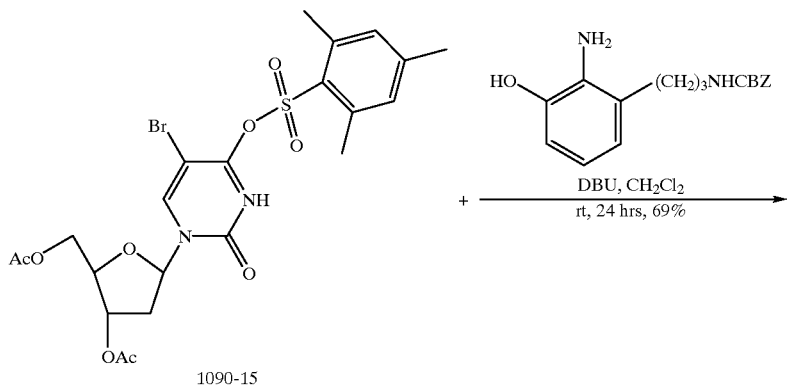

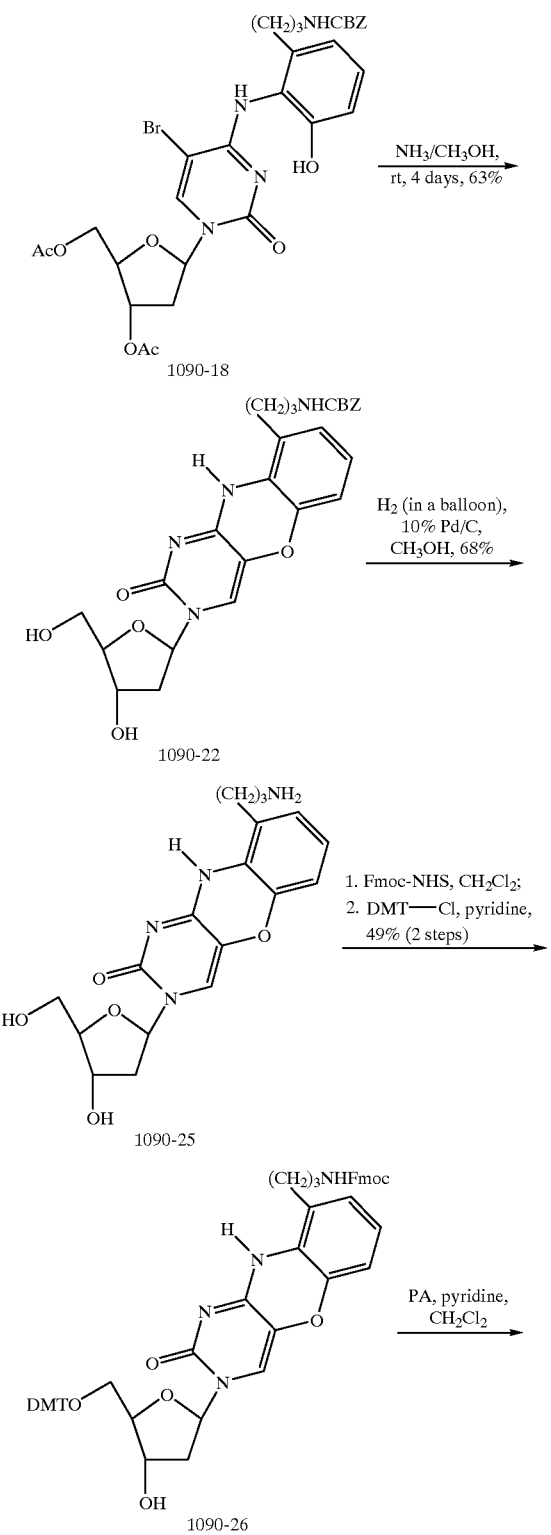

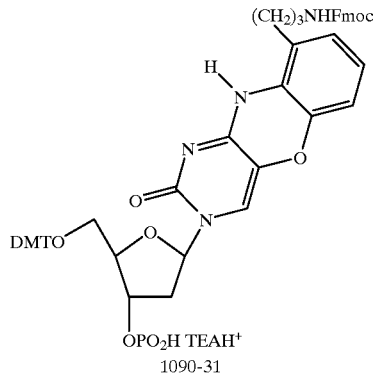

1090-31

9-(3'-Aminopropyl)phenoxazine

2-Aminoresorcinol (#1019-43): A ethanol solution (500 mL) of 2-nitroresorinol (20 g; 0.129 mmole) was hydrogenated (H₂ in balloon) in the presence of 10% Pd/C (1 g) at room temperature overnight. The catalyst was filtered off through a celite pad. The filtrate was concentrated and purified by flash column chromatography, affording 15.5g, 96% of 2-aminoresorcinol. ¹H NMR (DMSO-d₆): δ 8.80 (bs, 2H), 6.15–6.30 (m, 3H), 3.85 (bs, 2H).

Compound #1019-45: A trimethyl orthoformate solution (100 mL) of 2-aminoresorcinol (6.0 g; 48 mmole) was treated with methanesulfonic acid (4.6 g; 48 mmole). After 30 min stirring at room temperature, the reaction was cooled to 0° C. and was quenched with TEA (4.8 g; 48 mmole). The reaction mixture was concentrated and purified by column chromatography on silica gel, yielding 3.10 g of product, 47.8%. ¹H NMR (DMSO-d₆): δ 10.3 (bs, 1H), 8.53 (s, 1H), 7.18 (dd, 1H, J=8.0 Hz, J=7.8 Hz), 7.12 (d, 1H, J=8.0 Hz), 6.73 (d, 1H, J=7.8 Hz).

Compound #1019-46: A CH₂Cl₂/DMF (N,N-dimethylformamide) solution (20 mL/10 mL) of #1019-45 (2.90 g; 21.4 mmole) was stirred with solid K₂CO₃ (14.8 g; 107 mmole) at room temperature for 30 min, followed by addition of N-phenyltrifluoromethanesulfonimide (8.50 g; 23.6 mmole). The resulting mixture was stirred at room temperature overnight, then diluted with CH₂Cl₂, washed with water twice, dried, concentrated, and purified, affording 5.76 g, quantitatively, of # 1019-46. ¹H NMR (CDCl₃): δ 8.19 (s, 1H), 7.66 (d, 1H, J=8.2 Hz), 7.48 (t, 1H, J=8.2 Hz), 7.33 (d, 1H, J=8.2 Hz).

N-TFA-propargylamine (#1019-44): Propargylamine (25 g; 0.45 mmole) was dissolved in CH₃OH (500 mL), followed by addition of ethyl trifluoroacetate (84 g; 0.59 mole). The resulting mixture was stirred at room temperature overnight, then concentrated to dryness. The residue was redissolved in CH₂Cl₂ (200 mL), washed with saturated NaHCO₃ aqueous solution. The organic phase was isolated, dried, concentrated to a brown residue (liquid). The product #1019-44, 54.0 g was distilled off, 78.8%. ¹H NMR (CDCl₃): δ 6.60 (bs, 1H), 4.18 (m, 2H), 2.38 (s, 1H).

Compound #1019-97: A DMF solution (12 mL) of compound #1019-46 (4.9 g; 18.3 mmole), N-TFA-propargylamine (5.5 g; 36.7 mmole), Pd(PPh₃)₄ (4.3 g; 3.7 mmole), CuI (1.78 g; 9.3 mmole) and TEA (3.7 g; 36.7 mmole) was stirred at room temperature for 24 hours. The reaction mixture was diluted with CH₂Cl₂ (100 mL), stirred with Dowex 1×800 (HCO₃— form). The organic phase was washed with water, dried, and purified, yielding 2.94 g, 60%, of product #1019-97. ¹H NMR (CDCl₃): δ 8.18 (s, 1H), 7.62 (d, 1H, J=9 Hz), 7.48 (d, 1H, J=9 Hz), 7.36 (t, 1H, J=9Hz), 6.85 (bs, 1H), 4.51 (d, 2H, J=3 Hz).

Compound #1019-102: A ethylacetate solution (60 mL) of #1019-97 (1.7 g; 6.3 mmole) was hydrogenated in the presence of 10% Pd/C (200 mg) at room temperature. The catalyst was filtered off. The filtrate was concentrated to dryness, used for next reaction without further purification. ¹H NMR (CDCl₃): δ 8.25 (bs, 1H), 8.12 (s, 1H), 7.49 (d, 1H, J=8.2 Hz), 7.36 (dd, 1H, J=7.6 & 8.1 Hz), 7.20 (d, 1H, J=7.5 Hz), 3.25 (q, 2H), 3.07 (t, 2H, J=6.6 Hz), 2.01 (p, 2H).

Compound #1090-05A: A 1.4-dioxane solution (10 mL) of compound #1019-102 (1.0 g; 3.6 mmole) was treated with concentrated NHOH (15 mL) at room temperature for 16 hrs. The reaction mixture was concentrated to dryness. The residue was redissolved in CH₂Cl₂ (30 mL), containing TEA (0.74 g; 7.35 mmole), cooled to 0° C., followed by addition of benzyl chloroformate (0.75 g, 4.4 mmole). The resulting solution was stirred at room temperature for 4 hrs, washed with H₂O, dried and purified by flash column chromatography to give 0.81 g, 71% of #1090-05A.

Compound #1090-05: A ethanol solution (10 mL) of compound #1090-05A (0.81 g, 2.6 mmole) was treated with 3 NHCl aqueous solution (10 mL) at 40° C. for 1 hr. The reaction mixture was concentrated to dryness, azeotroped with CH₃CN three times. The crude product was used for next reaction, without further purification. ¹H NMR (CDCl₃): δ 7.25–7.40 (m, 5H), 7.20 (t, 1H), 6.78–6.90 (m, 2H), 5.07 (s, 2H), 3.17 (t, 2H, J=6.8 Hz), 2.67 (t, 2H, J=7.6 Hz), 1.79 (p, 2H).

Compound #1090-18: Compound #1090-15 has been described (Lin, "JACS" 117:3873–3874, 1995). A mixture of Compound #1090-15 (1.5 g; 2.6 mmole), #1090-05 (2.6 mmole) and DBU (0.8 g; 5.2 mmole) in CH₂Cl₂ (30 mL) was stirred at room temperature overnight. The reaction mixture was washed with 10% citric acid aqueous solution, dried and purified on silica gel column chromatography, affording 1.21 g, 69% of product. ¹H NMR (CDCl₃): δ 8.86 (s, 1H), 7.99 (s, 1H), 7.29–7.40 (m, 5H), 7.15 (t, 1H), 6.98 (d, 1H, J=8 Hz), 7.78 (d, 1H, J=7 Hz), 6.27 (t, 1H), 5.20–5.23 (m, 1H), 5.09 (s, 2H), 4.78 (bs, 1H), 4.30–4.52 (m, 3H), 3.20–3.30 (q, 2H), 2.65–2.80 (t+m, 3H), 2.10–2.20 (2 s+m, 7H), 1.80 (p, 2H).

Compound #1090-22: Compound #1019-18 (1.20 g; 1.78 mmole) was treated with saturated NH₃ in CH₃OH (200 mL) at room temperature for 5 days. The reaction mixture was concentrated to dryness and purified by flash column chromatography affording 0.63 g of product #1090-22, 70%. ¹H NMR (CDCl₃+10% CD₃OD): δ 7.30–7.38 (m, 5H), 6.81 (t, 1H, J=7.3 Hz), 6.73 (d, 1H, J=7.9 Hz), 6.60 (d, 1H), 6.20 (t, 1H), 5.10 (s, 2H), 4.36–4.40 (m, 1H), 3.94–4.0 (m, 1H), 3.70–3.90 (m, 2H), 3.23 (t, 2H), 2.58 (t, 2H), 2.30–2.40 (m, 1H), 2.10–2.24 (m, 1H), 1.70–1.82 (m, 2H).

Compound #1090-25: Compound #1090-22 (0.6 g) was dissolved in ethanol (10 mL) and was hydrogenated (H$_2$ in a balloon) in the presence of 10% Pd/C (50 mg) at room temperature for 4 hrs. The catalyst was filtered off, washed with CH$_3$OH. The filtrate was concentrated and dried to afford 0.3 g, 68% of product. $^1$H NMR (CD$_3$OD): δ 7.38 (s, 1H), 6.7–6.82 (m, 2H), 6.57 (d, 1H, J=6.3 Hz), 6.23 (dd, 1H, J=6.5 Hz, J=6.7 Hz), 4.35–4.38 (m, 1H), 3.80–3.90 (m, 1H), 3.70–3.80 (m, 1H), 2.60–2.80 (m, 4H), 2.10–2.30 (m, 2H), 1.75–1.86 (m, 2H).

Compound #1090-26: Compound #1090-25 (0.13 g, 0.34 mmole) was dissolved in DMF/CH$_2$Cl$_2$ (1 mL/3 mL), followed by addition of 9-fluorenylmethyl-N-succinimidylcarbonate (FMOC-NHS, 0.14 g; 0.41 mmole). After 1 hr of stirring at room temperature, to the reaction mixture pyridine (140 mg, 1.7 mmole), and DMT-Cl (4,4'-dimethoxytrityl chloride; 0.14 g; 0.41 mmole) were added. The resulting mixture was stirred at room temperature for 2 hrs and then diluted with CH$_2$Cl$_2$, washed with water twice. The organic phase was isolated, dried and purified by flash column chromatography on silica gel, to give 153 mg, 49%, FAB HRMS (high resolution mass spectroscopy) calculated for M+H$^+$ 899.416, found 899.366.

Compound #1090-31: Compound #1090-26 (150 mg; 0.167 mmole) in CH$_2$Cl$_2$ (2 mL) was added to a 0° C. cold CH$_2$Cl$_2$ solution (1 mL) of PA (0.25 mL of 1M CH$_2$Cl$_2$ solution, 0.25 mmole) and pyridine (66 mg, 0.83 mmole). The resulting mixture was then gradually warmed to room temperature. After 30 minutes, the reaction mixture was diluted with CH$_2$Cl$_2$, washed with 1 M TEAB aqueous solution, dried and purified on silica gel, eluted with 5% CH$_3$OH/CH$_2$Cl$_2$, then 15%, H$_2$O in CH$_3$CN. The combined fractions of product were concentrated and then partitioned between CH$_2$Cl$_2$ and 1M TEAB aqueous solution dried, yielding 180 mg of H-phosphonate derivative, quantitatively.

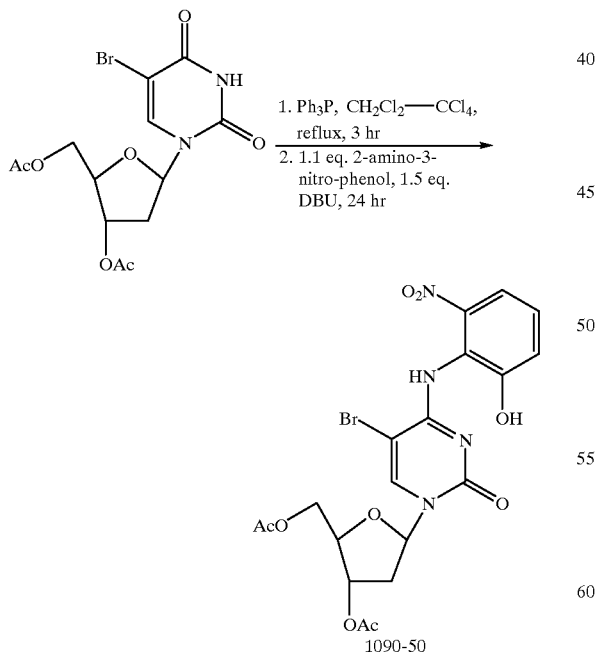

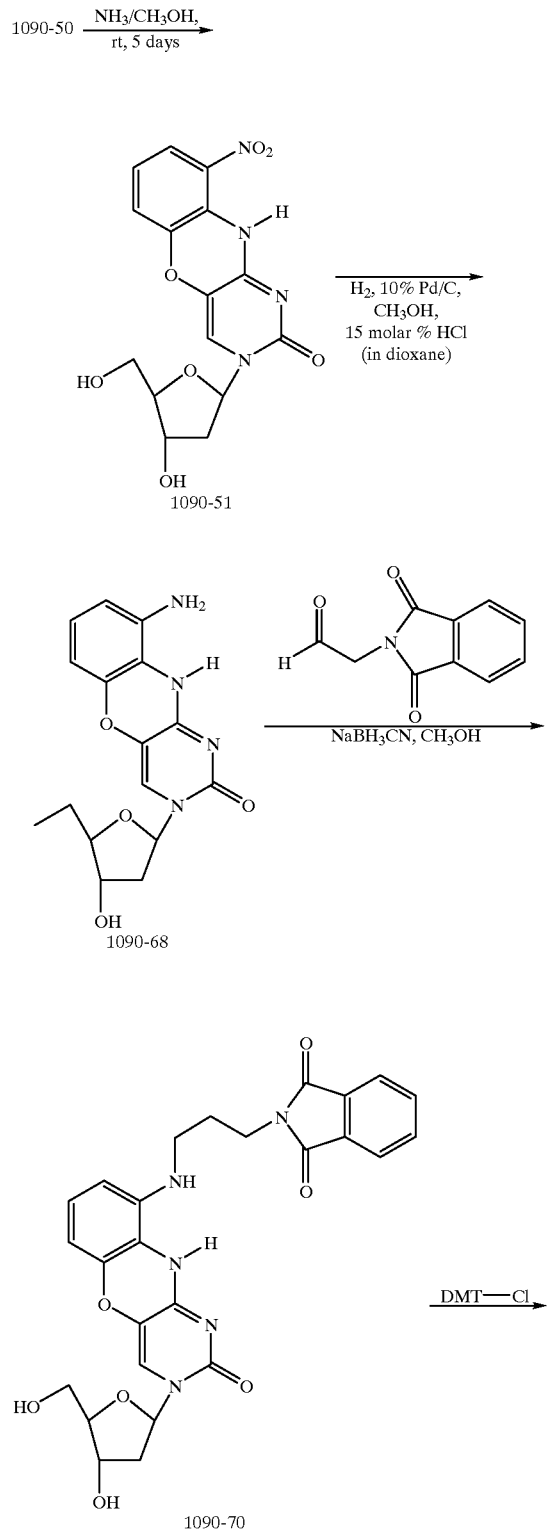

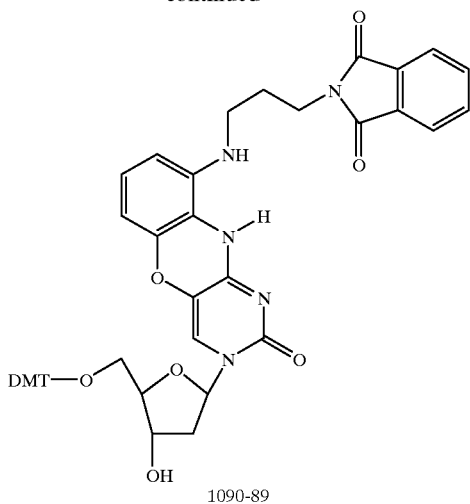

1090-89

Compound #1090-68: A CH$_2$Cl$_2$—CCl$_4$ (40 mL/40 mL) solution of 5-bromo-3'-5'-diacetyl-2'-deoxyuridine (2.0 g, 5.1 mmole) and triphenyl phosphine (2.0 g, 7.6 mmole) was heated at reflux for 3 hrs. The reaction mixture was cooled to room temperature, followed by addition of 2-amino-3-nitrophenol (0.79 g, 5.1 mmole) and DBU (1.6 g, 10 mmole). After stirring at room temperature overnight, the reaction mixture was washed with 10% citric acid aqueous solution, dried, concentrated and purified on silica gel. The isolated product contained Ph$_3$P=O, was treated with saturated NH$_3$ in CH$_3$OH for 5 days at room temperature. After removal of all solvent, the residue (crude #1090-51) was redissolved in CH$_3$OH (100 mL), and hydrogenated with H$_2$ in a balloon in the presence of 10% Pd/C and 4 N HCl in dioxane (200 mL, 0.8 mmole). After 5 hrs, the catalyst was filtered off, washed with CH$_3$OH. The filtrate was concentrated and purified by flash column chromatography to afford 0.83 g of #1090-68, in 50% yield for 3 steps. $^1$H NMR (DMSO-Cl$_6$): δ 9.6 (b, 1H), 6.56 (t, 1H, J=8.0 Hz), 6.22 (d, 1H, J=7.8 Hz), 6.10 (t, 1H, J=6.8 Hz), 5.96 (d, 1H, J=7.1 Hz), 5.17 (d, 1H), 4.92–5.08 (m, 3H), 4.16–4.20 (m, 1H), 3.70–3.80 (m, 1H), 3.50–3.60 (m, 2H), 2.0 (m, 2H).

Phthalimidoacetaldehyde #1090-70A: A mixture of N-(2-hydroxyethyl)phthalimide (90 mg; 0.47 mmole), DCC (0.15 g, 0.7 mmole), DMSO (1 mL) and dichloroacetic acid (20 mL) was stirred at room temperature for 2 hrs. The reaction mixture was diluted with CH$_2$Cl$_2$, washed with H$_2$O twice, dried and concentrated. The crude product #1090-70A contained DCC-urea by-product, was used for the next reaction without further purification.

Compound #1090-70: A DMF/CH$_3$OH (0.5 mL/2 mL) solution of #1090-68 (0.2 g, 0.42 mmole), phthalimidoacetaldehyde #1090-70A (0.47 mmole) in CH$_3$OH (2 mL) and acetic acid (85 mg, 1.4 mmole) was reacted with sodium cyanoborohydride (87 mg, 1.4 mmole) at room temperature for 4 hrs. The reaction mixture was concentrated, and purified on silica gel, yielding 243 mg, 78%, yield of compound #1154-70. $^1$H NMR (CDCl$_3$+10% DMSO-d$_6$): δ 9.45 (s, 1H), 7.60–7.68 (m, 2H), 7.50–7.58 (m, 2H), 6.51 (t, 1H, J=8.2 Hz), 6.12 (d, 1H, J=8.2 Hz), 6.06 (t, 1H, J=6.7 Hz), 5.78 (d, 1H, J=8.0Hz), 4.94 (t, 1H), 4.49–4.52 (m, 1H), 4.18–4.25 (m, 2H), 3.50–3.72 (m, 4H), 3.19–3.30 (m, 2H), 1.85–2.05 (m, 2H).

Compound #1090-89: Compound #1090-70 (35 mg; 69 mmole) was dissolved in CH$_2$Cl$_2$ (2 mL) and pyridine (0.5 mL), then reacted with DMT-Cl (28 mg, 83 mmole) at room temperature for 3 hrs. The reaction mixture was worked up and purified by flash column chromatography, yielding 44 mg, 78.6% of corresponding 5'-O-DMT-derivatives. $^1$H NMR (CDCl$_3$): δ 7.80–7.90 (m, 2H), 7.68–7.75 (m, 2H), 7.18–7.50 (m, 10H), 7.0 (b, 1H), 6.80–6.90 (m, 4H), 6.77 (t, 1H), 6.30–6.42 (m, 2H), 5.94 (d, 1H, J=8.0 Hz), 5.50 (bs, 1H), 4.50–4.60 (m, 1H), 4.10–4.18 (m, 1H), 3.86–4.0 (m, 2H), 3.25–3.30 (2s, 6H), 3.28–3.52 (m, 4H), 2.58–2.68 (m, 1H), 2.20–2.32 (m, 1H).

Compound #1090-91: Compound #1090-89 (44 mg) was converted into 3'-H-phosphonate in normal fashion, 52 mg, in 77% yield.

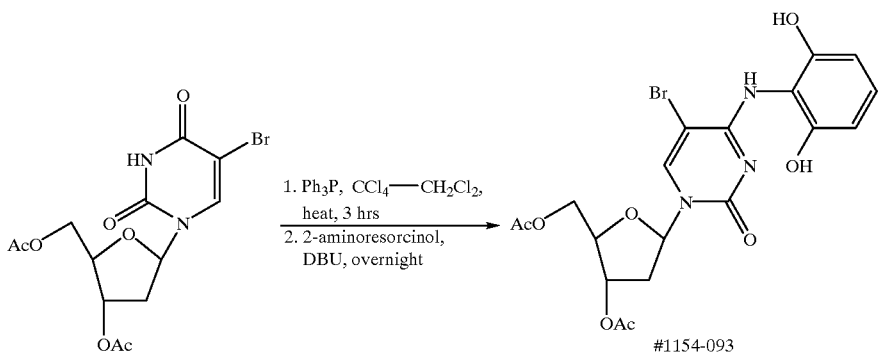

1154-093

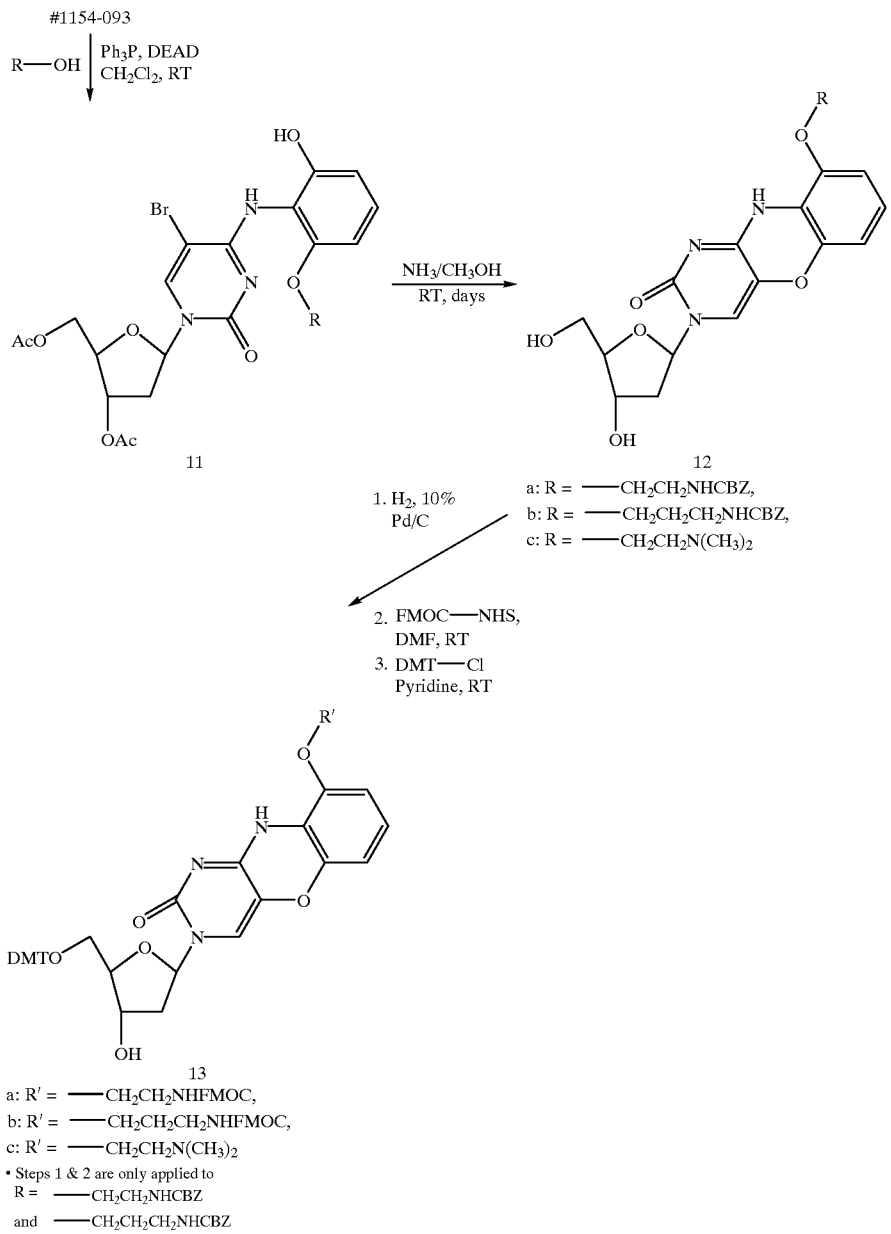

N-CBZ-3-aminopropanol (Compound #1154-74, CBZ; benzyloxycarbonyl): A $CH_2Cl_2$ solution (300 mL) of 3-aminopropanol (10 g, 0.133 mole) and TEA (20 g, 0.2 mole) was cooled to 0° C., followed by slow addition of $CH_2Cl_2$ solution (25 mL) of benzyl chloroformate (25 g, 0.147 mole). The resulting solution was gradually warmed to room temperature. The stirring was continued at room temperature overnight. The reaction mixture was washed with $H_2O$, dried and purified by flash column chromatography (on silica gel, $CH_3OH$—$CH_2Cl_2$) to yield 16.4 g, 58.9% of title compound. $^1H$ NMR ($CDCl_3$): δ 7.26–7.40 (m, 5H), 5.10 & 5.0–5.10 (s+m, 3H), 3.68 (q, 2H), 3.36 (q, 2H), 2.58 (t, 1H), 1.70 (p, 2H).

N-CBZ-2-aminoethanol (Compound #1154-104): To 0° C. cold of $CH_2Cl_2$ solution (300 mL) of 2-aminoethanol (10.8 g, 0.177 mole) and TEA (26.8 g; 0.265 mole) was added slowly a $CH_2Cl_2$ solution (50 mL) of benzyl chloroformate (33.2 g, 0.194 mole). After complete addition, the resulting solution was gradually warmed to room temperature and stirring was continued at room temperature overnight. The reaction was worked up and purified by flash column chromatography on silica gel, affording 22.8 g in 66% yield of title compound. $^1H$ NMR ($CDCl_3$): δ 7.34–7.40 (m, 5H), 5.20–5.32 (m, 1H), 5.14 (s, 2H), 3.74 (q, 2H), 3.37 (q, 2H), 2.38 (bs, 1H).

3'-5' -Diacetyl-$N^4$-(2'',6''-dihydroxyphenyl)-2'-deoxy-5-bromo-cytidine (Compound #1154-093): A $CCl_4$—$CH_2Cl_2$ solution (150 mL—150 mL) of 5-bromo-3'-5'-diacetyl-2'-deoxyuridine (15 g, 38.3 mmole) and $Ph_3P$ (15 g, 57.5 mmole) was heated at reflux under $N_2$ for 3 hrs. The reaction mixture was cooled to room temperature, followed by addition of 2-amino-resorcinol (5.2 g, 42 mmole) and DBU (8.7 g, 57.5 mmole). The resulting solution was stirred at room temperature overnight. The reaction mixture was concentrated to about ½ volume, then poured into citric acid aqueous solution (7.5 g in 300 mL $H_2O$) with vigorously stirring. The precipitate was filtered off, washed with H₂O, CH₂Cl₂ then CH₃CN, dried in a vacuum oven overnight, weighed 12.9 g, 67.8% yield of title compound. ¹H NMR (DMSO-d₆): δ 9.63 (s, 2H), 8.21 (s, 1H), 8.0 (s, 1H), 6.89 (t, 1H, J=8.1 Hz), 6.33 (d, 2H, J=8.1 Hz), 6.10 (t, 1H, J=7.4 Hz), 5.10–5.17 (m, 1H), 4.12–4.30 (m, 3H), 2.30–2.40 (m, 2H), 2.06 &2.03 (2s, 6H).

General procedure for synthesis of compounds 11a–11c and 12a–12c: Compounds 11a–11c: To a CH₂Cl₂ solution of proper protected amino alcohol, Ph₃P (1.5 eq) and diethyl azodicarboxylate (DEAD, 1.5 eq), was added compound #1154-093 (1 eq). The resulting mixture was stirred at room temperature overnight. The reaction mixture was washed with H₂O, dried and purified by a silica gel (eluted with CH₃OH—CH₂Cl₂) to yield compound 11a–11c, normally they contaminated with Ph₃P=O. However, the crude compound 11a–11c was directly used for compounds 12a–12c without further purification.

Compound 12a–12c: Crude compound 11a–11c was treated with saturated NH₃ in CH₃OH at room temperature for 1–3 days. After removal of solvent, the reaction mixture was purified by flash column chromatography on silica gel (eluted with CH₃OH—CH₂Cl₂), to yield compounds 12a–12c.

Compound 12a (1154-106, 1154-111): Compound 12a (2.5 g, 40.8%, 2 steps) was prepared from 1154-093 (6.0 g, 12 mmole) and 1154-104 (3.0 g, 15.3 mole). ¹H NMR (DMSO-d₆): δ 9.82 (bs, 1H), 7.81 (bs, 1H), 7.69 (bs, 1H), 7.25–7.36 (m, 5H), 6.82 (t, 1H, J=8.2 Hz), 6.60–6.80 (m, 2H), 6.46 (d, 1H, J=8.2 Hz), 6.14 (t, 1H, J=6.7 Hz), 5.22 (d, 1H), 5.06–5.13 (s+s, 3H), 4.20–4.25 (m, 1H), 3.94–4.0 (m, 2H), 3.79–3.81 (m, 1H), 3.58–3.65 (m, 2H), 3.40–3.50 (m, 2H), 1.98–2.20 (m, 2H).

Compound 12b: Compound 12b (0.30 g; 57.6%) was prepared from 1154-93 (0.5 g; 1.0 mmole) and compound 1154-074 (0.31 g; 1.5 mmole). ¹H NMR (CD₃OD): δ 7.65 (s, 1H), 7.24–7.36 (m, 5H), 6.79 (t, 1H, J=8.6 Hz), 6.54 (d, 1H, J=8.2 Hz), 6.36 (d, 1H, J=8.2 Hz), 6.23 (t, 1H), 5.06 (s, 2H), 4.38–4.45 (m, 1H), 3.92–4.11 (m, 3H), 3.81 (q, 2H), 3.38 (t, 2H), 2.30–2.40 (m, 1H), 2.10–2.22 (m, 1H).

Compound 11c: Compound 11c (86 mg; 37.7%) was prepared from Compound #1154-093 (200 mg, 0.4 mmole) and N,N-dimethylaminoethanol (43 mg, 0.48 mmole). ¹H NMR (CDCl₃): δ 10.9 (s,1H), 8.49 (s, 1H), 7.97 (s, 1H), 7.11 (t, 1H, J=8.2 Hz), 6.77 (d, 1H, J=8.2 Hz), 6.55 (d, 1H, J=8.0 Hz), 6.32 (dd, 1H), 5.23–5.27 (m, 1H), 4.40–4.46 (m, 2H), 4.33–4.37 (m, 1H), 4.20 (t, 2H, J=5.5 Hz), 2.70–2.80 (m+t, 3H), 2.30 (s, 6H), 2.20 (s, 3H), 2.10–2.20 (m+s, 3H).

Compound 13c: Compound 11c (130 mg, 228 mmole) was treated with saturated NH₃ in CH₃OH (30 mL). After 2 days at room temperature the reaction mixture was concentrated to dryness to give crude 12c. The crude 12c was then dissolved in pyridine (2 mL) containing TEA (89 mg, 1.2 mmole), followed by addition of DMT-Cl (115 mg, 340 mmole). After 2 hrs at room temperature, the reaction mixture was concentrated, partitioned between CH₂Cl₂ and saturated NaHCO₃ aqueous solution, dried and purified on silica gel, eluted with 5% CH₃OH/CH₂Cl₂, then 10% CH₃OH/CH₂Cl₂ to yield compound 13c, 60 mg, 34% yield. ¹H NMR (CDCl₃): δ 7.20–7.50 (m, 10H), 6.86 (dd, 4H), 6.75 (t, 1H, J=8.2 Hz), 6.55 (d, 1H, J=8.3 Hz), 6.33 (t, 1H, J=6.1 Hz), 6.28 (d, 1H, J=7.9 Hz), 4.52–4.60 (m, 1H), 4.14 (q, 1H), 4.0–4.10 (m, 2H), 3.77 & 3.79 (2s, 6H), 3.32–3.45 (m, 2H) 2.62–2.74 (m, 3H), 2.39 (s, 6H), 2.20–2.34 (m, 1H).

Compound 13a (1154-175): A methanol solution (150 mL) of compound 12a (1154-111, 2.2 g, 4.3 mmole) was hydrogenated (H₂ in a balloon) in the presence of 10% Pd/C at room temperature overnight. The catalyst was filtered off, washed with CH₃OH. The filtrate was concentrated to dryness. The crude unprotected 12a derivative was dissolved in DMF/CH₂Cl₂ (10 mL/5 mL), and reacted with FMOC-NHS (1.73 g, 5.1 mmole) at room temperature for 1 hr. The reaction mixture was diluted with CH₂Cl₂ (50 mL), containing pyridine (1.0 g, 12.7 mmole), followed by addition of DMT-Cl (1.8 g, 5.3 mmole). After 2 hrs the reaction mixture was worked up and purified by flash column chromatography, affording 2.87 g, 73% of compound 13a. FAB HRMS calculated for $C_{53}H_{49}N_4O_{10}$ (M+H⁺) 901.345, found 901.344.

Compound 13b: A ethanol solution (15 mL) of compound 12b (1154-077) was hydrogenated (H₂ in a balloon) in the presence of 10% Pd/C at room temperature for 4 hrs. Catalyst was filtered off. The filtrate was concentrated to yield unprotected 12b derivative. Unprotected 12b derivative (125 mg, 0.32 mmole) was dissolved in DMF (2 mL) and reacted with FMOC-NHS (130 mg, 0.38 mmole) at room temperature for 1 hr. The reaction mixture was diluted with CH₂Cl₂ (5 mL) containing pyridine (132 mg, 1.7 mmole), followed by addition of DMT-Cl (135 mg, 0.38 mmole). After 2 hrs, the reaction mixture was diluted with CH₂Cl₂ (10 mL), washed with H₂O, dried and purified by flash column chromatography to give compound 13b, 86 mg, 29% yield. FAB HRMS calculated for $C_{54}H_{51}N_4O_{10}$ (M+H⁺) 915.360, found 915.361.

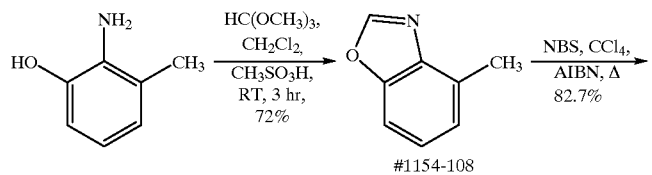

1154-108

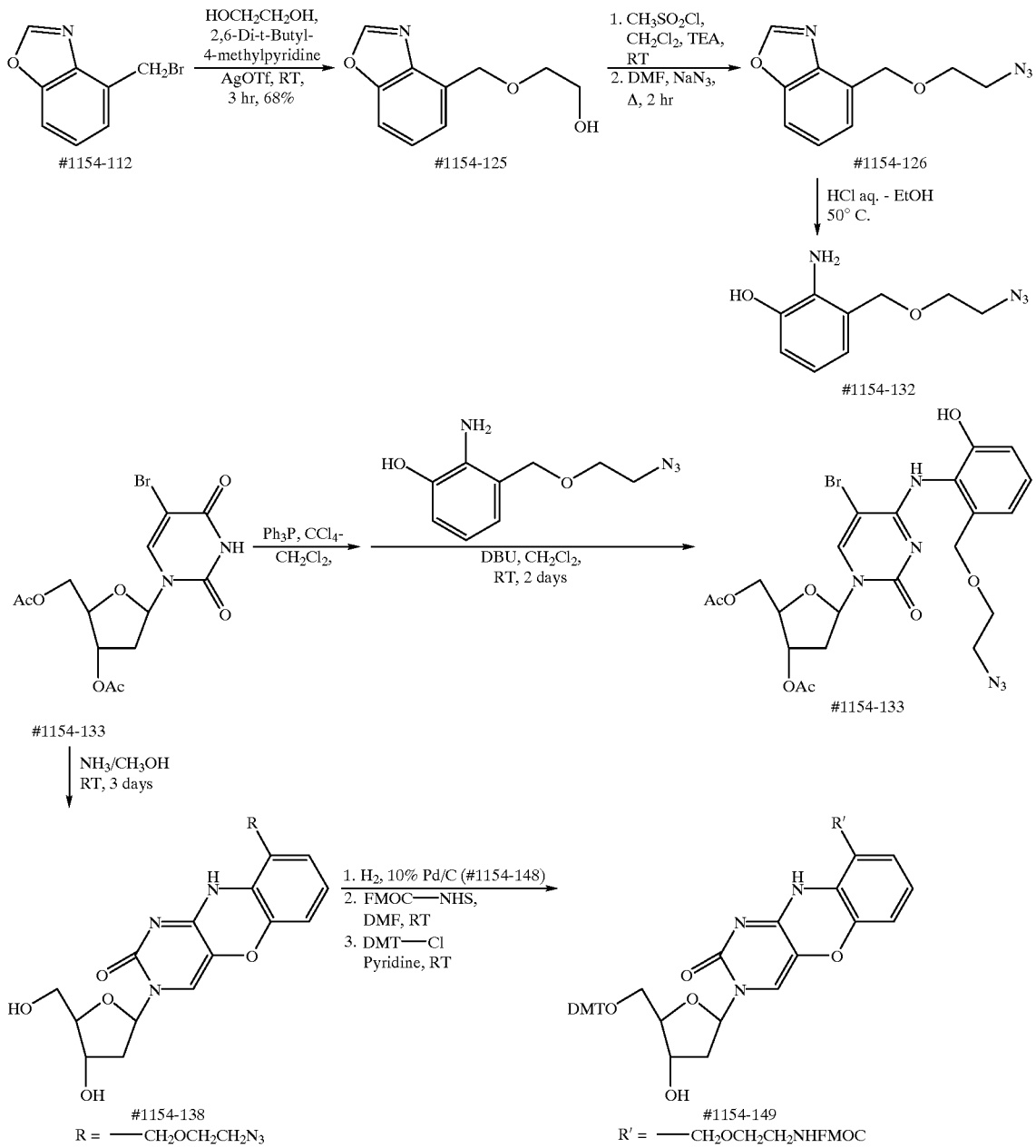

Compound #1154-108: 2-Amino-m-cresol (2.1 g, 17.6 mmole) was dissolved in trimethylorthoformate (15 mL), followed by addition of methanesulfonic acid (0.32 g, 3.4 mmole, 20 molar %). The resulting solution was stirred at room temperature for 3 hrs. The reaction mixture was neutralized with TEA (0.4 g, 4.1 mmole), concentrated and purified on silica gel, eluted with 2% $CH_3OH/CH_2Cl_2$, affording 1.6 g, 72% yield. $^1H$ NMR ($CDCl_3$): δ 8.10 (s, 1H), 7.43 (d, 1H, J=8.2 Hz), 7.31 (dd, 1H, J=7.3 Hz, J=8.2 Hz), 7.20 (d, 1H, J=7.3 Hz), 2.68 (s, 3H).

Compound #1154-112: Compound #1154-108 (4.3 g, 32 mmole) was dissolved in $CCl_4$ (50 mL), followed by addition of N-bromosuccimide (6.3 g, 35 mmole) and AIBN (240 mg). The resulting mixture was refluxed for 2 hrs under $N_2$. The reaction mixture was washed with $H_2O$, dried, concentrated and purified by flash column chromatography on silica gel, eluted with 2% $CH_3OH/CH_2Cl_2$, affording 5.67 g. of product, 82.7%. $^1H$ NMR ($CDCl_3$): δ 8.16 (s, 1H), 7.55 (d, 1H), 7.40–7.50 (m, 2H), 4.90 (s, 2H).

Compound #1154-125: A $CH_2Cl_2$ solution (20 mL) of Compound #1154-112 (0.28 g, 1.3 mmole), ethylene glycol (0.82 g, 13.2 mmole), silver triflate (0.5 g, 1.95 mmole) and 2,6-di-t-butyl-4-methylpyridine (0.52 g, 2.6 mmole) was stirred at room temperature for 3 hrs. The precipitate was filtered off, washed with $CH_2Cl_2$. The filtrate was washed with $H_2O$, dried, concentrated and purified on silica gel, eluted with 3% $CH_3OH/CH_2Cl_2$, affording 0.17 g, 68% of product #1154-125. $^1H$ NMR ($CDCl_3$): δ 8.14 (s, 1H), 7.55 (d, 1H), 7.36–7.40 (m, 2H), 4.97 (s, 2H), 3.70–3.85 (m, 4H), Compound #1154-126: Compound #1154-125 (170 mg, 0.88 mmole) was dissolved in $CH_2Cl_2$ (5 mL) containing TEA (0.27 g, 2.6 mmole) and treated with $CH_3SO_2Cl$ (0.15 g, 1.32 mmole). After 30 min at room temperature, the reaction mixture was washed with $H_2O$, dried and concentrated. The residue was dissolved in DMF (2 mL) followed by addition of sodium azide (86 mg, 1.3 mmole). The resulting solution was heated at reflux for 2 hrs. The reaction mixture was then partitioned between $CH_2Cl_2$ and water. The organic phase was isolated, dried and purified on silica gel, eluted with 1% $CH_3OH/CH_2Cl2$, to afford #1154-126, 162 mg, 84%. $^1H$ NMR ($CDCl_3$): $\delta$ 8.10 (s, 1H), 4.99 (s, 2H), 3.76 (t, 2H, J=4.8 Hz), 3.45 (t, 2H, J=4.6 Hz).

Compound #1154-132: Compound #1154-126 (1.1 g, 5.0 mmole) was treated with 3N HCl aqueous solution (10 mL) and ethanol (10 mL) at 50° C. for 1 hr. The reaction mixture was concentrated to dryness, azeotroped with $CH_3CN$ three times, used for next reaction without further purification. $^1H$ NMR (DMSO-$d_6$): $\delta$ 10.6 (bs), 6.85–7.20 (m, 3H), 4.60–4.70 (m, 2H), 3.60–3.72 (m, 2H), 3.50–3.60 (m, 2H).

Compound #1154-133: 5-Bromo-3',5'-diacetyl-2'-deoxyuridine (0.98 g, 2.5 mmole) and $Ph_3P$ (0.8 g, 3.0 mmole) were dissolved in $CCl_4/CH_2Cl_2$ (10 mL/10 mL), and were heated at reflux for 3 hrs. The reaction mixture was cooled to room temperature, followed by addition of #1154-132 (0.62 g, HCl salt, 2.5 mmole) and DBU (0.78 g, 5.1 mmole). The resulting mixture was then stirred at room temperature for 2 days, washed with 5%, citric acid aqueous solution, dried, concentrated and purified on silica gel. The isolated product contained $Ph_3P=O$, without further purification and used for next reaction.

Compound #1154-138: The crude #1154-133 (Theoretically 2.5 mmole) was treated with saturated $NH_3$ in $CH_3OH$ at room temperature for 3 days, concentrated to dryness, and purified in silica gel, yield 0.28 g of 28% yield of product (2 steps). $^1H$ NMR ($CD_3OD$): $\delta$ 7.56 (bs, 1H), 6.78–6.85 (m, 2H), 6.64–6.70 (m, 1H), 6.19 (t, 1H, J=6.4 Hz), 4.54 (s, 2H), 4.35–4.40 (m, 1H), 3.88–3.94 (m, 1H), 3.60–3.85 (m, 4H), 3.62 (t, 2H), 2.22–2.35 (m, 1H), 2.10–2.20 (m 1H).

Compound #1154-148: A $CH_3OH$ solution (25 mL) of Compound #1154-138 (160 mg, 0.38 mmole) was hydrogenated ($H_2$ in a balloon) in the presence of 10% Pd/C at room temperature for 2 hrs. The catalyst was filtered off, washed with $CH_3OH$. The filtrate was concentrated to dryness to afford #1154-148. $^1H$ NMR ($CD_3OD$): $\delta$ 7.63 (s, 1H), 6.81–6.86 (m, 2H), 6.70–6.74 (m, 1H), 6.22 (t, 1H), 4.65 (s, 2H), 4.35–4.40 (m, 1H), 3.89–3.93 (m, 1H), 3.68–3.84 (m, 2H), 3.55 (t, 2H), 2.80–2.90 (m, 2H), 2.25–2.36 (m, 1H), 2.10–2.21 (m, 1H).

Compound #1154-149: A DMF solution (2 mL) of compound #1154-148 (170 mg, 0.43 mmole) was treated with FMOC-NHS (150 mg, 0.52 mmole). After 2 hr reaction at room temperature the reaction mixture was diluted with $CH_2Cl_2$ (10 mL) containing pyridine (0.7 g, 8.7 mmole), followed by addition of DMT-Cl (0.22 g, 0.65 mmole). After 1 hr, the reaction was worked up and purified by flash column chromatography, to yield 232 mg, 58.2% of 5'-O-DMT-N-FMOC derivative #1154-149. FAB HRMS calculated for $C_{54}H_{51}N_4O_{10}$ (M+H$^+$) 915.360, found 915.359.

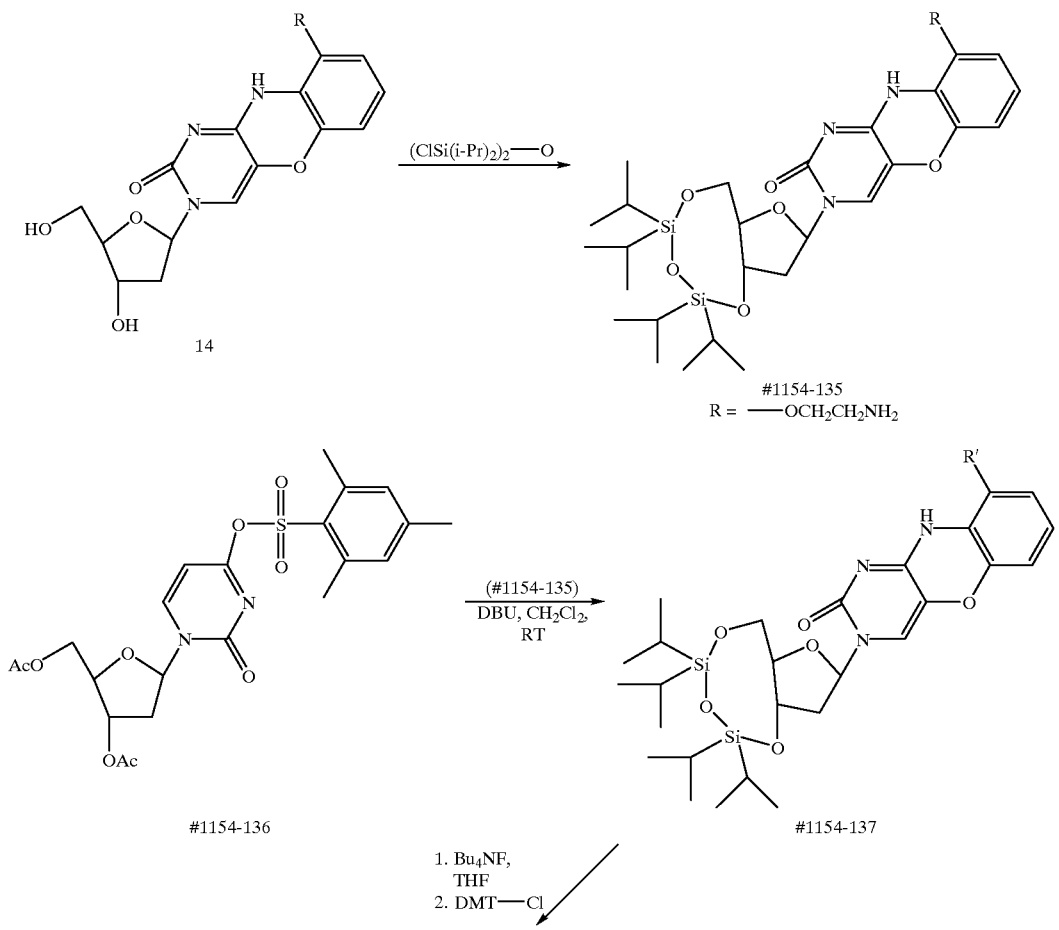

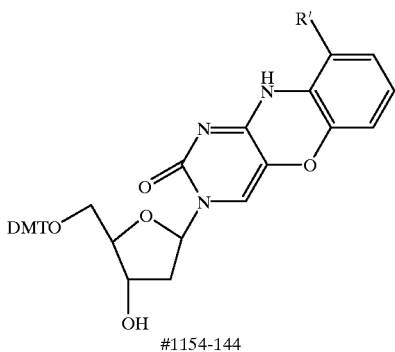

1154-144

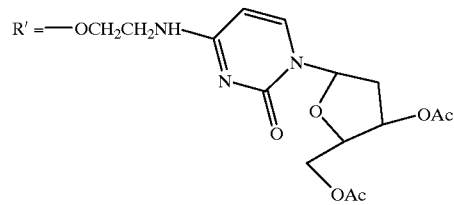

R' = —OCH$_2$CH$_2$NH—

3'-5'-Diacetyl-O$^4$-sulfonyl-2'-deoxyuridine (#1154-136): A CH$_2$Cl$_2$ solution (10 mL) of 3',5'-diacetyl-2'-deoxyuridine (0.76 g, 2.4 mmole), 2-mesitylenesulfonyl chloride (1.0 g, 4.8 mmole), TEA (1.23 g, 12.1 mmole) and catalytic amount of DMAP (0.1 g) was stirred at room temperature overnight. The reaction mixture was diluted with CH$_2$Cl$_2$, washed with 5% citric acid aqueous solution, dried and purified on silica gel, eluted with CH$_2$Cl$_2$, 35% ethyl acetate in CH$_2$Cl$_2$, to give the title compound, 0.76 g in 63% yield. $^1$H NMR (CDCl$_3$): δ 8.0 (d, 1H, J=9 Hz), 6.99 (s, 1O 2H), 6.13 (d, 1H, J=9 Hz), 6.07 (t, 1H, J=6.0 Hz), 5.15–5.20 (m, 1H), 4.33 (s, 3H), 2.70–2.85 (m+s, 7H), 2.73 (s, 3H), 2.09 (s, 3H), 1.98–2.07 (m+s, 4H).

3'-5'-O-(1,1,3,3-Tetraisopropyl-1,3-disiloxyanediyl)-9"-(aminoethoxy)phenoxazine (#1154-135): Compound 14 (see preparation of 12a and 13a) was dissolved in DMF/pyridine (2 mL/2 mL) followed by addition of 1,1,3,3-tetraisopropyl-dichlorodisilane (0.28 g, 0.91 mmole). The stirring was continued at room temperature for 3 hr. The reaction mixture was concentrated to dryness. The residue was used for next reaction without further purification.

Compound #1154-137: A CH$_2$Cl$_2$ solution (10 mL) of compound #1154-136 (0.3 g, 0.61 mmole), compound #1154-135 (crude, 0.61 mmole), and DBU (0.46 g, 3.0 mmole) was stirred at room temperature overnight. The reaction mixture was washed with 5% citric acid aqueous solution, dried, and purified by flash column chromatography (silica gel, CH$_3$OH/CH$_2$Cl$_2$), to give 0.21 g, 38% of product #1154-137. FAB LRMS calculated for C$_{42}$H$_{61}$N$_6$O$_{13}$Si$_2$ (M+H$^+$) 912, found 913.

Compound #1154-144: Compound #1154-137 (0.20 g, 0.22 mmole) in THF 1 mL, was treated with 1 M Bu$_4$NF in CH$_2$Cl$_2$ solution (0.87 mL, 0.87 mmole) at room temperature for 30 min, then concentrated to dryness. The residue was redissolved in CH$_2$Cl$_2$ (5 mL) containing pyridine (173 mg; 2.2 mmole), followed by addition of DMT-Cl (330 mg, 1 mmole). After 2 hrs, the reaction mixture was washed with saturated NaHCO$_3$ aqueous solution, dried, and purified by flash column chromatography (silica gel, CH$_3$OH/CH$_2$Cl$_2$) to yield 0.14 g, 65% of product #1154-144. FAB HRMS calculated for C$_{51}$H$_{53}$N$_6$O$_{14}$ (M+H$^+$) 973.362, found 973.364.

EXAMPLE 2

Antisense inhibition of T-antigen expression. The tested DNA oligonucleotide analogs, had the base sequence shown in Table I below. This sequence is complementary to a the 12 base RNA sequence expressed by the large SV40 virus large T antigen gene, 5' GTA GTG AGG AGG 3' (SEQ ID NO. 1). In the tested oligonucleotides, which are shown in Table I, each linkage was a phosphorothioate linkage and all sugars were 2'-deoxyribose.

The tested oligonucleotides had the base sequences shown in Table I. In the Table I oligonucleotides, bases were designated as follows.

| Base abbreviation | base |
|---|---|
| C | 5-methylcytosine |
| U | 5-(1-propynyl)uracil |
| A | adenine |
| T | thymine |
| D | 5-(1-propynyl)cytosine |
| Z | structure (58) |
| V | structure (61) |
| X | structure (57) |
| Y | structure (60) |

Structures of tricyclic bases described in this example and in following examples are as follows.

(55)

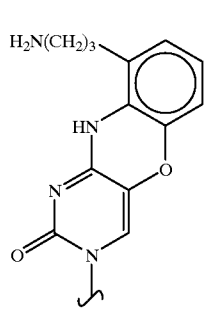

(56) 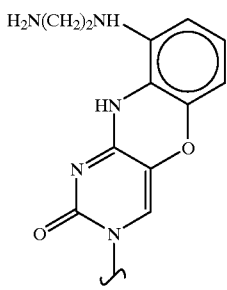

(57) 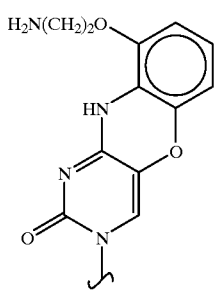

(58) 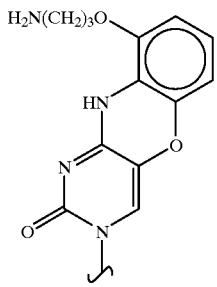

(59) (CH₃)₂N(CH₂)₂O-...

(60) 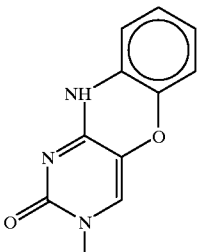

Phenoxazine Tricyclic Cytidine

(61) 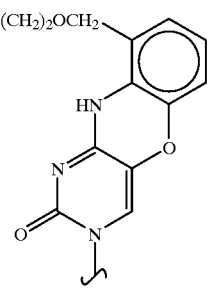

(65) 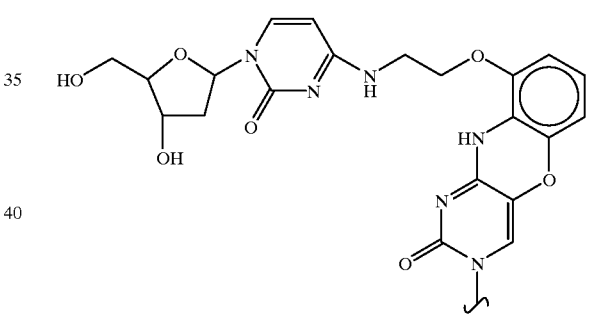

The $T_m$ values obtained from the RNA hybrids and the intracellular $IC_{50}$ values for T-antigen inhibition derived from microinjection analysis are shown below. In all cases, β-galactosidase inhibition was concurrently tested as an internal control and we saw no inhibition at 5 μM, the highest concentration tested. We measured inhibition of T antigen expression in CV-1 cells in tissue culture essentially as described (Wagner et al., "Science" 260:1510–1513 1993). We measured the $\Delta T_m$ (° C.) values relative to control ODN1 essentially as described (Jones et al. "JOC" 58:2983 1993).

TABLE I

| ODN # | BASE | ODN sequence 5' to 3' | | ΔT$_m$ (° C.)* | IC$_{50}$ (μM) |
|---|---|---|---|---|---|
| 1 | C control | CCU-CCU-CAC-UAC | SEQ ID NO. 2 | (65.0) | 0.5–1.0 |
| 2 | D control | DDU-DDU-DAD-UAD | SEQ ID NO. 3 | +13.0 | 0.25 |
| 3 | (57) | XCU-CCU-CAC-UAC | SEQ ID NO. 4 | +2.5 | 1.0 |
| 4 | (57) | CXU-CCU-CAC-UAC | SEQ ID NO. 5 | +9.5 | 0.05 |
| 5 | (57) | CCU-XCU-CAC-UAC | SEQ ID NO. 6 | +6.5 | 0.1 |
| 6 | (57) | CCU-CXU-CAC-UAC | SEQ ID NO. 7 | +9.0 | 0.05 |
| 7 | (57) | CCU-CCU-XAC-UAC | SEQ ID NO. 8 | +6.5 | 0.05–0.1 |
| 8 | (57) | CCU-CCU-CAX-UAC | SEQ ID NO. 9 | +5.0 | 0.1 |
| 9 | (57) | CCU-CCU-CAC-UAX | SEQ ID NO. 10 | +5.5 | 2.0 |
| 10 | mismatch | CCX-CCU-UAC-UAC | SEQ ID NO. 11 | −12.5 | >0.5 |
| 11 | T control | CCT-CCT-CAC-TAC | SEQ ID NO. 12 | −11.0 | >1.0 |
| 12 | T-(57) | CCT-CCT-XAC-TAC | SEQ ID NO. 13 | −2.0 | 0.25 |
| 16 | D | CCU-CCU-DAC-UAC | SEQ ID NO. 14 | 0 | 0.5–1 |
| 17 | (60) | CCU-CCU-YAC-UAC | SEQ ID NO. 15 | +0.5 | >0.5 |
| 18 | (58) | CCU-CCU-ZAC-UAC | SEQ ID NO. 16 | +5.0 | 0.3 |
| 19 | (61) | CCU-CCU-VAC-UAC | SEQ ID NO. 17 | +1.0 | 0.35 |

*ΔT$_m$ Relative to control ODN1

The results above show that the presence of an invention base elicits potent and specific antisense inhibition of target gene expression (compare ODN1 vs. ODN4 and ODN6). Incorporation of one invention base at an internal C position resulted in a potency enhancement which exceeds that obtained from the substitution of seven 5-(1-propynyl) cytosine bases for 5-methylcytosine (compare ODN2 and ODN4). The ODN12 results showed that oligonucleotides containing limited base substitutions and only a single invention base may have significant antisense potency. Phosphorothioate linked oligodeoxynucleotides containing propynyl-substituted pyrimidine bases were previously the most potent class of antisense agents that workers had described.

Oligonucleotides containing a base of structure (3) at an internal position in the oligonucleotide where R$^2$ was (a) the (S) isomer of —O—CH$_2$—C*H(CH$_3$)—NH$_2$ or (b) the (R) isomer of —O—CH$_2$—C*H(CH$_3$)—NH$_2$ were prepared and tested for binding affinity in a similar manner. Both oligonucleotides had an increased binding affinity compared to the control oligonucleotide.

EXAMPLE 3

Antisense inhibition of p27$^{kip1}$ expression. The sequence of ODN13 was 5' UGGCUCUCCUGCGCC 3' (SEQ ID NO. 18) and it contained phosphorothioate linkages, all sugars were 2'-deoxyribose, all G positions contained guanine, all U positions contained 5-(1-propynyl)uracil and all C positions contained 5-(1-propynyl)-cytosine. ODN14 had the same sequence and base composition as ODN13, except that all C positions contained 5-methylcytosine instead of 5-(1-propynyl)cytosine and thymidine instead of 5-(1-propynyl) uracil. ODN15 had the same sequence and base composition as ODN14, except that the 9th C position from the 5' end contained a (57) base instead of 5-methylcytosine. Each ODN was tested for its capacity to inhibit p27 gene expression in CV-1 cells in cell culture using cationic lipid to deliver the oligonucleotides into the cells, essentially as described (Coats "Science" 272:877–880, 1996).

| ODN | IC$_{50}$(nM) |
|---|---|
| 13 | 10 |
| 14 | >20 |
| 15 | <5 |

The results showed that ODN15 containing one (57) base is more potent than the all-propyne derivative ODN13. Previously, phosphorothioate-linked oligonucleotides containing 5-1(propynyl)-modified pyrimidine bases were the among the most potent reported class of antisense agents.

ODN13 was tested in rats and, in a 10 day toxicological evaluation, it was found that the MTD (maximum tolerated dose) was 0.6 mg/kg/d i.v. ODN15 was tested in the same manner with no toxicity observed at a dose of 6.0 mg/kg/d i.v.

EXAMPLE 4

Increased oligonucleotide binding affinity and specificity. We made a 10-mer oligonucleotide, ODN22, having the base sequence, 5' TCTCCCTCTC 3' (SEQ ID NO. 19). ODN22 contained only phosphorothioate linkages, all sugars were 2'-deoxyribose, bases designated T were thymine, bases designated C were 5-methylcytosine. ODN23 was the same as ODN22, except that the 5th base position from the 5' end contained 5-(1-propynyl)cytosine (base designated "D" in Table IV). ODN24 was the same as ODN22, except that the 5th base position from the 5' end contained a structure (60) base. ODN25 was the same as ODN22, except that the 5th base position from the 5' end contained a structure (55) base. ODN26 was the same as ODN22, except that the 5th base position from the 5' end contained a structure (57) base. ODN27 was the same as ODN22, except that the 5th base position from the 5' end contained a structure (59) base. ODN28 was the same as ODN22, except that the 5th base position from the 5' end contained a structure (58) base. ODN29 was the same as ODN22, except that the 5th base position from the 5' end contained a structure (61) base. ODN30 was the same as ODN22, except that the 5th base position from the 5' end contained a structure (65) base.

We measured the T$_m$ (° C.) of ODN22–ODN30 using 4 different oligonucleotides: A complementary RNA oligonucleotide (ODN31), an RNA oligonucleotide (ODN32) having adenine at the 11th position from its 5' end, i.e., a single A: test base mismatch, a complementary DNA oligonucleotide (ODN33), and a DNA oligonucleotide (ODN34)

having adenine at the 11th position from its 5' end. We measured the $\Delta T_m$ (° C.) values are relative to control ODN22 essentially as described (Jones "JOC" 58:2983 1993). The results are shown in Table II.

TABLE II

Thermal Denaturation Data for 9-Modified Phenoxazine ODNs
Target DNA (33)/RNA (31): 5'-AAA-AAG-AGA-GGG-AGA (SEQ ID NO. 21, 22)
Target DNA (34)/RNA (32): 5'-AAA-AAG-AGA-GAG-AGA (SEQ ID NO. 23, 24)

| ODN | test base | 31 | ΔTm* | 32 | ΔTm (31–32) | 33 | ΔTm* | 34 | ΔTm (33–34) |
|---|---|---|---|---|---|---|---|---|---|
| 22 | C (control) | 61.5 | — | 42.5 | 19.0 | 50.5 | — | 32.0 | 18.5 |
| 23 | D (control) | 65.0 | 3.5 | 44.5 | 20.5 | 54.0 | 3.5 | 33.0 | 21.0 |
| 24 | (60) (control) | 66.5 | 5.0 | 50.0 | 16.5 | 57.0 | 6.5 | 44.5 | 12.5 |
| 25 | (55) | 73.5 | 12.0 | 56.0 | 17.5 | 63.5 | 13.0 | 44.0 | 19.0 |
| 26 | (57) | 77.5 | 16.0 | 52.0 | 25.5 | 68.5 | 18.5 | 43.0 | 25.5 |
| 27 | (59) | 74.0 | 12.5 | 51.0 | 23.0 | — | — | — | — |
| 28 | (58) | 73.5 | 12.0 | 52.5 | 21.0 | — | — | — | — |
| 29 | (61) | 70.5 | 9.0 | 55.0 | 15.5 | — | — | — | — |
| 30 | (65) | 61.5 | 0 | 44.0 | 17.5 | — | — | — | — |

*DTm relative to ODN22.

This data demonstrates the enhancement in melting point afforded by oligonucleotides containing invention bases. The increased $\Delta Tm(31-32)$ and $\Delta Tm(33-34)$ values obtained with invention bases (57), (58) and (59) indicate that these invention bases have an increased binding specificity compared to 5-methylcytosine or 5-(1-propynyl) cytosine.

EXAMPLE 5

Increased potency of gene expression inhibition. We made a 20-mer phosphorothioate-linked DNA oligonucleotide, 5' TCC-CGC-XTG-TGA-CAT-CGA-TT 3' (SEQ ID NO. 25), where X was a structure (57) base. The oligonucleotide was complementary to the 3' untranslated region of the c-raf mRNA. A control oligonucleotide had the same sequence except that the X base was replaced with cytosine. Each oligonucleotide was tested to determine its potency at inhibiting expression c-raf gene expression essentially as described (Monia "Nature Med" 2:668–675 1966, WO 97/32604). Briefly, a range of concentrations of each oligonucleotide was transfected into A549 small lung carcinoma cells on two consecutive days, followed by preparing cell extracts 48 hours after the first transfection. Immunoblot assay for c-raf protein expression showed the control oligonucleotide reduced c-raf protein expression with an $IC_{50}$ of about 20 nM. The test oligonucleotide containing the structure (57) base in place of cytosine was at least 20-fold more potent and had an $IC_{50}$ of less than 1 nM.

Similar assays using an oligonucleotide containing about 8–18 bases that are complementary to raf or c-raf, e.g., the oligonucleotide sequence used in this example or a shortened version thereof, is accomplished in a similar manner using invention oligonucleotides containing 1, 2 or 3 invention bases having an $R^2$ moiety that increases binding affinity compared to a control oligonucleotide containing cytosine.

We claim:
1. A compound having the structure (1):

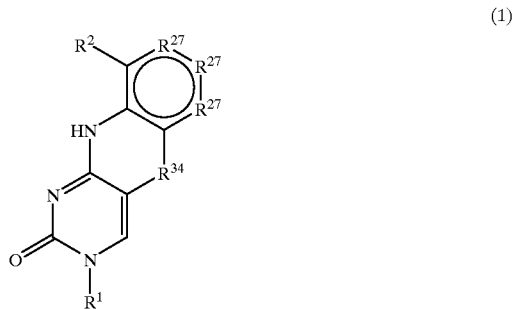

(1)

and tautomers, solvates and salts thereof, wherein
$R^1$ is an oligonucleotide, a protecting group, a linker or —H;
$R^2$ is $A(Z)_{X1}$, wherein A is a spacer and Z independently is a label bonding group optionally bonded to a detectable label, but $R^2$ is not amine, protected amine, nitro or cyano;
$R^{27}$ is independently —CH=, —N=, —C($C_1$-$C_8$ alkyl)= or —C(halogen)=, but no adjacent $R^{27}$ are both —N=, or two adjacent $R^{27}$ are taken together to form a ring having the structure,

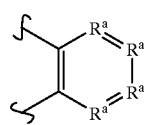

where $R^a$ is independently —CH=, —N=, —C($C_{1-8}$ alkyl)= or —C(halogen)=, but no adjacent $R^a$ are both —N=;
$R^{34}$ is —O—, —S— or —N(CH$_3$)—; and
X1 is 1, 2 or 3.
2. The compound of claim 1 wherein $R^2$ is —$R^{2C}$—$R^{2D}$, wherein $R^{2C}$ is a short spacer chain and $R^{2D}$ is a hydrogen bond donor moiety or a moiety having a net positive charge of at least about +0.5 at pH 6–8 in aqueous solutions.

3. The compound of claim 1 wherein $R^2$ is
—$R^6$—$(CH_2)_t$$NR^5$C($NR^5$)($NR^3$)$_2$, —$R^6$—$CH_2$—$CHR^{31}$—
$N(R^3)_2$, —$R^6$—$(R^7)_v$—$N(R^3)_2$, —$R^6$—$(CH_2)_t$—$N(R^3)_2$,
—$(CH_2)_{1-2}$—O—$(CH_2)_t$—$N(R^3)_2$, (40)

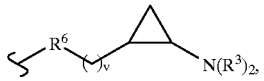

(41)

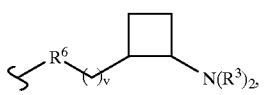

(42)

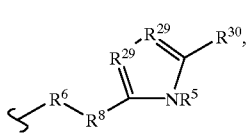

(43)

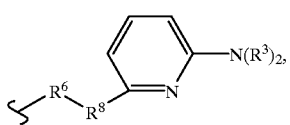

(44)

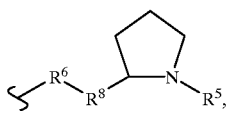

(45)

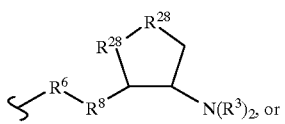

(46)

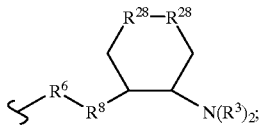

$R^3$ is independently —H, —$CH_3$, —$CH_2CH_3$, —$(CH_2)_w$—$N(R^{33})_2$ or a protecting group, or both $R^3$ together are a protecting group, or when $R^2$ is —$R^6$—$(CH_2)_t$—$N(R^3)_2$, one $R^3$ is —H, —$CH_3$, —$CH_2CH_3$, a protecting group or —$(CH_2)_w$—$N(R^{33})_2$ and the other $R^3$ is —H, —$CH_3$, —$CH_2CH_3$, —$(CH_2)_w$—$N(R^{33})_2$, —$CH(N[R^{33}]_2)$—$N(R^{33})_2$, (48)

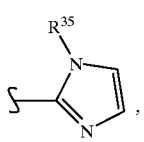

(49)

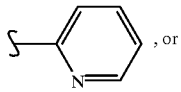, or (50)

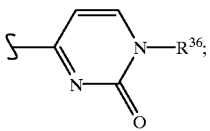

$R^5$ is independently H or a protecting group;
$R^6$ is independently —S—, —$NR^5$—, —O— or —$CH_2$—;
$R^7$ is independently linear alkyl having 1, 2, 3 or 4 carbon atoms optionally substituted with one —CH=CH—, —C≡C— or —$CH_2$—O—$CH_2$— moiety, or $R^7$ is cyclic alkyl having 3, 4 or 5 carbon atoms, wherein one of the linear alkyl carbon atoms is optionally substituted with a single —$CH_3$, —CN, =O, —OH or protected hydroxyl, provided that the carbon atoms in any —CH=CH— or —$CH_2$—O—$CH_2$— moiety are not substituted with =O, —OH or protected hydroxyl;
$R^8$ is linear alkylene having 1 or 2 carbon atoms wherein one alkylene carbon atom is optionally substituted with a single —$CH_3$, —CN, =O, —OH or protected hydroxyl, or $R^8$ is absent;
$R^{28}$ is independently —$CH_2$—, —$CH(CH_3)$—, —CH($OCH_3$)—, —$CH(OR^5)$— or —O—, but both are not —O—;
$R^{29}$ is independently —N—, —$N(CH_3)$—, —CH—, —$C(CH_3)$—, but both are not —$N(CH_3)$—;
$R^{30}$ is —H or —$N(R^3)_2$;
$R^{31}$ is the side chain of an amino acid;
$R^{33}$ is independently —H, —$CH_3$, —$CH_2CH_3$ or a protecting group;
$R^{35}$ is H, $C_1$-$C_4$ alkyl or a protecting group;
$R^{36}$ is —H, —$CH_3$, —$CH_2CH_3$, a protecting group or an optionally protected monosaccharide;
t is 1, 2, 3 or 4, but when $R^6$ is —O—, —S— or —$NR^5$—, t is 2, 3 or 4;
v is independently 0, 1 or 2; and
w is independently 1 or 2.

4. The compound of claim 3 wherein $R^2$ is —$CH_2$—$(CH_2)_t$$N(R^3)_2$, —$NR^5$—$(CH_2)_t$$N(R^3)_2$, —S—$(CH_2)_t$$N(R^3)_2$, —O—$(CH_2)_t$$N(R^3)_2$, —O—$(CH_2)_t$$NR^5$C($NR^5$)($NR^3$)$_2$, —$(CH_2)_{1-2}$—O—$(CH_2)_t$$N(R^3)_2$, —$R^6$—$CH_2$—$CHR^{31}$—N($R^3)_2$, —$R^6$—$(R^7)_v$—$N(R^3)_2$, —$R^6$—$(CH_2)_t$—$NR^5$C($NR^5$)($NR^3$)$_2$, or —$CH_2(CH_2)_t$$NR^5$C($NR^5$)($NR^3$)$_2$.

5. The compound of claim 4 wherein t is 2.

6. The compound of claim 5 wherein $R^3$ independently is —H, —$CH_3$ —$C_2H_5$ or a protecting group.

7. The compound of claim 6 wherein $R^2$ is —O—$(CH_2)_2$—$NH_2$, —O—$(CH_2)_3$—$NH_2$, —O—$(CH_2)_2$—$N(CH_3)_2$, —O—$(CH_2)_3$—$N(CH_3)_2$, —O—$(CH_2)_2$—$NHCH_3$, —O—$(CH_2)_3$—$NHCH_3$, —O—$CH_2$—$CH(CH_3)$—$NH_2$, —$CH_2$—O—$(CH_2)_2$—$NH_2$, —$CH_2$—O—$(CH_2)_3$—$NH_2$ or —$(CH_2)_2$—O—$(CH_2)_2$—$NH_2$.

8. The compound of claim 3 wherein t is 2 or 3.

9. The compound of claim 1 wherein $R^1$ comprises —H, an optionally protected monosaccharide, hydroxyl, phosphate or hydrogen phosphonate.

10. The compound of claim 1 wherein $R^1$ is optionally protected 2'-deoxy-$R^{21}$-substituted ribose, 2'-deoxyribose or ribose, wherein $R^{21}$ is H, —OH, halogen or a moiety that enhances the nuclease stability of an oligonucleotide containing the optionally protected 2'-deoxy-$R^{21}$-substituted ribose, 2'-deoxyribose or ribose.

11. The compound of claim 1 having the structure designated by the numbers selected from the group consisting of (104), (105), (133), (134), (111), (112), (113), (115), (135), (136), (137), (138), (139), (120), (121), (121A), (143), (122), (123), (125), or (126):
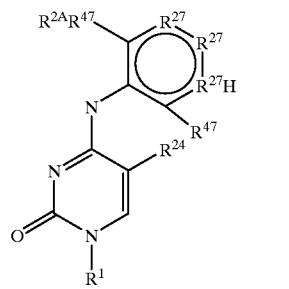
(104)
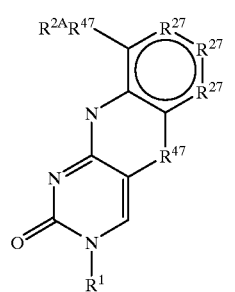
(105)
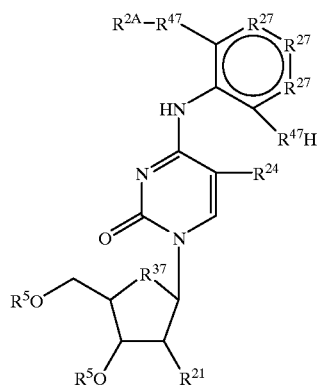
(133)
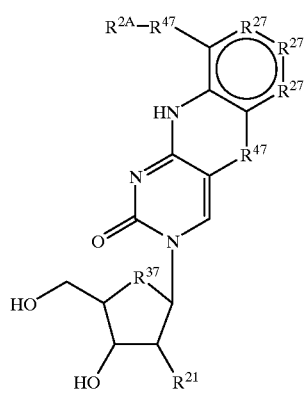
(134)
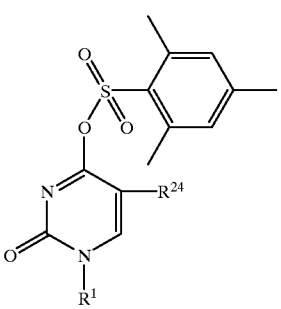
(111)
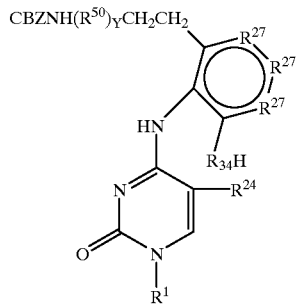
(112)
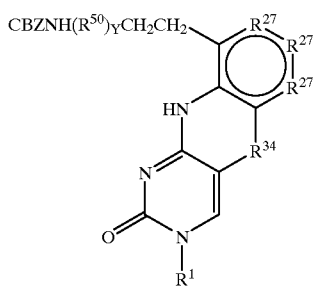
(113)
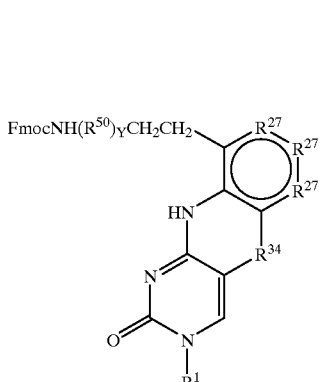
(114)

-continued
(135)
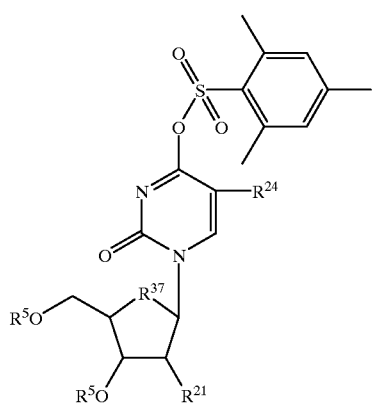
(136)
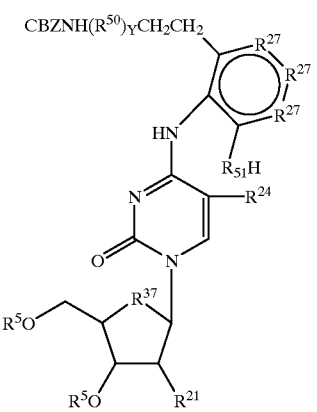
(137)
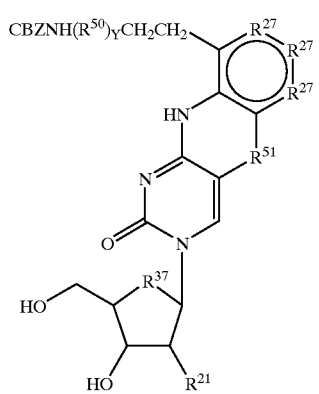
(138)
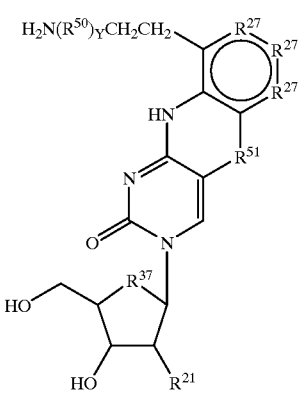
-continued
(120)
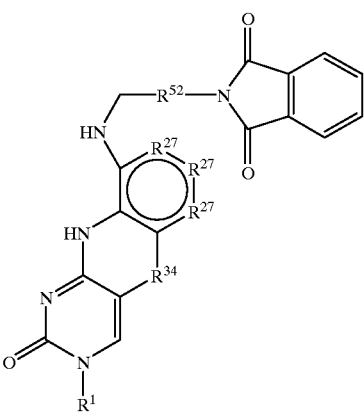
(143)
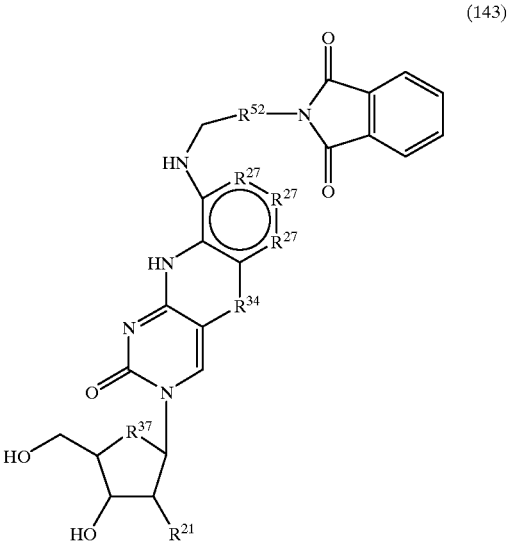
(122)

-continued (123)

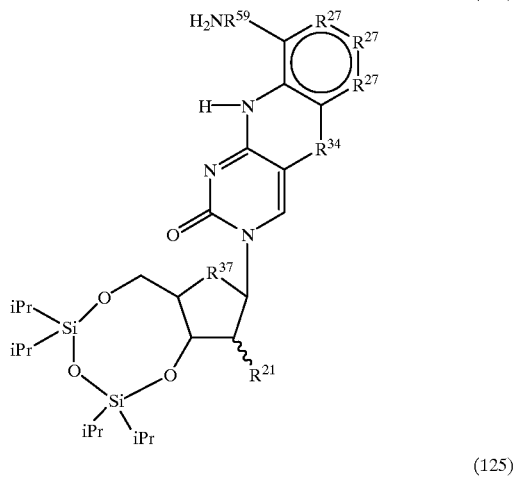

(125)

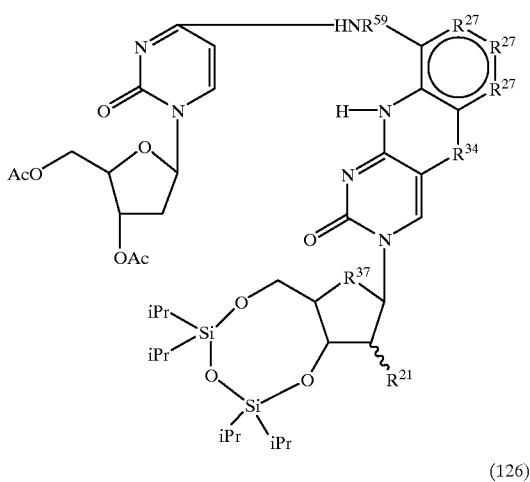

(126)

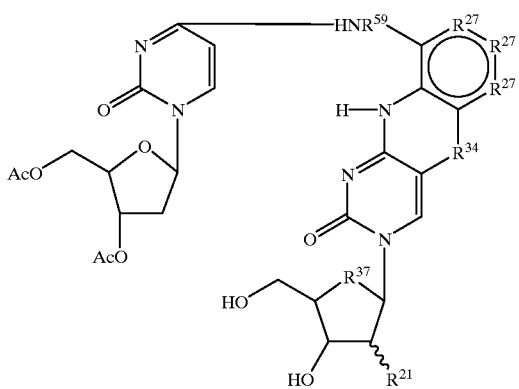

wherein
$R^1$ is an optionally protected monosaccharide;
$R^{2A}$ is —OH;
$R^5$ is independently —H or a protecting group;
$R^6$ is —O—, —S—, —NH— or —CH$_2$—;
$R^{21}$ is H, —OH, halogen or a moiety that enhances the nuclease stability of an oligonucleotide;
$R^{24}$ is a halogen;
$R^{27}$ is independently —CH=, —N=, —C(C$_1$-C$_8$ alkyl)= or —C(halogen =, but no adjacent $R^{27}$ are both —N=, or two adjacent $R^{27}$ are taken together to form a ring having the structure,

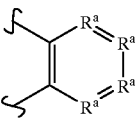

where $R^a$ is independently —CH=, —N=, —C(C$_{1-8}$ alkyl)= or —C(halogen)=, but no adjacent $R^a$ are both —N=;
$R^{34}$ is —O—, —S— or —N(CH$_3$)—;
$R^{37}$ is —O—, —CH$_2$— or —CF$_2$—;
$R^{47}$ is —O— or —S—;
$R^{50}$ is —CH$_2$—, —C(O)—, —(CH$_2$)$_2$—O—(CH$_2$)$_2$—, —(CH$_2$)$_2$—NR$^5$—(CH$_2$)$_2$—, —(CH$_2$)$_2$—S—(CH$_2$)$_2$—, —CH(N(R$^5$)$_2$)—, —CH(COOR$^5$)— or —C(CH$_3$)—, —C(C$_2$C$_5$)— but adjacent moieties are not C(O);
$R^{52}$ is —(CHR$^{52A}$)—(R$^{52B}$)—CHR$^{52A}$—, —CHR$^{52A}$—O—CHR$^{52A}$—, —CHR$^{52A}$—S—CHR$^{52A}$—, —CHR$^{52A}$—NR$^5$—CHR$^{52}$A—, C$_1$-C$_{10}$ alkylene optionally substituted with 1 or 2 moieties selected from the group consisting of C$_1$-C$_6$ alkyl, —OR$^5$, =O, —NO$_2$, —N$_3$, —CN, —COOR$^5$, or —N(R$^5$)$_2$, wherein any heteroatom is separated from the nitrogen atoms that $R^{52}$ is linked to by one methylene and one or more —CHR$^{52A}$—;
$R^{52A}$ is —H or C$_1$-C$_6$ alkyl;
$R^{52B}$ is a bond;
$R^{59}$ is —R$^6$—R$^{60}$—;
$R^{60}$ is —(CH$_2$)$_{Z3}$—(R$^{61}$)$_{Z1}$—(CH$_2$)$_{Z2}$—;
$R^{61}$ is —O—, —S—, —NR$^5$—, —C(O)—, —CH$_2$—O—CH$_2$—, —CH$_2$—NR$^5$—CH$_2$— or CH$_2$—S—CH$_2$—;
Z1 is 0 or 1;
Z2 is 1, 2 or 3;
Z3 is 1, 2 or 3;
Y is 1, 2, 3 or 4;
CBZ is carboxybenzoyl;
Fmoc is 9-fluorenylmethoxycarbonyl;
iPr is isopropyl; and
Ac is acetyl.

12. The compound of claim 1 wherein $R^1$ is an oligonucleotide having the structure (2):

(2)

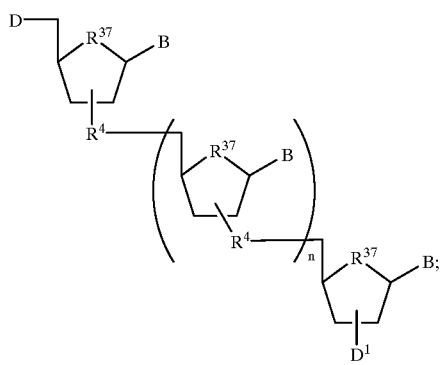

wherein

D is —OH, protected —OH, an oligonucleotide coupling group or a solid support;

$D^1$ is an oligonucleotide coupling group, —OH, protected —OH or a solid support, wherein $D^1$ is bonded to one 2' or 3' position in the oligonucleotide of structure (2) and the adjacent 2' or 3' position in structure (2) is substituted with $R^{21}$, provided that D and $D^1$ are not both an oligonucleoide coupling group or they are not both a solid support;

$R^4$ is independently a phosphodiester linkage or a phosphodiester substitute linkage, wherein $R^4$ is bonded to one 2' or 3' position in the structure (2) oligonucleotide and the adjacent 2' or 3' position in structure (2) is substituted with $R^{21}$;

$R^{21}$ is independently —H, —OH, halogen or a moiety that enhances the oligonucleotide against nuclease cleavage;

$R^{37}$ is independently —O—, —CH$_2$—, —CF$_2$—;

n is an integer from 0 to 98; and

B independently is a purine or pyrimidine base or a protected derivative thereof, provided that at least one B is a base of structure (3)

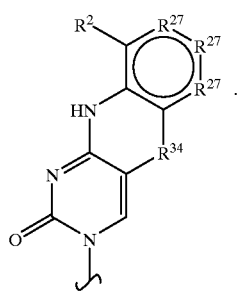

(3)

13. The compound of claim 12 wherein $R^4$ is independently 3'-O—P(S)(S)—O-5', 3'-O—P(S)(O)—O-5', 3'-O—P(O)(O)—O-5', 3'-O—P(Me)(O)—O-5', 3'-NH—P(O)(O)—O-5', 3'-S—CH$_2$—O-5', 2'-S—CH$_2$—O-5', 3'-O—CH$_2$—O-5', 2'-O—CH$_2$—O-5', 3'O—P(Me)(S)—O-5', 3'-CH$_2$—N(CH$_3$)—O-5', 2'-CH$_2$—N(CH$_3$)—O-5', or 3'-$R^{38}$—P(N$_2$)(O)—O-5', wherein $R^{38}$ independently is —O—, —CH$_2$— or —NH—;

$R^{39}$ is a protecting group;

$R^{40}$ independently is hydrogen, a protecting group, $C_1$–$C_{12}$ alkyl optionally substituted with one, or two —O—, —C(O)—, —OC(O)—, —C(O)O—, —OR$^{42}$, —SR$^{43}$, —C(O)NR$^{39}$—, —C(O)N(R$^{41}$)$_2$, —NR$^{41}$—, —N(R$^{41}$)$_2$, halo, —CN, or —NO$_2$ moieties, or both $R^{40}$ together with the nitrogen atom to which they are attached form

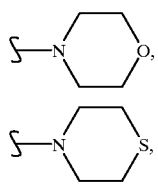

-continued

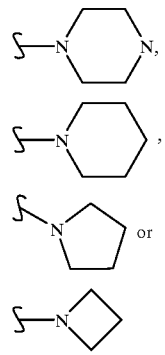

or both $R^{40}$ together are a protecting group;

$R^{41}$ independently is hydrogen, a protecting group, alkyl ($C_1$–$C_4$ or both $R^{41}$ together are a protecting group;

$R^{42}$ is hydrogen or a protecting group;

$R^{43}$ is $C_{1-6}$ alkyl or a protecting group; and $R^{45}$ is —H, a counter ion or

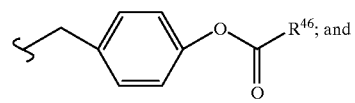

$R^{46}$ is alkyl containing 1–8 carbon atoms.

14. The compound of claim 12 wherein $R^2$ is —$R^6$—(CH$_2$)$_t$NR$^5$C(NR$^5$)(NR$^3$)$_2$, —$R^6$—CH$_2$—CHR$^{31}$—N(R$^3$)$_2$, —$R^6$—(R$^7$)$_v$—N(R$^3$)$_2$, —$R^6$—(CH$_2$)$_t$—N(R$^3$)$_2$, —(CH$_2$)$_{1-2}$—O—(CH$_2$)$_t$—N(R$^3$)$_2$,

(40)

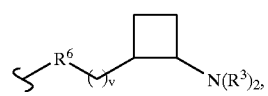
(41)

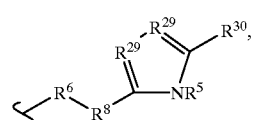
(42)

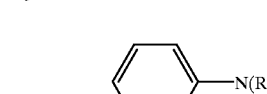
(43)

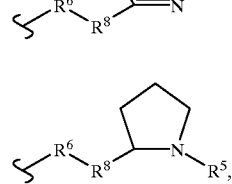
(44)

-continued

(45)
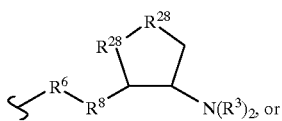

(46)
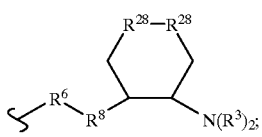

$R^3$ is independently —H, —$CH_3$, —$CH_2CH_3$, —$(CH_2)_w$—$N(R^{33})_2$ or a protecting group, or both $R^3$ together are a protecting group, or when $R^2$ is —$R^6$—$(CH_2)_t$—$N(R^3)_2$, one $R^3$ is —H, —$CH_2CH_3$, a protecting group or —$(CH_2)_w$—$N(R^{33})_2$ and the other $R^3$ is —H, —$CH_3$, —$CH_2CH_3$, —$(CH_2)_w$—$N(R^{33})_2$, —CH$(N[R^{33}]_2)$—$N(R^{33})_2$, (48)

(49)

(50)

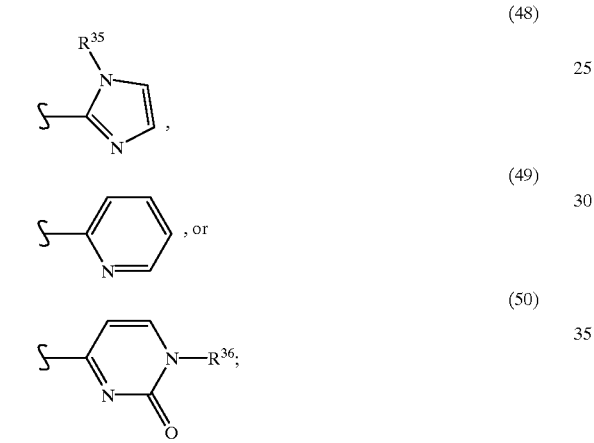

$R^5$ is independently H or a protecting group;

$R^6$ is independently —S—, —$NR^5$—, —O— or —$CH_2$—;

$R^7$ is independently linear alkyl having 1, 2, 3 or 4 carbon atoms optionally substituted with one —CH=CH—, —C≡C— or —$CH_2$—O—$CH_2$— moiety, or $R^7$ is cyclic alkyl having 3, 4 or 5 carbon atoms, wherein one of the linear alkyl carbon atoms is optionally substituted with a single —$CH_3$, —CN, =O, —OH or protected hydroxyl, provided that the carbon atoms in any —CH=CH— or —$CH_2$—O—$CH_2$— moiety are not substituted with =O, —OH or protected hydroxyl;

$R^8$ is linear alkylene having 1 or 2 carbon atoms wherein one alkylene carbon atom is optionally substituted with a single —$CH_3$, —CN, =O, —OH or protected hydroxyl, or $R^8$ is absent;

$R^{28}$ is independently —$CH_2$—, —CH($CH_3$)—, —CH($OCH_3$)—, —CH($OR^5$)— or —O—, but both are not —O—;

$R^{29}$ is independently —N—, —N($CH_3$)—, —CH—, —C($CH_3$)—, but both are not —N($CH_3$)—;

$R^{30}$ is —H or —$N(R^3)_2$;

$R^{31}$ is the side chain of an amino acid;

$R^{33}$ is independently —H, —$CH_3$, —$CH_2CH_3$ or a protecting group;

$R^{35}$ is H, $C_1$–$C_4$ alkyl or a protecting group;

$R^{36}$ is —H, —$CH_3$, —$CH_2CH_3$, a protecting group or an optionally protected monosaccharide;

t is 1, 2, 3 or 4, but when $R^6$ is —O—, —S— or —$NR^5$—, t is 2, 3 or 4;

v is independently 0, 1 or 2; and w is independently 1 or 2.

15. The compound of claim 14 wherein $R^2$ is —$CH_2$—$(CH_2)_t N(R^3)_2$, —$NR^5$—$(CH_2)_t N(R^3)_2$, —S—$(CH_2)_t N(R^3)_2$, —O—$(CH_2)_t N(R^3)_2$, —O—$(CH_2)_t NR^5 C(NR^5)(NR^3)_2$, —$(CH_2)_{1-2}$—O—$(CH_2)_t N(R^3)_2$, —$R^6$—$CH_2$—$CHR^{31}$—N$(R^3)_2$, —$R^6$—$(R^7)_v$—$N(R^3)_2$, —$R^6$—$(CH_2)_t$—$NR^5 C(NR^5)(NR^3)_2$, or —$CH_2(CH_2)_t NR^5 C(NR^5)(NR^3)_2$.

16. The compound of claim 15 wherein t is 2 or 3.

17. The compound of claim 16 wherein $R^3$ independently is —H, —$CH_3$, —$C_2H_5$ or a protecting group.

18. The compound of claim 17 wherein $R^2$ is —O—$(CH_2)_2$—$NH_2$, —O—$(CH_2)_3$—$NH_2$, —O—$(CH_2)_2$—$N(CH_3)_2$, —O—$(CH_2)_3$—$N(CH_3)_2$, —O—$(CH_2)_2$—$NHCH_3$, —O—$(CH_2)_3$—$NHCH_3$, —O—$CH_2$—CH($CH_3$)—$NH_2$, —$CH_2$—O—$(CH_2)_2$—$NH_2$, —$CH_2$—O—$(CH_2)_3$—$NH_2$ or —$(CH_2)_2$—O—$(CH_2)_2$—$NH_2$.

19. The compound of claim 12 wherein $R^{21}$ is independently —H, —OH, halogen, protected hydroxyl, —O-methyl, —O-ethyl, —O-n-propyl, —O-allyl, —O—$(CH_2)_2 OH$, —O—$(CH_2)_3 OH$, —O—$(CH_2)_2 F$, —O—$(CH_2)_s R^{65}$, —O—$(CH_2)_2$—[O—$(CH_2)_2]_r R^{65}$, —O—$(CH_2)_r$—O—$(CH_2)_r$—O—$(CH_2)_r$—$R^{65}$), —NH-methyl, —NH-ethyl, —NH-n-propyl, —NH—$(CH_2)_2 OH$, —NH—$(CH_2)_3 OH$, —NH—$(CH_2)_s R^{65}$, —S-methyl, —S-ethyl, —S-n-propyl, —S-allyl, —S—$(CH_2)_2 OH$, —S—$(CH_2)_3 OH$ —S—$(CH_2)_2 F$, —S—$(CH_2)_s R^{65}$, or —S—$(CH_2)_2$—[O—$(CH_2)_2]_r R^{65}$, wherein $R^{65}$ is —H, —F, —OH, —$OCH_3$, —$NH_2$, —SH, protected hydroxyl, protected amino or protected thiol;

r is 1, 2, 3 or 4; and s is 2, 3, 4, 5, 6, 7 or 8.

20. The compound of claim 19 wherein $R^{21}$ is independently —H, —OH, —F, protected hydroxyl, —$OCH_3$, —O—$CH_2CH_3$, —O—$CH_2CH_2OH$, —O—$CH_2CH_2F$, —O—$CH_2CH_2CH_3$, —O—$CH_2CH_2CH_2OH$, —O—$CH_2CH_2CH_2F$, —O—$CH_2CF_2H$, —O—$CH_2CF_3$ or —O—$CH_2CH_2$—O—$CH_3$.

21. The compound of claim 12 wherein B independently are selected from the group consisting of a base of structure (3), guanosine, adenine, thymine, uracil, cytosine, 5-methylcytosine, 5-(1-propynyl)uracil, 5-(1-propynyl) cytosine, 5-(1-butynyl)uracil therefor 5-(1-butynyl)cytosine.

22. The compound of claim 12 wherein $D^1$ is H-phosphonate, a methylphosphonamidite, a β-cyanoethylphosphoramidite or a phosphoramidite.

23. A compound having the structure (4)

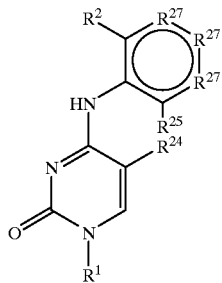
(4)

and tautomers, solvates and salts thereof wherein, $R^1$, $R^2$ and $R^{27}$ have the meanings given in claim 1;

$R^{24}$ is a halogen;

$R^{25}$ is —SH, —OH, =S or =O.

24. The compound of claim 23 wherein $R^1$ is —H or an optionally protected monosaccharide.

25. The compound of claim 24 wherein the optionally protected monosaccharide is 2'-deoxy-$R^{21}$-substituted ribose, wherein $R^{21}$ is H, —OH, halogen or a moiety that enhances the nuclease stability of an oligonucleotide containing the optionally protected 2'-deoxy-$R^{21}$-substituted ribose, 2'-deoxyribose or ribose.

26. The compound of claim 25 wherein $R^{21}$ is —H, —OH, —F, protected hydroxyl, —OCH$_3$, —O—CH$_2$CH$_3$, —O—CH$_2$CH$_2$OH, —O—CH$_2$CH$_2$F, —O—CH$_2$CH$_2$CH$_3$, —O—CH$_2$CH$_2$CH$_2$OH, —O—CH$_2$CH$_2$CH$_2$F, —O—CH$_2$CF$_2$H, —O—CH$_2$CF$_3$ or —O—CH$_2$CH$_2$—O—CH$_3$.

27. The compound of claim 1 having the structure (1):

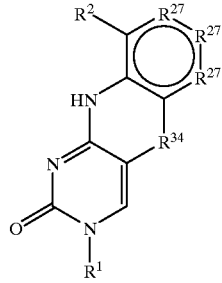
(1)

and tautomers, solvates and salts thereof, wherein $R^1$ is a protecting group, an oligonucleotide, a nucleic acid, a polysaccharide, an optionally protected monosaccharide, hydroxyl, phosphate, hydrogen phosphonate, halo, azido, protected hydroxyl, or —H;

$R^2$ is $A(Z)_{X1}$, but $R^2$ is not amine, protected amine, nitro or cyano;

$R^5$ is H or a protecting group;

$R^{27}$ is independently —CH=, —N=, —C(C$_1$-C$_8$ alkyl)= or —C(halogen)=, but no adjacent $R^{27}$ are both —N=, or two adjacent $R^{27}$ are taken together to form a ring having the structure,

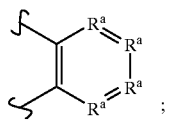
;

$R^{34}$ is —O—, —S— or —N(CH$_3$)—;

$R^a$ is independently —CH=, —N=, —C(C$_{1-8}$ alkyl)= or —C(halogen)=, but no adjacent $R^a$ are both —N=;

A is a backbone chain of 2–16 carbon atoms, any 1, 2 or 3 of which are optionally replaced with N, O or S atoms, wherein the backbone chain is optionally substituted independently with 1, 2 or 3 of the following: C$_1$-C$_8$ alkyl, —OR$^5$, =O, —NO$_2$, —N$_3$, —COOR$^5$, —N(R$^5$)$_2$, or —CN groups, C$_1$-C$_8$ alkyl substituted with —OH, =O, —NO$_2$, —N$_3$, —COOR$^5$, —N(R$^5$)$_2$, or —CN groups, or any of the foregoing in which —CH$_2$— is replaced with —O—, —NH— or —N(C$_1$-C$_8$ alkyl);

X1 is 1, 2 or 3;

Y is H, 2-hydroxypyridine, N-hydroxysuccinimide, p-nitrophenyl, acylimidazole, maleimide, trifluoroacetate, an imido, a sulfonate, an imine 1,2-cyclohexanedione, glyoxal or an alpha-halo ketone; and Z independently is —NH$_2$, —CHO, —SH, —CO$_2$Y, OY.

28. The compound of claim 27 wherein Z is bonded to a detectable label.

29. The compound of claim 27 wherein $R^1$ is an oligonucleotide.

30. The compound of claim 27 wherein $R^1$ is an optionally protected monosaccharide.

* * * * *